United States Patent
Breyer et al.

(10) Patent No.: US 6,383,777 B1
(45) Date of Patent: May 7, 2002

(54) METHODS AND COMPOSITIONS FOR HIGH YIELD PRODUCTION OF EUKARYOTIC PROTEINS

(75) Inventors: Richard M. Breyer; Lijun Ma; Chris Kennedy, all of Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/293,170

(22) Filed: Apr. 16, 1999

Related U.S. Application Data
(60) Provisional application No. 60/081,989, filed on Apr. 16, 1998.

(51) Int. Cl.⁷ ............................ C12P 21/06; C07K 1/00; C07H 21/04
(52) U.S. Cl. ................... 435/69.1; 435/69.7; 435/69.8; 530/300; 530/350; 530/387.3; 536/23.1; 536/23.4; 536/23.7; 536/23.72
(58) Field of Search ................................. 536/23.4, 23.1, 536/23.7, 23.72; 435/69.1, 69.7, 69.8; 530/300, 350, 387.3

(56) References Cited

U.S. PATENT DOCUMENTS
5,665,865 A   9/1997   Lerner et al. ............ 530/387.3

OTHER PUBLICATIONS
Bryer et al., EMBO J. 9(2679–2684) 1990.*
Grisshammer and Tate Q. Rev. Biophys. 28(3)315–422, 1995.*
Kifer et al. Biochemistry 35(16077–16084), Oct. 1996.*
Flores, N. et al., Appl Microbiol. Biotechnol. 25(267–271)1986.*
Krautwald et al., Biochem. Biophys. Res. Comm. 192:2(720–727)1993.*
Hayashi, M.K. et al., J. Biochem. 120(1232–1238)1996.*
Bastien, L. et al., J. Biol. Chem. 269:16(11873–11877)1994, 1986.*
Beyer et al., "Mutational analysis of the fine specificity of binding of monoclonal antibody 51F to λ repressor." *J. Biol. Chem.* 264(22):13355–13360, Aug. 1989.
Ramjeesingh et al. "A Novel Procedure for the Efficient Purification of the Cystic Fibrosis Transmembrane Conductance Regulator (CFTR)" *Biochem. J.* 327:17–21, 1997.
Loisel et al. "Recovery of Homogeneous and Functional β₂–Adrenergic Receptors from Extracellular Baculovirus Particles" *Nature Biotech.* 15:1300–1304, Nov. 1997.

Sander et al. "Expression of the Human $D_{2S}$ Dopamine Receptor in the Yeasts *Saccharomyces cerevisiae* and *Schizosaccharomyces pombe*: a comparative study" *FEBS Letters* 334:41–46, 1994.

Breyer et al. "Mutational Analysis of Ligand Binding Activity of $\beta_2$ Adrenergic Receptor Expressed in *Escherichia coli*" *EMBO J.* 9(9):2679–2684, 1990.

Chapot et al. "Localization and Characterization of Three Different β–Adrenergic Receptors Expressed in *Escherichia coli*" *Eur. J. Biochem.* 187:137–144, 1990.

Marullo et al. "Human $\beta_2$–Adrenergic Receptors Expressed in *Escherichia coli* Membranes Retain their Pharmacological Properties" *Proc. Natl. Acad. Sci. USA* 85:7551–7555, Oct. 1988.

* cited by examiner

Primary Examiner—Yvonne Eyler
Assistant Examiner—Michael Brannock
(74) Attorney, Agent, or Firm—Needle & Rosenberg, P.C.

(57) ABSTRACT

The present invention provides an isolated nucleic acid comprising a first nucleotide sequence encoding an amino acid sequence comprising at least three positively charged amino acid residues, positioned upstream and in frame with a second nucleotide sequence encoding a protein. In addition, the present invention provides an isolated nucleic acid comprising a first nucleotide sequence encoding a DNA binding protein, positioned upstream and in frame with a second nucleotide sequence encoding a protein. An isolated nucleic acid is also provided, which comprises a first nucleotide sequence encoding a bacteriophage lambda repressor protein, positioned upstream and in frame with a second nucleotide sequence encoding a protein. The present invention further provides a method of producing a eukaryotic protein in a bacterial cell comprising: a) introducing the expression vector of this invention, wherein the second nucleotide sequence encodes a eukaryotic protein, into the bacterial cell; and b) culturing the bacterial cell under conditions whereby the second nucleotide sequence of the expression vector is expressed to produce the eukaryotic protein. A method of producing a eukaryotic protein in a bacterial cell in high yield is also provided, comprising: a) introducing the expression vector of this invention, wherein the second nucleotide sequence encodes a eukaryotic protein, into the bacterial cell; and b) culturing the bacterial cell under conditions whereby the second nucleotide sequence of the expression vector is expressed to produce the eukaryotic protein in high yield.

23 Claims, 1 Drawing Sheet

Primary antibody: affinity-purified sheep anti-human EP2 antibody
Secondary antibody: rabbit anti-sheep-HRP

SEQUENCE LISTING

```
<160> NUMBER OF SEQ ID NOS: 37

<210> SEQ ID NO 1
<211> LENGTH: 5856
<212> TYPE: DNA
<213> ORGANISM: Artificial Sequence
<220> FEATURE:
<221> NAME/KEY: CDS
<222> LOCATION: (300)...(1799)
<223> OTHER INFORMATION: Description of Artificial Sequence:/Note =
      synthetic construct

<400> SEQUENCE: 1
ttctcatgtt tgacagctta tctcatcgac tgcacggtgc accaatgctt ctggcgtcag      60
gcagccatcg gaagctgtgg tatggctgtg caggtcgtaa atcactgcat aattcgtgtc     120
gctcaaggcg cactcccgtt ctggataatg tttttttgcgc cgacatcata acggttctgg     180
caaatattct gaaatgagct gttgacaatt aatcatcggc tcgtataatg tggaattgtg     240
agcggataac aattaatgtg tgaatgtgag cggatacaat ttcacacagg aaacagcgt      299 atg agc aca aaa aag aaa cca tta aca caa gag cag ctt gag gac gca      347
Met Ser Thr Lys Lys Lys Pro Leu Thr Gln Glu Gln Leu Glu Asp Ala
```

-continued

```
  1               5                    10                   15 cgt cgc ctt aaa gca att tat gaa aaa aag aaa aat gaa ctt ggc tta        395
Arg Arg Leu Lys Ala Ile Tyr Glu Lys Lys Lys Asn Glu Leu Gly Leu
            20                  25                  30 tcc cag gaa tct gtc gca gac aag atg ggg atg ggg cag tca ggc gtt        443
Ser Gln Glu Ser Val Ala Asp Lys Met Gly Met Gly Gln Ser Gly Val
            35                  40                  45 ggt gct tta ttt aat ggc atc aat gca tta aat gct tat aac gcg gca        491
Gly Ala Leu Phe Asn Gly Ile Asn Ala Leu Asn Ala Tyr Asn Ala Ala
        50                  55                  60 ttg cta gca aaa att ctc aaa gtt agc gtt gaa gaa ttc gca gct cat        539
Leu Leu Ala Lys Ile Leu Lys Val Ser Val Glu Glu Phe Ala Ala His
65                  70                  75                  80 atg aag gag acg cgg ggc gac gga ggg agc gcc ccc ttc tgc acc cgc        587
Met Lys Glu Thr Arg Gly Asp Gly Gly Ser Ala Pro Phe Cys Thr Arg
                85                  90                  95 ctc aac cac tcg tat cca ggc atg tgg gcg ccc gag gca cgg ggc aac        635
Leu Asn His Ser Tyr Pro Gly Met Trp Ala Pro Glu Ala Arg Gly Asn
                100                 105                 110 ctc aca cgc ccc cca ggg ccc ggc gag gac tgt ggc tcg gtg tcc gtg        683
Leu Thr Arg Pro Pro Gly Pro Gly Glu Asp Cys Gly Ser Val Ser Val
            115                 120                 125 gcc ttc ccg atc acc atg ctg atc acc ggc ttc gtg ggc aac gcg ctg        731
Ala Phe Pro Ile Thr Met Leu Ile Thr Gly Phe Val Gly Asn Ala Leu
    130                 135                 140 gcc atg ctg ctc gtg tcg cgt agc tac cgg cgt cgg gag agc aag cgc        779
Ala Met Leu Leu Val Ser Arg Ser Tyr Arg Arg Arg Glu Ser Lys Arg
145                 150                 155                 160 aag aag tcg ttc ctg ttg tgc atc ggc tgg ctg gcg ctc act gac ctg        827
Lys Lys Ser Phe Leu Leu Cys Ile Gly Trp Leu Ala Leu Thr Asp Leu
                165                 170                 175 gtc ggg cag ctg ctc aca agc ccc gtg gtc atc ttg gtg tac cta tcc        875
Val Gly Gln Leu Leu Thr Ser Pro Val Val Ile Leu Val Tyr Leu Ser
            180                 185                 190 aag cag cgc tgg gag cag ctc gac ccg tcg ggg cgc ctg tgc acc ttc        923
Lys Gln Arg Trp Glu Gln Leu Asp Pro Ser Gly Arg Leu Cys Thr Phe
        195                 200                 205 ttt ggt ctg acc atg act gtt ttc ggg ctg tcc tcg ctc ttc atc gcc        971
Phe Gly Leu Thr Met Thr Val Phe Gly Leu Ser Ser Leu Phe Ile Ala
    210                 215                 220 agc gcc atg gct gtc gag agg gcg ctg gcc atc cgt gcg cca cac tgg       1019
Ser Ala Met Ala Val Glu Arg Ala Leu Ala Ile Arg Ala Pro His Trp
225                 230                 235                 240 tac gcg agc cac atg aag acg cgt gcc act cgc gcc gtc ctg ctg ggc       1067
Tyr Ala Ser His Met Lys Thr Arg Ala Thr Arg Ala Val Leu Leu Gly
                245                 250                 255 gtg tgg ctg gca gtg ctc gcc ttc gcc ctg cta cct gtg ctg ggt gtg       1115
Val Trp Leu Ala Val Leu Ala Phe Ala Leu Leu Pro Val Leu Gly Val
            260                 265                 270 ggt cag tac acc atc cag tgg ccc ggg acg tgg tgc ttc atc agc acc       1163
Gly Gln Tyr Thr Ile Gln Trp Pro Gly Thr Trp Cys Phe Ile Ser Thr
        275                 280                 285 gga cga ggg gac aac ggg acg agc tct tca cac aac tgg ggc aac ctt       1211
Gly Arg Gly Asp Asn Gly Thr Ser Ser Ser His Asn Trp Gly Asn Leu
    290                 295                 300 ttc ttc gcc tcc acc ttt gcc ttc ctg ggc ctc ttg gcg ctg gcc atc       1259
Phe Phe Ala Ser Thr Phe Ala Phe Leu Gly Leu Leu Ala Leu Ala Ile
305                 310                 315                 320 acc ttc acc tgc aac ctg gcc acc att aag gct ctg gtg tcc cgc tgc       1307
```

```
Thr Phe Thr Cys Asn Leu Ala Thr Ile Lys Ala Leu Val Ser Arg Cys
            325                 330                 335 cgg gca aag gcg gca gca tca cag tcc agt gcc cag tgg ggc cgg atc       1355
Arg Ala Lys Ala Ala Ala Ser Gln Ser Ser Ala Gln Trp Gly Arg Ile
        340                 345                 350 acg acc gag acg gcc atc cag ctc atg ggg atc atg tgc gtg ctg tcg       1403
Thr Thr Glu Thr Ala Ile Gln Leu Met Gly Ile Met Cys Val Leu Ser
            355                 360                 365 gtc tgc tgg tcg ccc cta ctg ata atg atg ttg aaa atg atc ttc aat       1451
Val Cys Trp Ser Pro Leu Leu Ile Met Met Leu Lys Met Ile Phe Asn
370                 375                 380 cag aca tca gtt gag cac tgc aag aca gac aca gga aag cag aaa gaa       1499
Gln Thr Ser Val Glu His Cys Lys Thr Asp Thr Gly Lys Gln Lys Glu
385                 390                 395                 400 tgc aac ttc ttc tta ata gct gtt cgc ctg gct tca ctg aac cag ata       1547
Cys Asn Phe Phe Leu Ile Ala Val Arg Leu Ala Ser Leu Asn Gln Ile
                405                 410                 415 ttg gat ccc tgg gtt tat ctg ctg cta aga aag att ctt ctt cgg aag       1595
Leu Asp Pro Trp Val Tyr Leu Leu Leu Arg Lys Ile Leu Leu Arg Lys
            420                 425                 430 ttt tgc cag gta att cat gaa aat aat gag cag aag gat gaa att cag       1643
Phe Cys Gln Val Ile His Glu Asn Asn Glu Gln Lys Asp Glu Ile Gln
        435                 440                 445 cgt gag aac agg aac gtc tca cac agt ggg caa cac gaa gag gcc aga       1691
Arg Glu Asn Arg Asn Val Ser His Ser Gly Gln His Glu Glu Ala Arg
    450                 455                 460 gac agt gag aag agc aaa acc atc cct ggc ctg ttc tcc att ctg ctg       1739
Asp Ser Glu Lys Ser Lys Thr Ile Pro Gly Leu Phe Ser Ile Leu Leu
465                 470                 475                 480 cag gct gac cct ggt gct cgt cct tat cag caa gcc tcg agg cac cat       1787
Gln Ala Asp Pro Gly Ala Arg Pro Tyr Gln Gln Ala Ser Arg His His
                485                 490                 495 cac cac cac cac tgaagcttta atgcggtagt ttatcacagt taaattgcta          1839
His His His His
        500 acgcagtcag gcaccgtgta tgaaatctaa caatgcgctc atcgtcatcc tcggcaccgt     1899 cacctggat gctgtaggca taggcttggt tatgccggta ctgccgggcc tcttgcggga      1959 tcgacgcgag gctggatggc cttccccatt atgattcttc tcgcttccgg cggcatcggg     2019 atgcccgcgt tgcaggccat gctgtccagg caggtagatg acgaccatca gggacagctt     2079 caaggatcgc tcgcggctct taccagccta acttcgatca ctggaccgct gatcgtcacg     2139 gcgatttatg ccgcctcggc gagcacatgg aacgggttgg catggattgt aggcgccgcc     2199 ctataccttg tctgcctccc cgcgttgcgt cgcggtgcat ggagccgggc cacctcgacc     2259 tgaatggaag ccggcggcac ctcgctaacg gattcaccac tccaagaatt ggagccaatc     2319 aattcttgcg gagaactgtg aatgcgcaaa ccaaccttg gcagaacata tccatcgcgt      2379 ccgccatctc cagcagccgc acgcggcgca tctcgggcag cgttgggtcc tggccacggg     2439 tgcgcatgat cgtgctcctg tcgttgagga cccggctagg ctggcggggt tgccttactg     2499 gttagcagaa tgaatcaccg atacgcgagc gaacgtgaag cgactgctgc tgcaaaacgt     2559 ctgcgacctg agcaacaaca tgaatggtct tcggtttccg tgtttcgtaa agtctggaaa     2619 cgcggaagtc agcgccctgc accattatgt tccggatctg catcgcagga tgctgctggc     2679 taccctgtgg aacacctaca tctgtattaa cgaagcgctg gcattgaccc tgagtgattt     2739 ttctctggtc ccgccgcatc cataccgcca gttgtttacc ctcacaacgt tccagtaacc     2799
```

```
gggcatgttc atcatcagta acccgtatcg tgagcatcct ctctcgtttc atcggtatca    2859
ttaccccat gaacagaaat tccccttac acggaggcat caagtgacca acaggaaaa      2919
aaccgccctt aacatggccc gctttatcag aagccagaca ttaacgcttc tggagaaact   2979
caacgagctg gacgcggatg aacaggcaga catctgtgaa tcgcttcacg accacgctga   3039
tgagctttac cgcagctgcc tcgcgcgttt cggtgatgac ggtgaaaacc tctgacacat   3099
gcagctcccg gagacggtca cagcttgtct gtaagcggat gccgggagca gacaagcccg   3159
tcagggcgcg tcagcgggtg ttggcgggtg tcggggcgca gccatgaccc agtcacgtag   3219
cgatagcgga gtgtatactg gcttaactat gcggcatcag agcagattgt actgagagtg   3279
caccatatgc ggtgtgaaat accgcacaga tgcgtaagga aaaataccg catcaggcgc    3339
tcttccgctt cctcgctcac tgactcgctg cgctcggtcg ttcggctgcg gcgagcggta   3399
tcagctcact caaaggcggt aatacggtta tccacagaat caggggataa cgcaggaaag   3459
aacatgtgag caaaaggcca gcaaaaggcc aggaaccgta aaaaggccgc gttgctggcg   3519
ttttccata ggctccgccc ccctgacgag catcacaaaa atcgacgctc aagtcagagg    3579
tggcgaaacc cgacaggact ataaagatac caggcgtttc ccctggaag ctccctcgtg    3639
cgctctcctg ttccgaccct gccgcttacc ggatacctgt ccgcctttct cccttcggga   3699
agcgtggcgc tttctcatag ctcacgctgt aggtatctca gttcggtgta ggtcgttcgc   3759
tccaagctgg gctgtgtgca cgaaccccc gttcagcccg accgctgcgc cttatccggt    3819
aactatcgtc ttgagtccaa cccggtaaga cacgacttat cgccactggc agcagccact   3879
ggtaacagga ttagcagagc gaggtatgta ggcggtgcta cagagttctt gaagtggtgg   3939
cctaactacg gctacactag aaggacagta tttggtatct gcgctctgct gaagccagtt   3999
accttcggaa aaagagttgg tagctcttga tccggcaaac aaaccaccgc tggtagcggt   4059
ggttttttg tttgcaagca gcagattacg cgcagaaaaa aaggatctca agaagatcct    4119
ttgatcttt ctacggggtc tgacgctcag tggaacgaaa actcacgtta agggattttg    4179
gtcatgagat tatcaaaaag gatcttcacc tagatccttt tacccggtt gataatcaga    4239
aaagccccaa aaacaggaag attgtataag caaatattta aattgtaaac gttaatattt   4299
tgttaaaatt cgcgttaaat ttttgttaaa tcagctcatt ttttaaccaa taggccgaaa   4359
tcggcaaaat cccttataaa tcaaaagaat agcccgagat agggttgagt gttgttccag   4419
tttggaacaa gagtccacta ttaaagaacg tggactccaa cgtcaaaggg cgaaaaaccg   4479
tctatcaggg cgatggccca ctacgtgaac catcacccaa atcaagtttt tgggggtcga   4539
ggtgccgtaa agcactaaat cggaacccta aagggagccc ccgatttaga gcttgacggg   4599
gaaagccggc gaacgtggcg agaaaggaag ggaagaaagc gaaaggagcg gcgctaggg    4659
cgctggcaag tgtagcggtc acgctgcgcg taaccaccac cccgccgcg cttaatgcgc    4719
cgctacaggg cgcgtaaatc aatctaaagt atatatgagt aaacttggtc tgacagttac   4779
caatgcttaa tcagtgaggc acctatctca gcgatctgtc tatttcgttc atccatagtt   4839
gcctgactcc ccgtcgtgta gataactacg atacgggagg cttaccatc tggccccagt    4899
gctgcaatga taccgcgaga cccacgctca ccggctccag atttatcagc aataaaccag   4959
ccagccggaa gggccgagcg cagaagtggt cctgcaactt tatccgcctc catccagtct   5019
attaattgtt gccgggaagc tagagtaagt agttcgccag ttaatagttt gcgcaacgtt   5079
gttgccattg ctgcaggcat cgtggtgtca cgctcgtcgt ttggtatggc ttcattcagc   5139
tccggttccc aacgatcaag gcgagttaca tgatccccca tgttgtgcaa aaaagcggtt   5199
```

-continued

```
agctccttcg gtcctccgat cgttgtcaga agtaagttgg ccgcagtgtt atcactcatg      5259
gttatggcag cactgcataa ttctcttact gtcatgccat ccgtaagatg cttttctgtg      5319
actggtgagt actcaaccaa gtcattctga aatagtgta tgcggcgacc gagttgctct      5379
tgcccggcgt caacacggga taataccgcg ccacatagca aactttaaa agtgctcatc      5439 attggaaaac gttcttcggg gcgaaaactc tcaaggatct taccgctgtt gagatccagt      5499
tcgatgtaac ccactcgtgc acccaactga tcttcagcat cttttacttt caccagcgtt      5559
tctgggtgag caaaaacagg aaggcaaaat gccgcaaaaa agggaataag ggcgacacgg      5619
aaatgttgaa tactcatact cttccttttt caatattatt gaagcattta tcagggttat      5679
tgtctcatga gcggatacat atttgaatgt atttagaaaa ataaacaaat aggggttccg      5739
cgcacatttc cccgaaaagt gccacctgac gtctaagaaa ccattattat catgacatta      5799
acctataaaa ataggcgtat cacgaggccc tttcgtcttc aagaattgat cgatcaa       5856
```

```
<210> SEQ ID NO 2
<211> LENGTH: 6446
<212> TYPE: DNA
<213> ORGANISM: Artificial Sequence
<220> FEATURE:
<221> NAME/KEY: CDS
<222> LOCATION: (300)...(2126)
<223> OTHER INFORMATION: Description of Artificial Sequence:/note =
      synthetic construct

<400> SEQUENCE: 2
```

```
ttctcatgtt tgacagctta tctcatcgac tgcacggtgc accaatgctt ctggcgtcag       60
gcagccatcg gaagctgtgg tatggctgtg caggtcgtaa atcactgcat aattcgtgtc      120
gctcaaggcg cactcccgtt ctggataatg ttttttgcgc cgacatcata acggttctgg      180
caaatattct gaaatgagct gttgacaatt aatcatcggc tcgtataatg tggaattgtg      240
agcggataac aattaatgtg tgaatgtgag cggatacaat ttcacacagg aaacagcgt      299
```

```
atg agc aca aaa aag aaa cca tta aca caa gag cag ctt gag gac gca       347
Met Ser Thr Lys Lys Lys Pro Leu Thr Gln Glu Gln Leu Glu Asp Ala
 1               5                  10                  15 cgt cgc ctt aaa gca att tat gaa aaa aag aaa aat gaa ctt ggc tta       395
Arg Arg Leu Lys Ala Ile Tyr Glu Lys Lys Lys Asn Glu Leu Gly Leu
            20                  25                  30 tcc cag gaa tct gtc gca gac aag atg ggg atg ggg cag tca ggc gtt       443
Ser Gln Glu Ser Val Ala Asp Lys Met Gly Met Gly Gln Ser Gly Val
        35                  40                  45 ggt gct tta ttt aat ggc atc aat gca tta aat gct tat aac gcg gca       491
Gly Ala Leu Phe Asn Gly Ile Asn Ala Leu Asn Ala Tyr Asn Ala Ala
 50                  55                  60 ttg cta gca aaa att ctc aaa gtt agc gtt gaa gaa ttc cat atg ggc       539
Leu Leu Ala Lys Ile Leu Lys Val Ser Val Glu Glu Phe His Met Gly
 65                  70                  75                  80 aat gcc tcc aat gac tcc cag tct gag gac tgc gag acg cga cag tgg       587
Asn Ala Ser Asn Asp Ser Gln Ser Glu Asp Cys Glu Thr Arg Gln Trp
                85                  90                  95 ctt ccc cca ggc gaa agc cca gcc atc agc tcc gtc atg ttc tcg gcc       635
Leu Pro Pro Gly Glu Ser Pro Ala Ile Ser Ser Val Met Phe Ser Ala
            100                 105                 110 ggg gtg ctg ggg aac ctc ata gca ctg gcg ctg ctg gcg cgc cgc tgg       683
Gly Val Leu Gly Asn Leu Ile Ala Leu Ala Leu Leu Ala Arg Arg Trp
        115                 120                 125 cgg ggg gac gtg ggg tgc agc gcc ggc cgc agg agc tcc ctc tcc ttg       731
```

```
Arg Gly Asp Val Gly Cys Ser Ala Gly Arg Arg Ser Ser Leu Ser Leu
    130                 135                 140 ttc cac gtg ctg gtg acc gag ctg gtg ttc acc gac ctg ctc ggg acc      779
Phe His Val Leu Val Thr Glu Leu Val Phe Thr Asp Leu Leu Gly Thr
145                 150                 155                 160 tgc ctc atc agc cca gtg gta ctg gct tcg tac gcg cgg aac cag acc      827
Cys Leu Ile Ser Pro Val Val Leu Ala Ser Tyr Ala Arg Asn Gln Thr
                165                 170                 175 ctg gtg gca ctg gcg ccc gag agc cgc gcg tgc acc tac ttc gct ttc      875
Leu Val Ala Leu Ala Pro Glu Ser Arg Ala Cys Thr Tyr Phe Ala Phe
            180                 185                 190 gcc atg acc ttc ttc agc ctg gcc acg atg ctc atg ctc ttc gcc atg      923
Ala Met Thr Phe Phe Ser Leu Ala Thr Met Leu Met Leu Phe Ala Met
        195                 200                 205 gcc ctg gag cgc tac ctc tcg atc ggg cac ccc tac ttc tac cag cgc      971
Ala Leu Glu Arg Tyr Leu Ser Ile Gly His Pro Tyr Phe Tyr Gln Arg
    210                 215                 220 cgc gtc tcg gcc tcc ggg ggc ctg gcc gtg ctg cct gtc atc tat gca     1019
Arg Val Ser Ala Ser Gly Gly Leu Ala Val Leu Pro Val Ile Tyr Ala
225                 230                 235                 240 gtc tcc ctg ctc ttc tgc tcg ctg ccg ctg ctg gac tat ggg cag tac     1067
Val Ser Leu Leu Phe Cys Ser Leu Pro Leu Leu Asp Tyr Gly Gln Tyr
                245                 250                 255 gtc cag tac tgc ccc ggg acc tgg tgc ttc atc cgg cac ggg cgg acc     1115
Val Gln Tyr Cys Pro Gly Thr Trp Cys Phe Ile Arg His Gly Arg Thr
            260                 265                 270 gct tac ctg cag ctg tac gcc acc ctg ctg ctg ctt ctc att gtc tcg     1163
Ala Tyr Leu Gln Leu Tyr Ala Thr Leu Leu Leu Leu Leu Ile Val Ser
        275                 280                 285 gtg ctc gcc tgc aac ttc agt gtc att ctc aac ctc atc cgc atg cac     1211
Val Leu Ala Cys Asn Phe Ser Val Ile Leu Asn Leu Ile Arg Met His
    290                 295                 300 cgc cga agc cgg aga agc cgc tgc gga cct tcc ctg ggc agt ggc cgg     1259
Arg Arg Ser Arg Arg Ser Arg Cys Gly Pro Ser Leu Gly Ser Gly Arg
305                 310                 315                 320 ggc ggc ccc ggg gcc cgc agg aga ggg gaa agg gtg tcc atg gcg gag     1307
Gly Gly Pro Gly Ala Arg Arg Arg Gly Glu Arg Val Ser Met Ala Glu
                325                 330                 335 gag acg gac cac ctc att ctc ctg gct atc atg acc atc acc ttc gcc     1355
Glu Thr Asp His Leu Ile Leu Leu Ala Ile Met Thr Ile Thr Phe Ala
            340                 345                 350 gtc tgc tcc ttg cct ttc acg att ttt gca tat atg aat gaa acc tct     1403
Val Cys Ser Leu Pro Phe Thr Ile Phe Ala Tyr Met Asn Glu Thr Ser
        355                 360                 365 tcc cga aag gaa aaa tgg gac ctc caa gct ctt agg ttt tta tca att     1451
Ser Arg Lys Glu Lys Trp Asp Leu Gln Ala Leu Arg Phe Leu Ser Ile
    370                 375                 380 aat tca ata att gac cct tgg gtc ttt gcc atc ctt agg cct cct gtt     1499
Asn Ser Ile Ile Asp Pro Trp Val Phe Ala Ile Leu Arg Pro Pro Val
385                 390                 395                 400 ctg aga cta atg cgt tca gtc ctc tgt tgt cgg att tca tta aga aca     1547
Leu Arg Leu Met Arg Ser Val Leu Cys Cys Arg Ile Ser Leu Arg Thr
                405                 410                 415 caa gat gca aca caa act tcc tgt tct aca cag tca gat gcc agt aaa     1595
Gln Asp Ala Thr Gln Thr Ser Cys Ser Thr Gln Ser Asp Ala Ser Lys
            420                 425                 430 cag gct gac ctt gcc tcg agc cac cac cac cac cac cac tct aga ctg     1643
Gln Ala Asp Leu Ala Ser Ser His His His His His His Ser Arg Leu
        435                 440                 445
```

```
                                                                         -continued gtg cca cgc gga tcc gtt cga gaa atc tac gag atg tat gaa gcg gtt        1691
Val Pro Arg Gly Ser Val Arg Glu Ile Tyr Glu Met Tyr Glu Ala Val
    450                 455                 460 agc atg cag ccg tca ctt aga agt gag tat gag tac cct gtt ttt tct        1739
Ser Met Gln Pro Ser Leu Arg Ser Glu Tyr Glu Tyr Pro Val Phe Ser
465                 470                 475                 480 cat gtt cag gca ggg atg ttc tca cct aag ctt aga acc ttt acc aaa        1787
His Val Gln Ala Gly Met Phe Ser Pro Lys Leu Arg Thr Phe Thr Lys
                485                 490                 495 ggt gat gcg gag aga tgg gta agc aca acc aaa aaa gcc agt gat tct        1835
Gly Asp Ala Glu Arg Trp Val Ser Thr Thr Lys Lys Ala Ser Asp Ser
            500                 505                 510 gca ttc tgg ctt gag gtt gaa ggt aat tcc atg acc gca cca aca ggc        1883
Ala Phe Trp Leu Glu Val Glu Gly Asn Ser Met Thr Ala Pro Thr Gly
        515                 520                 525 tcc aag cca agc ttt cct gac gga atg tta att ctc gtt gac cct gag        1931
Ser Lys Pro Ser Phe Pro Asp Gly Met Leu Ile Leu Val Asp Pro Glu
    530                 535                 540 cag gct gtt gag cca ggt gat ttc tgc ata gcc aga ctt ggg ggt gat        1979
Gln Ala Val Glu Pro Gly Asp Phe Cys Ile Ala Arg Leu Gly Gly Asp
545                 550                 555                 560 gag ttt acc ttc aag aaa ctg atc agg gat agc ggt cag gtg ttt tta        2027
Glu Phe Thr Phe Lys Lys Leu Ile Arg Asp Ser Gly Gln Val Phe Leu
                565                 570                 575 caa cca cta aac cca cag tac cca atg atc cca tgc aat gag agt tgt        2075
Gln Pro Leu Asn Pro Gln Tyr Pro Met Ile Pro Cys Asn Glu Ser Cys
            580                 585                 590 tcc gtt gtg ggg aaa gtt atc gct agt cag tgg cct gaa gag acg ttt        2123
Ser Val Val Gly Lys Val Ile Ala Ser Gln Trp Pro Glu Glu Thr Phe
        595                 600                 605 ggc tgatcggcaa ggtgttctgg tcggcgcata gctgataaca attgagcaag             2176
Gly aatcttcatc gaattagggg aattttcact cccctcagaa cataacatag taaatggatt      2236
gaattatgaa gaatggtttt tatgcgactt accgcagcaa aaataaaggg aaagataagc      2296
gctcaataaa cctgtctgtt ttccttaatt ctctgctggc tgataatcat cacctgcagg      2356
ttggctccaa ttatttgtat attcataaaa tcgataagct ttaatgcggt agtttatcac      2416
agttaaattg ctaacgcagt caggcaccgt gtatgaaatc taacaatgcg ctcatcgtca      2476
tcctcggcac cgtcaccctg gatgctgtag cataggcttt ggttatgccg gtactgccgg      2536
gcctcttgcg ggatcgacgc gaggctggat ggccttcccc attatgattc ttctcgcttc      2596
cggcggcatc gggatgcccg cgttgcaggc catgctgtcc aggcaggtag atgacgacca      2656
tcagggacag cttcaaggat cgctcgcggc tcttaccagc ctaacttcga tcactggacc      2716
gctgatcgtc acggcgattt atgccgcctc ggcgagcaca tggaacgggt tggcatggat      2776
tgtaggcgcc gccctatacc ttgtctgcct ccccgcgttg cgtcgcggtg catggagccg      2836
ggccacctcg acctgaatgg aagccggcgg cacctcgcta acggattcac cactccaaga      2896
attggagcca atcaattctt gcggagaact gtgaatgcgc aaaccaaccc ttggcagaac      2956
atatccatcg cgtccgccat ctccagcagc cgcacgcggc gcatctcggg cagcgttggg      3016
tcctggccac gggtgcgcat gatcgtgctc cgtcgttga ggacccggct aggctggcgg       3076
ggttgcctta ctggttagca gaatgaatca ccgatacgcg agcgaacgtg aagcgactgc      3136
tgctgcaaaa cgtctgcgac ctgagcaaca acatgaatgg tcttcggttt ccgtgtttcg      3196
taaagtctgg aaacgcggaa gtcagcgccc tgcaccatta tgttccggat ctgcatcgca      3256
```

```
ggatgctgct ggctaccctg tggaacacct acatctgtat taacgaagcg ctggcattga   3316
ccctgagtga ttttctctg gtcccgccgc atccataccg ccagttgttt accctcacaa    3376
cgttccagta accgggcatg ttcatcatca gtaacccgta tcgtgagcat cctctctcgt   3436
ttcatcggta tcattacccc catgaacaga aattccccct tacacggagg catcaagtga   3496
ccaaacagga aaaaccgcc cttaacatgg cccgctttat cagaagccag acattaacgc    3556
ttctggagaa actcaacgag ctggacgcgg atgaacaggc agacatctgt gaatcgcttc   3616
acgaccacgc tgatgagctt taccgcagct gcctcgcgcg tttcggtgat gacggtgaaa   3676
acctctgaca catgcagctc ccggagacgg tcacagcttg tctgtaagcg gatgccggga   3736
gcagacaagc ccgtcagggc gcgtcagcgg gtgttggcgg gtgtcgggc gcagccatga    3796
cccagtcacg tagcgatagc ggagtgtata ctggcttaac tatgcggcat cagagcagat   3856
tgtactgaga gtgcaccata tgcggtgtga ataccgcac agatgcgtaa ggagaaaata    3916
ccgcatcagg cgctcttccg cttcctcgct cactgactcg ctgcgctcgg tcgttcggct   3976
gcggcgagcg gtatcagctc actcaaaggc ggtaatacgg ttatccacag aatcagggga   4036
taacgcagga agaacatgt gagcaaaagg ccagcaaaag gccaggaacc gtaaaaaggc    4096
cgcgttgctg gcgttttcc ataggctccg ccccctgac gagcatcaca aaatcgacg     4156
ctcaagtcag aggtggcgaa acccgacagg actataaaga taccaggcgt ttccccctgg   4216
aagctccctc gtgcgctctc ctgttccgac cctgccgctt accggatacc tgtccgcctt   4276
tctcccttcg ggaagcgtgg cgctttctca tagctcacgc tgtaggtatc tcagttcggt   4336
gtaggtcgtt cgctccaagc tgggctgtgt gcacgaaccc cccgttcagc ccgaccgctg   4396
cgccttatcc ggtaactatc gtcttgagtc aacccggta agacacgact tatcgccact    4456
ggcagcagcc actggtaaca ggattagcag agcgaggtat gtaggcggtg ctacagagtt   4516
cttgaagtgg tggcctaact acggctacac tagaaggaca gtatttggta tctgcgctct   4576
gctgaagcca gttaccttcg gaaaagagt tggtagctct tgatccggca acaaaccac     4636
cgctggtagc ggtggttttt ttgtttgcaa gcagcagatt acgcgcagaa aaaaggatc    4696
tcaagaagat cctttgatct tttctacggg gtctgacgct cagtggaacg aaaactcacg   4756
ttaagggatt ttggtcatga gattatcaaa aaggatcttc acctagatcc tttttaccccg   4816
gttgataatc agaaaagccc caaaacagg aagattgtat aagcaaatat ttaaattgta    4876
aacgttaata ttttgttaaa attcgcgtta aatttttgtt aaatcagctc atttttaac    4936
caataggccg aaatcggcaa aatcccttat aaatcaaag aatagccga gatagggttg    4996
agtgttgttc cagtttggaa caagagtcca ctattaaaga acgtggactc caacgtcaaa   5056
gggcgaaaaa ccgtctatca gggcgatggc ccactacgtg aaccatcacc caaatcaagt   5116
ttttggggt cgaggtgccg taaagcacta atcggaacc ctaaagggag ccccgatt      5176
agagcttgac ggggaaagcc ggcgaacgtg gcgagaagg aagggaagaa agcgaaagga    5236
gcgggcgcta gggcgctggc aagtgtagcg gtcacgctgc gcgtaaccac cacccgcc    5296
gcgcttaatg cgccgctaca gggcgcgtaa atcaatctaa agtatatg agtaaacttg     5356
gtctgacagt taccaatgct taatcagtga ggcacctatc tcagcgatct gtctatttcg   5416
ttcatccata gttgcctgac tccccgtcgt gtagataact acgatacggg agggcttacc    5476
atctggcccc agtgctgcaa tgataccgcg agacccacgc tcaccggctc agatttatc    5536
agcaataaac cagccagccg gaagggccga gcgcagaagt ggtcctgcaa ctttatccgc   5596
ctccatccag tctattaatt gttgccggga agctagagta agtagttcgc cagttaatag   5656
```

-continued

```
tttgcgcaac gttgttgcca ttgctgcagg catcgtggtg tcacgctcgt cgtttggtat    5716
ggcttcattc agctccggtt cccaacgatc aaggcgagtt acatgatccc ccatgttgtg    5776
caaaaaagcg gttagctcct tcggtcctcc gatcgttgtc agaagtaagt tggccgcagt    5836
gttatcactc atggttatgg cagcactgca taattctctt actgtcatgc catccgtaag    5896
atgcttttct gtgactggtg agtactcaac caagtcattc tgagaatagt gtatgcggcg    5956
accgagttgc tcttgcccgg cgtcaacacg ggataatacc gcgccacata gcagaacttt    6016
aaaagtgctc atcattggaa aacgttcttc ggggcgaaaa ctctcaagga tcttaccgct    6076
gttgagatcc agttcgatgt aacccactcg tgcacccaac tgatcttcag catcttttac    6136
tttcaccagc gtttctgggt gagcaaaaac aggaaggcaa aatgccgcaa aaagggaat    6196 aagggcgaca cggaaatgtt gaatactcat actcttcctt tttcaatatt attgaagcat    6256
ttatcagggt tattgtctca tgagcggata catatttgaa tgtatttaga aaataaaca    6316 aatagggggtt ccgcgcacat ttccccgaaa agtgccacct gacgtctaag aaaccattat    6376
tatcatgaca ttaacctata aaaataggcg tatcacgagg ccctttcgtc ttcaagaatt    6436
gatcgatcaa                                                            6446
```

<210> SEQ ID NO 3
<211> LENGTH: 5674
<212> TYPE: DNA
<213> ORGANISM: Artificial Sequence
<220> FEATURE:
<221> NAME/KEY: CDS
<222> LOCATION: (300)...(1616)
<223> OTHER INFORMATION: Description of Artificial Sequence:/note = synthetic construct

<400> SEQUENCE: 3

```
ttctcatgtt tgacagctta tctcatcgac tgcacggtgc accaatgctt ctggcgtcag     60
gcagccatcg gaagctgtgg tatggctgtg caggtcgtaa atcactgcat aattcgtgtc    120
gctcaaggcg cactcccgtt ctggataatg tttttttgcgc cgacatcata acggttctgg    180
caaatattct gaaatgagct gttgacaatt aatcatcggc tcgtataatg tggaattgtg    240
agcggataac aattaatgtg tgaatgtgag cggataacaat ttcacacagg aaacagcgt    299
```

```
atg agc aca aaa aag aaa cca tta aca caa gag cag ctt gag gac gca      347
Met Ser Thr Lys Lys Lys Pro Leu Thr Gln Glu Gln Leu Glu Asp Ala
 1               5                  10                  15 cgt cgc ctt aaa gca att tat gaa aaa aag aaa aat gaa ctt ggc tta      395
Arg Arg Leu Lys Ala Ile Tyr Glu Lys Lys Lys Asn Glu Leu Gly Leu
            20                  25                  30 tcc cag gaa tct gtc gca gac aag atg ggg atg ggg cag tca ggc gtt      443
Ser Gln Glu Ser Val Ala Asp Lys Met Gly Met Gly Gln Ser Gly Val
        35                  40                  45 ggt gct tta ttt aat ggc atc aat gca tta aat gct tat aac gcg gca      491
Gly Ala Leu Phe Asn Gly Ile Asn Ala Leu Asn Ala Tyr Asn Ala Ala
    50                  55                  60 ttg cta gca aaa att ctc aaa gtt agc gtt gaa gaa ttc cat atg gat      539
Leu Leu Ala Lys Ile Leu Lys Val Ser Val Glu Glu Phe His Met Asp
65                  70                  75                  80 tat caa gtg tca agt cca atc tat gac atc aat tat tat aca tcg gag      587
Tyr Gln Val Ser Ser Pro Ile Tyr Asp Ile Asn Tyr Tyr Thr Ser Glu
                85                  90                  95 ccc tgc caa aaa atc aat gtg aag caa atc gca gcc cgc ctc ctg cct      635
Pro Cys Gln Lys Ile Asn Val Lys Gln Ile Ala Ala Arg Leu Leu Pro
            100                 105                 110
```

-continued

| | |
|---|---|
| ccg ctc tac tca ctg gtg ttc atc ttt ggt ttt gtg ggc aac atg ctg<br>Pro Leu Tyr Ser Leu Val Phe Ile Phe Gly Phe Val Gly Asn Met Leu<br>115                    120                 125 | 683 |
| gtc atc ctc atc ctg ata aac tgc aaa agg ctg aag agc atg act gac<br>Val Ile Leu Ile Leu Ile Asn Cys Lys Arg Leu Lys Ser Met Thr Asp<br>130                    135                 140 | 731 |
| atc tac ctg ctc aac ctg gcc atc tct gac ctg ttt ttc ctt ctt act<br>Ile Tyr Leu Leu Asn Leu Ala Ile Ser Asp Leu Phe Phe Leu Leu Thr<br>145                    150               155                 160 | 779 |
| gtc ccc ttc tgg gct cac tat gct gcc gcc cag tgg gac ttt gga aat<br>Val Pro Phe Trp Ala His Tyr Ala Ala Ala Gln Trp Asp Phe Gly Asn<br>               165               170                 175 | 827 |
| aca atg tgt caa ctc ttg aca ggg ctc tat ttt ata ggc ttc ttc tct<br>Thr Met Cys Gln Leu Leu Thr Gly Leu Tyr Phe Ile Gly Phe Phe Ser<br>               180               185                 190 | 875 |
| gga atc ttc ttc atc atc ctc ctg aca atc gat agg tac ctg gct gtc<br>Gly Ile Phe Phe Ile Ile Leu Leu Thr Ile Asp Arg Tyr Leu Ala Val<br>               195               200                 205 | 923 |
| gtc cat gct gtg ttt gct tta aaa gcc agg acg gtc acc ttt ggg gtg<br>Val His Ala Val Phe Ala Leu Lys Ala Arg Thr Val Thr Phe Gly Val<br>210                    215                 220 | 971 |
| gtg aca agt gtg atc act tgg gtg gtg gct gtg ttt gcg tct ctc cca<br>Val Thr Ser Val Ile Thr Trp Val Val Ala Val Phe Ala Ser Leu Pro<br>225                    230               235                 240 | 1019 |
| gga atc atc ttt acc aga tct caa aaa gaa ggt ctt cat tac acc tgc<br>Gly Ile Ile Phe Thr Arg Ser Gln Lys Glu Gly Leu His Tyr Thr Cys<br>               245               250                 255 | 1067 |
| agc tct cat ttt cca tac agt cag tat caa ttc tgg aag aat ttc cag<br>Ser Ser His Phe Pro Tyr Ser Gln Tyr Gln Phe Trp Lys Asn Phe Gln<br>               260               265                 270 | 1115 |
| aca tta aag ata gtc atc ttg ggg ctg gtc ctg ccg ctg ctt gtc atg<br>Thr Leu Lys Ile Val Ile Leu Gly Leu Val Leu Pro Leu Leu Val Met<br>275                    280               285 | 1163 |
| gtc atc tgc tac tcg gga atc cta aaa act ctg ctt cgg tgt cga aat<br>Val Ile Cys Tyr Ser Gly Ile Leu Lys Thr Leu Leu Arg Cys Arg Asn<br>290                    295               300 | 1211 |
| gag aag aag agg cac agg gct gtg agg ctt atc ttc acc atc atg att<br>Glu Lys Lys Arg His Arg Ala Val Arg Leu Ile Phe Thr Ile Met Ile<br>305                    310               315                 320 | 1259 |
| gtt tat ttt ctc ttc tgg gct ccc tac aac att gtc ctt ctc ctg aac<br>Val Tyr Phe Leu Phe Trp Ala Pro Tyr Asn Ile Val Leu Leu Leu Asn<br>               325               330                 335 | 1307 |
| acc ttc cag gaa ttc ttt ggc ctg aat aat tgc agt agc tct aac agg<br>Thr Phe Gln Glu Phe Phe Gly Leu Asn Asn Cys Ser Ser Ser Asn Arg<br>               340               345                 350 | 1355 |
| ttg gac caa gct atg cag gtg aca gag act ctt ggg atg acg cac tgc<br>Leu Asp Gln Ala Met Gln Val Thr Glu Thr Leu Gly Met Thr His Cys<br>355                    360               365 | 1403 |
| tgc atc aac ccc atc atc tat gcc ttt gtc ggg gag aag ttc aga aac<br>Cys Ile Asn Pro Ile Ile Tyr Ala Phe Val Gly Glu Lys Phe Arg Asn<br>370                    375               380 | 1451 |
| tac ctc tta gtc ttc ttc caa aag cac att gcc aaa cgc ttc tgc aaa<br>Tyr Leu Leu Val Phe Phe Gln Lys His Ile Ala Lys Arg Phe Cys Lys<br>385                    390               395                 400 | 1499 |
| tgc tgt tct att ttc cag caa gag gct ccc gag cga gca agc tca gtt<br>Cys Cys Ser Ile Phe Gln Gln Glu Ala Pro Glu Arg Ala Ser Ser Val<br>               405               410                 415 | 1547 |
| tac acc cga tcc act ggg gag cag gaa ata tct gtg ggc ttg gcc tcg<br>Tyr Thr Arg Ser Thr Gly Glu Gln Glu Ile Ser Val Gly Leu Ala Ser | 1595 |

|     |     |     |     | 420 |     |     |     | 425 |     |     | 430 |     |     |      |
|-----|-----|-----|-----|-----|-----|-----|-----|-----|-----|-----|-----|-----|-----|------|
| agg | cac | cat | cac | cac | cac | cac | tgaaagcttt | aatgcggtag | tttatcacag |     |     |     |     | 1646 |
| Arg | His | His | His | His | His | His |     |     |     |     |     |     |     |      |
|     |     |     |     | 435 |     |     |     |     |     |     |     |     |     |      |

```
ttaaattgct aacgcagtca ggcaccgtgt atgaaatcta caatgcgct catcgtcatc    1706 ctcggcaccg tcaccctgga tgctgtaggc ataggcttgg ttatgccggt actgccgggc    1766
ctcttgcggg atcgacgcga ggctggatgg ccttccccat tatgattctt ctcgcttccg    1826
gcggcatcgg gatgcccgcg ttgcaggcca tgctgtccag gcaggtagat gacgaccatc    1886
agggacagct tcaaggatcg ctcgcggctc ttaccagcct aacttcgatc actggaccgc    1946
tgatcgtcac ggcgatttat gccgcctcgg cgagcacatg gaacggggttg catggattg    2006 taggcgccgc cctataccct gtctgcctcc ccgcgttgcg tcgcggtgca tggagccggg    2066
ccacctcgac ctgaatggaa gccggcggca cctcgctaac ggattcacca ctccaagaat    2126
tggagccaat caattcttgc ggagaactgt gaatgcgcaa accaaccctt ggcagaacat    2186
atccatcgcg tccgccatct ccagcagccg cacgcggcgc atctcgggca gcgttgggtc    2246
ctggccacgg gtgcgcatga tcgtgctcct gtcgttgagg acccggctag ctggcgggg    2306 ttgccttact ggttagcaga atgaatcacc gatacgcgag cgaacgtgaa gcgactgctg    2366
ctgcaaaacg tctgcgacct gagcaacaac atgaatggtc ttcggttttcc gtgtttcgta    2426 aagtctggaa acgcggaagt cagcgccctg caccattatg ttccggatct gcatcgcagg    2486
atgctgctgg ctaccctgtg gaacacctac atctgtatta cgaagcgct ggcattgacc    2546 ctgagtgatt tttctctggt cccgccgcat ccataccgcc agttgtttac cctcacaacg    2606
ttccagtaac cgggcatgtt catcatcagt aacccgtatc gtgagcatcc tctctcgttt    2666
catcggtatc attcccccca tgaacagaaa ttccccctta cacggaggca tcaagtgacc    2726
aaacaggaaa aaaccgccct taacatggcc cgctttatca gaagccagac attaacgctt    2786
ctggagaaac tcaacgagct ggacgcggat gaacaggcag acatctgtga atcgcttcac    2846
gaccacgctg atgagcttta ccgcagctgc ctcgcgcgtt tcggtgatga cggtgaaaac    2906
ctctgacaca tgcagctccc ggagacggtc acagcttgtc tgtaagcgga tgccgggagc    2966
agacaagccc gtcagggcgc gtcagcgggt gttggcgggt gtcggggcgc agccatgacc    3026
cagtcacgta gcgatagcgg agtgtatact ggcttaacta tgcggcatca gagcagattg    3086
tactgagagt gcaccatatg cggtgtgaaa taccgcacag atgcgtaagg agaaaatacc    3146
gcatcaggcg ctcttccgct tcctcgctca ctgactcgct gcgctcggtc gttcggctgc    3206
ggcgagcggt atcagctcac tcaaaggcgg taatacggtt atccacagaa tcaggggata    3266
acgcaggaaa gaacatgtga gcaaaaggcc agcaaaaggc caggaaccgt aaaaaggccg    3326
cgttgctggc gtttttccat aggctccgcc cccctgacga gcatcacaaa atcgacgct    3386 caagtcagag gtggcgaaac ccgacaggac tataaagata ccaggcgttt ccccctggaa    3446
gctccctcgt gcgctctcct gttccgaccc tgccgcttac cggatacctg tccgcctttc    3506
tcccttcggg aagcgtggcg ctttctcata gctcacgctg taggtatctc agttcggtgt    3566
aggtcgttcg ctccaagctg ggctgtgtgc acgaaccccc cgttcagccc gaccgctgcg    3626
ccttatccgg taactatcgt cttgagtcca acccggtaag acacgactta tcgccactgg    3686
cagcagccac tggtaacagg attagcagag cgaggtatgt aggcggtgct acagagttct    3746
tgaagtggtg gcctaactac ggctacacta agaggacagt atttggtatc tgcgctctgc    3806
tgaagccagt taccttcgga aaaagagttg gtagctcttg atccggcaaa caaaccaccg    3866
```

-continued

```
ctggtagcgg tggttttttt gtttgcaagc agcagattac gcgcagaaaa aaaggatctc    3926
aagaagatcc tttgatcttt tctacgggt ctgacgctca gtggaacgaa aactcacgtt    3986
aagggatttt ggtcatgaga ttatcaaaaa ggatcttcac ctagatcctt ttaccccggt    4046
tgataatcag aaaagcccca aaaacaggaa gattgtataa gcaaatattt aaattgtaaa    4106
cgttaatatt tgttaaaat tcgcgttaaa tttttgttaa atcagctcat tttttaacca    4166
ataggccgaa atcggcaaaa tcccttataa atcaaaagaa tagcccgaga tagggttgag    4226
tgttgttcca gtttggaaca agagtccact attaaagaac gtggactcca acgtcaaagg    4286
gcgaaaaacc gtctatcagg gcgatggccc actacgtgaa ccatcaccca atcaagtttt    4346
tttgggtgcg aggtgccgta aagcactaaa tcggaaccct aaagggagcc ccgatttag    4406 agcttgacgg ggaaagccgg cgaacgtggc gagaaaggaa gggaagaaag cgaaaggagc    4466
gggcgctagg gcgctggcaa gtgtagcggt cacgctgcgc gtaaccacca cacccgccgc    4526
gcttaatgcg ccgctacagg gcgcgtaaat caatctaaag tatatatgag taaacttggt    4586
ctgacagtta ccaatgctta atcagtgagg cacctatctc agcgatctgt ctatttcgtt    4646
catccatagt tgcctgactc cccgtcgtgt agataactac gatacgggag ggcttaccat    4706
ctggccccag tgctgcaatg ataccgcgag acccacgctc accggctcca gatttatcag    4766
caataaacca gccagccgga aggggccgagc gcagaagtgg tcctgcaact ttatccgcct    4826
ccatccagtc tattaattgt tgccgggaag ctagagtaag tagttcgcca gttaatagtt    4886
tgcgcaacgt tgttgccatt gctgcaggca tcgtggtgtc acgctcgtcg tttggtatgg    4946
cttcattcag ctccggttcc caacgatcaa ggcgagttac atgatccccc atgttgtgca    5006
aaaaagcggt tagctccttc ggtcctccga tcgttgtcag aagtaagttg gccgcagtgt    5066
tatcactcat ggttatggca gcactgcata attctcttac tgtcatgcca tccgtaagat    5126
gcttttctgt gactggtgag tactcaacca agtcattctg agaatagtgt atgcggcgac    5186
cgagttgctc ttgcccggcg tcaacacggg ataataccgc gccacatagc agaactttaa    5246
aagtgctcat cattggaaaa cgttcttcgg ggcgaaaact ctcaaggatc ttaccgctgt    5306
tgagatccag ttcgatgtaa cccactcgtg cacccaactg atcttcagca tcttttactt    5366
tcaccagcgt ttctgggtga gcaaaaacag gaaggcaaaa tgccgcaaaa agggaataa    5426 gggcgacacg gaaatgttga atactcatac tcttcctttt tcaatattat tgaagcattt    5486
atcagggtta ttgtctcatg agcggataca tatttgaatg tatttagaaa aataaacaaa    5546 tagggttcc gcgcacattt ccccgaaaag tgccacctga cgtctaagaa accattatta    5606
tcatgacatt aacctataaa aataggcgta tcacgaggcc ctttcgtctt caagaattga    5666
tcgatcaa                                                              5674
```

<210> SEQ ID NO 4
<211> LENGTH: 5857
<212> TYPE: DNA
<213> ORGANISM: Artificial Sequence
<220> FEATURE:
<221> NAME/KEY: CDS
<222> LOCATION: (300)...(1799)
<223> OTHER INFORMATION: Description of Artificial Sequence:/note = synthetic construct

<400> SEQUENCE: 4

```
ttctcatgtt tgacagctta tctcatcgac tgcacggtgc accaatgctt ctggcgtcag      60
gcagccatcg gaagctgtgg tatggctgtg caggtcgtaa atcactgcat aattcgtgtc     120
```

-continued

```
gctcaaggcg cactcccgtt ctggataatg ttttttgcgc cgacatcata acggttctgg       180
caaatattct gaaatgagct gttgacaatt aatcatcggc tcgtataatg tggaattgtg       240
agcggataac aattaatgtg tgaatgtgag cggatacaat ttcacacagg aaacagcgt        299
```

| | | | | | | | | | | | | | | | | |
|---|---|---|---|---|---|---|---|---|---|---|---|---|---|---|---|---|
| atg | agc | aca | aaa | aag | aaa | cca | tta | aca | caa | gag | cag | ctt | gag | gac | gca | 347 |
| Met | Ser | Thr | Lys | Lys | Lys | Pro | Leu | Thr | Gln | Glu | Gln | Leu | Glu | Asp | Ala | |
| 1 | | | | 5 | | | | | 10 | | | | | 15 | | |
| cgt | cgc | ctt | aaa | gca | att | tat | gaa | aaa | aag | aaa | aat | gaa | ctt | ggc | tta | 395 |
| Arg | Arg | Leu | Lys | Ala | Ile | Tyr | Glu | Lys | Lys | Lys | Asn | Glu | Leu | Gly | Leu | |
| | | | 20 | | | | | 25 | | | | | 30 | | | |
| tcc | cag | gaa | tct | gtc | gca | gac | aag | atg | ggg | atg | ggg | cag | tca | ggc | gtt | 443 |
| Ser | Gln | Glu | Ser | Val | Ala | Asp | Lys | Met | Gly | Met | Gly | Gln | Ser | Gly | Val | |
| | | 35 | | | | | 40 | | | | | 45 | | | | |
| ggt | gct | tta | ttt | aat | ggc | atc | aat | gca | tta | aat | gct | tat | aac | gcg | gca | 491 |
| Gly | Ala | Leu | Phe | Asn | Gly | Ile | Asn | Ala | Leu | Asn | Ala | Tyr | Asn | Ala | Ala | |
| | 50 | | | | | 55 | | | | | 60 | | | | | |
| ttg | cta | gca | aaa | att | ctc | aaa | gtt | agc | gtt | gaa | gaa | ttc | acc | atg | ggg | 539 |
| Leu | Leu | Ala | Lys | Ile | Leu | Lys | Val | Ser | Val | Glu | Glu | Phe | Thr | Met | Gly | |
| 65 | | | | | 70 | | | | | 75 | | | | | 80 | |
| caa | ccc | ggg | aac | ggc | agc | gcc | ttc | ttg | ctg | gca | ccc | aat | gga | agc | cat | 587 |
| Gln | Pro | Gly | Asn | Gly | Ser | Ala | Phe | Leu | Leu | Ala | Pro | Asn | Gly | Ser | His | |
| | | | | 85 | | | | | 90 | | | | | 95 | | |
| gcg | ccg | gac | cac | gac | gtc | acg | cag | caa | agg | gac | gag | gtg | tgg | gtg | gtg | 635 |
| Ala | Pro | Asp | His | Asp | Val | Thr | Gln | Gln | Arg | Asp | Glu | Val | Trp | Val | Val | |
| | | | 100 | | | | | 105 | | | | | 110 | | | |
| ggc | atg | ggc | atc | gtc | atg | tct | ctc | atc | gtc | ctg | gcc | atc | gtg | ttt | ggc | 683 |
| Gly | Met | Gly | Ile | Val | Met | Ser | Leu | Ile | Val | Leu | Ala | Ile | Val | Phe | Gly | |
| | | 115 | | | | | 120 | | | | | 125 | | | | |
| aat | gtg | ctg | gtc | atc | aca | gcc | att | gcc | aag | ttc | gag | cgt | ctg | cag | acg | 731 |
| Asn | Val | Leu | Val | Ile | Thr | Ala | Ile | Ala | Lys | Phe | Glu | Arg | Leu | Gln | Thr | |
| | 130 | | | | | 135 | | | | | 140 | | | | | |
| gtc | acc | aac | tac | ttc | atc | aca | agc | ttg | gcc | tgt | gct | gat | ctg | gtc | atg | 779 |
| Val | Thr | Asn | Tyr | Phe | Ile | Thr | Ser | Leu | Ala | Cys | Ala | Asp | Leu | Val | Met | |
| 145 | | | | | 150 | | | | | 155 | | | | | 160 | |
| ggg | cta | gca | gtg | gtg | ccc | ttt | ggg | gcc | gcc | cat | att | ctc | atg | aaa | atg | 827 |
| Gly | Leu | Ala | Val | Val | Pro | Phe | Gly | Ala | Ala | His | Ile | Leu | Met | Lys | Met | |
| | | | | 165 | | | | | 170 | | | | | 175 | | |
| tgg | act | ttt | ggc | aac | ttc | tgg | tgc | gaa | ttc | tgg | act | tcc | att | gat | gtg | 875 |
| Trp | Thr | Phe | Gly | Asn | Phe | Trp | Cys | Glu | Phe | Trp | Thr | Ser | Ile | Asp | Val | |
| | | | 180 | | | | | 185 | | | | | 190 | | | |
| ctg | tgc | gtc | acg | gca | tcg | att | gag | acc | ctg | tgc | gtg | atc | gca | gtc | gac | 923 |
| Leu | Cys | Val | Thr | Ala | Ser | Ile | Glu | Thr | Leu | Cys | Val | Ile | Ala | Val | Asp | |
| | | 195 | | | | | 200 | | | | | 205 | | | | |
| cgc | tac | ttt | gcc | att | act | agt | cct | ttc | aag | tac | cag | agc | ctg | ctg | acc | 971 |
| Arg | Tyr | Phe | Ala | Ile | Thr | Ser | Pro | Phe | Lys | Tyr | Gln | Ser | Leu | Leu | Thr | |
| | 210 | | | | | 215 | | | | | 220 | | | | | |
| aag | aat | aag | gcc | cgg | gtg | atc | att | ctg | atg | gtg | tgg | att | gtg | tca | ggc | 1019 |
| Lys | Asn | Lys | Ala | Arg | Val | Ile | Ile | Leu | Met | Val | Trp | Ile | Val | Ser | Gly | |
| 225 | | | | | 230 | | | | | 235 | | | | | 240 | |
| ctt | acc | tcc | ttc | ttg | ccc | att | cag | atg | cac | tgg | tac | agg | gcc | acc | cac | 1067 |
| Leu | Thr | Ser | Phe | Leu | Pro | Ile | Gln | Met | His | Trp | Tyr | Arg | Ala | Thr | His | |
| | | | | 245 | | | | | 250 | | | | | 255 | | |
| cag | gaa | gcc | atc | aac | tgc | tat | gcc | aat | gag | acc | tgc | tgt | gac | ttc | ttc | 1115 |
| Gln | Glu | Ala | Ile | Asn | Cys | Tyr | Ala | Asn | Glu | Thr | Cys | Cys | Asp | Phe | Phe | |
| | | | 260 | | | | | 265 | | | | | 270 | | | |
| acg | aac | caa | gcc | tat | gcc | att | gcc | tct | tcc | atc | gtg | tcc | ttc | tac | gtt | 1163 |
| Thr | Asn | Gln | Ala | Tyr | Ala | Ile | Ala | Ser | Ser | Ile | Val | Ser | Phe | Tyr | Val | |
| | | 275 | | | | | 280 | | | | | 285 | | | | |
| ccc | ctg | gtg | atc | atg | gtc | ttc | gtc | tac | tcc | agg | gtc | ttt | cag | gag | gcc | 1211 |

```
                                               -continued

Pro Leu Val Ile Met Val Phe Val Tyr Ser Arg Val Phe Gln Glu Ala
        290                 295                 300 aaa agg cag ctc cag aag att gac aaa tct gag ggc cgc ttc cat gtc    1259
Lys Arg Gln Leu Gln Lys Ile Asp Lys Ser Glu Gly Arg Phe His Val
305                 310                 315                 320 cag aac ctt agc cag gtg gag cag gat ggg cgg acg ggg cat gga ctc    1307
Gln Asn Leu Ser Gln Val Glu Gln Asp Gly Arg Thr Gly His Gly Leu
                325                 330                 335 cgc aga tct tcc aag ttc tgc ttg aag gag cac aaa gcc ctc aag acg    1355
Arg Arg Ser Ser Lys Phe Cys Leu Lys Glu His Lys Ala Leu Lys Thr
            340                 345                 350 tta ggc atc atc atg ggc act ttc acc ctc tgc tgg ctg ccc ttc ttc    1403
Leu Gly Ile Ile Met Gly Thr Phe Thr Leu Cys Trp Leu Pro Phe Phe
        355                 360                 365 atc gtt aac att gtg cat gtg atc cag gat aac ctc atc cgt aag gaa    1451
Ile Val Asn Ile Val His Val Ile Gln Asp Asn Leu Ile Arg Lys Glu
    370                 375                 380 gtt tac atc ctc cta aat tgg ata ggc tat gtc aat tct ggt ttc aat    1499
Val Tyr Ile Leu Leu Asn Trp Ile Gly Tyr Val Asn Ser Gly Phe Asn
385                 390                 395                 400 ccc ctt atc tac tgc cgg agc cca gat ttc agg att gcc ttc cag gag    1547
Pro Leu Ile Tyr Cys Arg Ser Pro Asp Phe Arg Ile Ala Phe Gln Glu
                405                 410                 415 ctt ctg tgc ctg cgc agg tct tct ttg aag gcc tat ggc aat ggc tac    1595
Leu Leu Cys Leu Arg Arg Ser Ser Leu Lys Ala Tyr Gly Asn Gly Tyr
            420                 425                 430 tcc agc aac ggc aac aca ggg gag cag agt gga tat cac gtg gaa cag    1643
Ser Ser Asn Gly Asn Thr Gly Glu Gln Ser Gly Tyr His Val Glu Gln
        435                 440                 445 gag aaa gaa aat aaa ctg ctg tgt gaa gac ctc cca ggc acg gaa gac    1691
Glu Lys Glu Asn Lys Leu Leu Cys Glu Asp Leu Pro Gly Thr Glu Asp
    450                 455                 460 ttt gtg ggc cat caa ggt act gtg cct agc gat aac att gat tca caa    1739
Phe Val Gly His Gln Gly Thr Val Pro Ser Asp Asn Ile Asp Ser Gln
465                 470                 475                 480 ggg agg aat tgt agt aca aat gac tca ctg cta gcc tcg agg cac cat    1787
Gly Arg Asn Cys Ser Thr Asn Asp Ser Leu Leu Ala Ser Arg His His
                485                 490                 495 cac cac cac cac tgaaagcttt aatgcggtag tttatcacag ttaaattgct        1839
His His His His
        500 aacgcagtca ggcaccgtgt atgaaatcta acaatgcgct catcgtcatc ctcggcaccg   1899 tcaccctgga tgctgtaggc ataggcttgg ttatgccggt actgccgggc ctcttgcggg   1959 atcgacgcga ggctggatgg ccttccccat tatgattctt ctcgcttccg gcggcatcgg   2019 gatgcccgcg ttgcaggcca tgctgtccag gcaggtagat gacgaccatc agggacagct   2079 tcaaggatcg ctcgcggctc ttaccagcct aacttcgatc actggaccgc tgatcgtcac   2139 ggcgatttat gccgcctcgg cgagcacatg gaacgggttg gcatggattg taggcgccgc   2199 cctataccct gtctgcctcc ccgcgttgcg tcgcggtgca tggagccggg ccacctcgac   2259 ctgaatggaa gccggcggca cctcgctaac ggattcacca ctccaagaat ggagccaat    2319 caattcttgc ggagaactgt gaatgcgcaa accaaccctt ggcagaacat atccatcgcg   2379 tccgccatct ccagcagccg cacgcggcgc atctcgggca gcgttgggtc ctggccacgg   2439 gtgcgcatga tcgtgctcct gtcgttgagg acccggctag gctggcgggg ttgccttact   2499 ggttagcaga atgaatcacc gatacgcgag cgaacgtgaa gcgactgctg ctgcaaaacg   2559
```

```
tctgcgacct gagcaacaac atgaatggtc ttcggtttcc gtgtttcgta aagtctggaa    2619
acgcggaagt cagcgccctg caccattatg ttccggatct gcatcgcagg atgctgctgg    2679
ctaccctgtg gaacacctac atctgtatta acgaagcgct ggcattgacc ctgagtgatt    2739
tttctctggt cccgccgcat ccataccgcc agttgtttac cctcacaacg ttccagtaac    2799
cgggcatgtt catcatcagt aacccgtatc gtgagcatcc tctctcgttt catcggtatc    2859
attaccccca tgaacagaaa ttcccccctta cacggaggca tcaagtgacc aaacaggaaa    2919
aaaccgccct taacatggcc cgctttatca gaagccagac attaacgctt ctggagaaac    2979
tcaacgagct ggacgcggat gaacaggcag acatctgtga atcgcttcac gaccacgctg    3039
atgagcttta ccgcagctgc ctcgcgcgtt tcggtgatga cggtgaaaac ctctgacaca    3099
tgcagctccc ggagacggtc acagcttgtc tgtaagcgga tgccgggagc agacaagccc    3159
gtcagggcgc gtcagcgggt gttggcgggt gtcggggcgc agccatgacc cagtcacgta    3219
gcgatagcgg agtgtatact ggcttaacta tgcggcatca gagcagattg tactgagagt    3279
gcaccatatg cggtgtgaaa taccgcacag atgcgtaagg agaaaatacc gcatcaggcg    3339
ctcttccgct tcctcgctca ctgactcgct gcgctcggtc gttcggctgc ggcgagcggt    3399
atcagctcac tcaaaggcgg taatacggtt atccacagaa tcaggggata acgcaggaaa    3459
gaacatgtga gcaaaaggcc agcaaaaggc caggaaccgt aaaaaggccg cgttgctggc    3519
gtttttccat aggctccgcc cccctgacga gcatcacaaa aatcgacgct caagtcagag    3579
gtggcgaaac ccgacaggac tataaagata ccaggcgttt ccccctggaa gctccctcgt    3639
gcgctctcct gttccgaccc tgccgcttac cggatacctg tccgcctttc tcccttcggg    3699
aagcgtggcg ctttctcata gctcacgctg taggtatctc agttcggtgt aggtcgttcg    3759
ctccaagctg ggctgtgtgc acgaaccccc cgttcagccc gaccgctgcg ccttatccgg    3819
taactatcgt cttgagtcca acccggtaag acacgactta tcgccactgg cagcagccac    3879
tggtaacagg attagcagag cgaggtatgt aggcggtgct acagagttct tgaagtggtg    3939
gcctaactac ggctacacta aggacagt atttggtatc tgcgctctgc tgaagccagt    3999
taccttcgga aaagagttg gtagctcttg atccggcaaa caaaccaccg ctggtagcgg    4059
tggttttttt gtttgcaagc agcagattac gcgcagaaaa aaggatctc aagaagatcc    4119 tttgatcttt tctacggggt ctgacgctca gtggaacgaa aactcacgtt aagggatttt    4179
ggtcatgaga ttatcaaaaa ggatcttcac ctagatcctt ttaccccggt tgataatcag    4239
aaaagcccca aaacaggaa gattgtataa gcaaatattt aaattgtaaa cgttaatatt    4299
ttgttaaaat tcgcgttaaa ttttttgtta atcagctcat tttttaacca ataggccgaa    4359
atcggcaaaa tcccttataa atcaaaagaa tagcccgaga taggttgag tgttgttcca    4419 gtttggaaca agagtccact attaaagaac gtggactcca acgtcaaagg gcgaaaaacc    4479
gtctatcagg gcgatggccc actacgtgaa ccatcaccca aatcaagttt ttgggggtcg    4539
aggtgccgta aagcactaaa tcggaaccct aaagggagcc ccgatttag agcttgacgg    4599 ggaaagccgg cgaacgtggc gagaaaggaa gggaagaaag cgaaaggagc gggcgctagg    4659
gcgctggcaa gtgtagcggt cacgctgcgc gtaaccacca cacccgccgc gcttaatgcg    4719
ccgctacagg gcgcgtaaat caatctaaag tatatatgag taaacttggt ctgacagtta    4779
ccaatgctta atcagtgagg cacctatctc agcgatctgt ctatttcgtt catccatagt    4839
tgcctgactc cccgtcgtgt agataactac gatacgggag ggcttaccat ctggccccag    4899
tgctgcaatg ataccgcgag acccacgctc accggctcca gatttatcag caataaacca    4959
```

-continued

```
gccagccgga aggccgagc gcagaagtgg tcctgcaact ttatccgcct ccatccagtc      5019
tattaattgt tgccgggaag ctagagtaag tagttcgcca gttaatagtt tgcgcaacgt      5079
tgttgccatt gctgcaggca tcgtggtgtc acgctcgtcg tttggtatgg cttcattcag      5139
ctccggttcc caacgatcaa ggcgagttac atgatccccc atgttgtgca aaaaagcggt      5199
tagctccttc ggtcctccga tcgttgtcag aagtaagttg gccgcagtgt tatcactcat      5259
ggttatggca gcactgcata attctcttac tgtcatgcca tccgtaagat gcttttctgt      5319
gactggtgag tactcaacca agtcattctg agaatagtgt atgcggcgac cgagttgctc      5379
ttgcccggcg tcaacacggg ataataccgc gccacatagc agaactttaa aagtgctcat      5439
cattggaaaa cgttcttcgg ggcgaaaact ctcaaggatc ttaccgctgt tgagatccag      5499
ttcgatgtaa cccactcgtg cacccaactg atcttcagca tcttttactt tcaccagcgt      5559
ttctgggtga gcaaaaacag gaaggcaaaa tgccgcaaaa aagggaataa gggcgacacg      5619
gaaatgttga atactcatac tcttcctttt tcaatattat tgaagcattt atcagggtta      5679
ttgtctcatg agcggataca tatttgaatg tatttagaaa aataaacaaa tagggttcc       5739 gcgcacattt ccccgaaaag tgccacctga cgtctaagaa accattatta tcatgacatt      5799
aacctataaa aataggcgta tcacgaggcc ctttcgtctt caagaattga tcgatcaa       5857
```

<210> SEQ ID NO 5
<211> LENGTH: 5734
<212> TYPE: DNA
<213> ORGANISM: Artificial Sequence
<220> FEATURE:
<221> NAME/KEY: CDS
<222> LOCATION: (300)...(1676)
<223> OTHER INFORMATION: Description of Artificial Sequence:/note = synthetic construct

<400> SEQUENCE: 5

```
ttctcatgtt tgacagctta tctcatcgac tgcacggtgc accaatgctt ctggcgtcag       60
gcagccatcg gaagctgtgg tatggctgtg caggtcgtaa atcactgcat aattcgtgtc      120
gctcaaggcg cactcccgtt ctggataatg tttttttgcgc cgacatcata acggttctgg      180
caaatattct gaaatgagct gttgacaatt aatcatcggc tcgtataatg tggaattgtg      240
agcggataac aattaatgtg tgaatgtgag cggatacaat ttcacacagg aaacagcgt      299 atg agc aca aaa aag aaa cca tta aca caa gag cag ctt gag gac gca       347
Met Ser Thr Lys Lys Lys Pro Leu Thr Gln Glu Gln Leu Glu Asp Ala
 1               5                  10                  15 cgt cgc ctt aaa gca att tat gaa aaa aag aaa aat gaa ctt ggc tta       395
Arg Arg Leu Lys Ala Ile Tyr Glu Lys Lys Lys Asn Glu Leu Gly Leu
            20                  25                  30 tcc cag gaa tct gtc gca gac aag atg ggg atg ggg cag tca ggc gtt       443
Ser Gln Glu Ser Val Ala Asp Lys Met Gly Met Gly Gln Ser Gly Val
        35                  40                  45 ggt gct tta ttt aat ggc atc aat gca tta aat gct tat aac gcg gca       491
Gly Ala Leu Phe Asn Gly Ile Asn Ala Leu Asn Ala Tyr Asn Ala Ala
    50                  55                  60 ttg cta gca aaa att ctc aaa gtt agc gtt gaa gaa ttc cat atg ttc       539
Leu Leu Ala Lys Ile Leu Lys Val Ser Val Glu Glu Phe His Met Phe
65                  70                  75                  80 aaa cac ctc cga aga tgg ttt atc act cac ata ttt ggg cgt tcc cgg       587
Lys His Leu Arg Arg Trp Phe Ile Thr His Ile Phe Gly Arg Ser Arg
                85                  90                  95 caa cgg gca agg ctg gtc tct aaa gaa gga aga tgt aac atc gag ttt       635
```

```
Gln Arg Ala Arg Leu Val Ser Lys Glu Gly Arg Cys Asn Ile Glu Phe
            100                 105                 110 ggc aat gtg gat gca cag tca agg ttt ata ttc ttt gtg gac atc tgg      683
Gly Asn Val Asp Ala Gln Ser Arg Phe Ile Phe Phe Val Asp Ile Trp
        115                 120                 125 aca act gtg ctg gac ctg aaa tgg agg tac aaa atg acc gtg ttc atc      731
Thr Thr Val Leu Asp Leu Lys Trp Arg Tyr Lys Met Thr Val Phe Ile
    130                 135                 140 aca gcc ttc ttg ggg agt tgg ttc ctc ttt ggt ctc ctg tgg tat gtc      779
Thr Ala Phe Leu Gly Ser Trp Phe Leu Phe Gly Leu Leu Trp Tyr Val
145                 150                 155                 160 gta gcg tat gtt cat aag gac ctc cca gag ttc tac ccg cct gac aac      827
Val Ala Tyr Val His Lys Asp Leu Pro Glu Phe Tyr Pro Pro Asp Asn
                165                 170                 175 cgc act cct tgt gtg gag aac att aat ggc atg act tca gcc ttt ctg      875
Arg Thr Pro Cys Val Glu Asn Ile Asn Gly Met Thr Ser Ala Phe Leu
            180                 185                 190 ttt tct cta gag act caa gtg acc ata ggt tac gga ttc agg ttt gtg      923
Phe Ser Leu Glu Thr Gln Val Thr Ile Gly Tyr Gly Phe Arg Phe Val
        195                 200                 205 aca gaa cag tgc gcc act gcc att ttc ctg ctt atc ttc cag tct att      971
Thr Glu Gln Cys Ala Thr Ala Ile Phe Leu Leu Ile Phe Gln Ser Ile
    210                 215                 220 ctt gga gtg atc atc aat tcc ttc atg tgt ggt gcc att tta gcc aag     1019
Leu Gly Val Ile Ile Asn Ser Phe Met Cys Gly Ala Ile Leu Ala Lys
225                 230                 235                 240 atc tct aga ccc aaa aaa cgt gct aaa acc att acg ttc agc aag aat     1067
Ile Ser Arg Pro Lys Lys Arg Ala Lys Thr Ile Thr Phe Ser Lys Asn
                245                 250                 255 gcg gtg atc agc aag cgt ggc ggg aag ctc tgc ctc ctc atc cga gtg     1115
Ala Val Ile Ser Lys Arg Gly Gly Lys Leu Cys Leu Leu Ile Arg Val
            260                 265                 270 gcc aat ctt agg aag agc ctt ctg att ggc agc cac ata tat ggc aag     1163
Ala Asn Leu Arg Lys Ser Leu Leu Ile Gly Ser His Ile Tyr Gly Lys
        275                 280                 285 ctt cta aag aca acc atc act cct gaa ggc gag acc atc att ttg gat     1211
Leu Leu Lys Thr Thr Ile Thr Pro Glu Gly Glu Thr Ile Ile Leu Asp
    290                 295                 300 cag acc aac atc aac ttt gtc gtc gac gct ggc aat gaa aat ttg ttc     1259
Gln Thr Asn Ile Asn Phe Val Val Asp Ala Gly Asn Glu Asn Leu Phe
305                 310                 315                 320 ttc ata tcc cca ctg acg atc tac cac att att gac cac aac agc cct     1307
Phe Ile Ser Pro Leu Thr Ile Tyr His Ile Ile Asp His Asn Ser Pro
                325                 330                 335 ttc ttc cac atg gca gca gaa act ctt tcc caa cag gac ttt gag ctg     1355
Phe Phe His Met Ala Ala Glu Thr Leu Ser Gln Gln Asp Phe Glu Leu
            340                 345                 350 gtg gtc ttt tta gat ggc aca gtg gaa tcc acc agt gca acc tgc cag     1403
Val Val Phe Leu Asp Gly Thr Val Glu Ser Thr Ser Ala Thr Cys Gln
        355                 360                 365 gtc cgc acg tca tac gtc cca gag gag gtg ctt tgg ggc tac cgt ttc     1451
Val Arg Thr Ser Tyr Val Pro Glu Glu Val Leu Trp Gly Tyr Arg Phe
    370                 375                 380 gtt cct att gtg tcc aag acc aag gaa ggg aaa tac cga gtt gat ttt     1499
Val Pro Ile Val Ser Lys Thr Lys Glu Gly Lys Tyr Arg Val Asp Phe
385                 390                 395                 400 cat aac ttc ggt aag aca gtg gaa gtg gag acc cct cac tgt gcc atg     1547
His Asn Phe Gly Lys Thr Val Glu Val Glu Thr Pro His Cys Ala Met
                405                 410                 415
```

-continued

| | | |
|---|---|---|
| tgc ctc tat aat gag aaa gat gcc agg gcc agg atg aag aga ggc tat<br>Cys Leu Tyr Asn Glu Lys Asp Ala Arg Ala Arg Met Lys Arg Gly Tyr<br>420 425 430 | | 1595 |
| gac aac cct aac ttt gtc ttg tca gaa gtt gat gaa acg gac gac acc<br>Asp Asn Pro Asn Phe Val Leu Ser Glu Val Asp Glu Thr Asp Asp Thr<br>435 440 445 | | 1643 |
| cag atg gcc tcg agg cac cat cac cac cac cac tgaaagcttt aatgcggtag<br>Gln Met Ala Ser Arg His His His His His His<br>450 455 | | 1696 |

| | | |
|---|---|---|
| tttatcacag ttaaattgct aacgcagtca ggcaccgtgt atgaaatcta acaatgcgct | | 1756 |
| catcgtcatc ctcggcaccg tcaccctgga tgctgtaggc ataggcttgg ttatgccggt | | 1816 |
| actgccgggc ctcttgcggg atcgacgcga ggctggatgg ccttccccat tatgattctt | | 1876 |
| ctcgcttccg gcggcatcgg gatgcccgcg ttgcaggcca tgctgtccag gcaggtagat | | 1936 |
| gacgaccatc agggacagct tcaaggatcg ctcgcggctc ttaccagcct aacttcgatc | | 1996 |
| actggaccgc tgatcgtcac ggcgatttat gccgcctcgg cgagcacatg gaacgggttg | | 2056 |
| gcatggattg taggcgccgc cctataccTT gtctgcctcc ccgcgttgcg tcgcggtgca | | 2116 |
| tggagccggg ccacctcgac ctgaatggaa gccgcggca cctcgctaac ggattcacca | | 2176 |
| ctccaagaat tggagccaat caattcttgc ggagaactgt gaatgcgcaa accaacccTT | | 2236 |
| ggcagaacat atccatcgcg tccgccatct ccagcagccg cacgcggcgc atctcgggca | | 2296 |
| gcgttgggtc ctggccacgg gtgcgcatga tcgtgctcct gtcgttgagg acccggctag | | 2356 |
| gctggcgggg ttgccttact ggttagcaga atgaatcacc gatacgcgag cgaacgtgaa | | 2416 |
| gcgactgctg ctgcaaaacg tctgcgacct gagcaacaac atgaatggtc ttcggtttcc | | 2476 |
| gtgtttcgta aagtctggaa acgcggaagt cagcgccctg caccattatg ttccggatct | | 2536 |
| gcatcgcagg atgctgctgg ctaccctgtg aacacctac atctgtatta acgaagcgct | | 2596 |
| ggcattgacc ctgagtgatt tttctctggt cccgccgcat ccataccgcc agttgtttac | | 2656 |
| cctcacaacg ttccagtaac cggcatgtt catcatcagt aacccgtatc gtgagcatcc | | 2716 |
| tctctcgttt catcggtatc attaccccca tgaacagaaa ttccccctta cacggaggca | | 2776 |
| tcaagtgacc aaacaggaaa aaccgccct taacatggcc cgctttatca gaagccagac | | 2836 |
| attaacgctt ctggagaaac tcaacgagct ggacgcggat gaacaggcag acatctgtga | | 2896 |
| atcgcttcac gaccacgctg atgagcttta ccgcagctgc ctcgcgcgtt tcggtgatga | | 2956 |
| cggtgaaaac ctctgacaca tgcagctccc ggagacggtc acagcttgtc tgtaagcgga | | 3016 |
| tgccgggagc agacaagccc gtcagggcgc gtcagcgggt gttggcgggt gtcggggcgc | | 3076 |
| agccatgacc cagtcacgta gcgatagcgg agtgtatact ggcttaacta tgcggcatca | | 3136 |
| gagcagattg tactgagagt gcaccatatg cggtgtgaaa taccgcacag atgcgtaagg | | 3196 |
| agaaaatacc gcatcaggcg ctcttccgct tcctcgctca ctgactcgct gcgctcggtc | | 3256 |
| gttcggctgc ggcgagcggt atcagctcac tcaaaggcgg taatacggtt atccacagaa | | 3316 |
| tcagggata acgcaggaaa gaacatgtga gcaaaaggcc agcaaaaggc caggaaccgt | | 3376 |
| aaaaaggccg cgttgctggc gtttttccat aggctccgcc cccctgacga gcatcacaaa | | 3436 |
| aatcgacgct caagtcagag gtggcgaaac ccgacaggac tataaagata ccaggcgttt | | 3496 |
| ccccctggaa gctccctcgt gcgctctcct gttccgaccc tgccgcttac cggatacctg | | 3556 |
| tccgcctttc tcccttcggg aagcgtggcg ctttctcata gctcacgctg taggtatctc | | 3616 |
| agttcggtgt aggtcgttcg ctccaagctg ggctgtgtgc acgaaccccc cgttcagccc | | 3676 |
| gaccgctgcg ccttatccgg taactatcgt cttgagtcca acccggtaag acacgactta | | 3736 |

```
tcgccactgg cagcagccac tggtaacagg attagcagag cgaggtatgt aggcggtgct    3796
acagagttct tgaagtggtg gcctaactac ggctacacta aaggacagt  atttggtatc    3856 tgcgctctgc tgaagccagt taccttcgga aaaagagttg gtagctcttg atccggcaaa    3916
caaaccaccg ctggtagcgg tggttttttt gtttgcaagc agcagattac gcgcagaaaa    3976
aaaggatctc aagaagatcc tttgatcttt tctacggggt ctgacgctca gtggaacgaa    4036
aactcacgtt aagggatttt ggtcatgaga ttatcaaaaa ggatcttcac ctagatcctt    4096
ttaccccggt tgataatcag aaaagcccca aaaacaggaa gattgtataa gcaaatattt    4156
aaattgtaaa cgttaatatt ttgttaaaat tcgcgttaaa ttttttgttaa atcagctcat    4216 tttttaacca ataggccgaa atcggcaaaa tcccttataa atcaaaagaa tagcccgaga    4276
tagggttgag tgttgttcca gtttggaaca agagtccact attaaagaac gtggactcca    4336
acgtcaaagg gcgaaaaacc gtctatcagg gcgatggccc actacgtgaa ccatcaccca    4396
aatcaagttt tttggggtcg aggtgccgta aagcactaaa tcggaaccct aaagggagcc    4456
cccgatttag agcttgacgg ggaaagccgg cgaacgtggc gagaaaggaa gggaagaaag    4516
cgaaaggagc gggcgctagg gcgctggcaa gtgtagcggt cacgctgcgc gtaaccacca    4576
cacccgccgc gcttaatgcg ccgctacagg gcgcgtaaat caatctaaag tatatatgag    4636
taaacttggt ctgacagtta ccaatgctta atcagtgagg cacctatctc agcgatctgt    4696
ctatttcgtt catccatagt tgcctgactc ccgtcgtgt  agataactac gatacgggag    4756
ggcttaccat ctggccccag tgctgcaatg ataccgcgag acccacgctc accggctcca    4816
gatttatcag caataaacca gccagccgga agggccgagc gcagaagtgg tcctgcaact    4876
ttatccgcct ccatccagtc tattaattgt tgccgggaag ctagagtaag tagttcgcca    4936
gttaatagtt tgcgcaacgt tgttgccatt gctgcaggca tcgtggtgtc acgctcgtcg    4996
tttggtatgg cttcattcag ctccggttcc caacgatcaa ggcgagttac atgatccccc    5056
atgttgtgca aaaagcggt  tagctccttc ggtcctccga tcgttgtcag aagtaagttg    5116
gccgcagtgt tatcactcat ggttatggca gcactgcata attctcttac tgtcatgcca    5176
tccgtaagat gcttttctgt gactggtgag tactcaacca agtcattctg agaatagtgt    5236
atgcggcgac cgagttgctc ttgcccggcg tcaacacggg ataataccgc gccacatagc    5296
agaactttaa aagtgctcat cattggaaaa cgttcttcgg ggcgaaaact ctcaaggatc    5356
ttaccgctgt tgagatccag ttcgatgtaa cccactcgtg cacccaactg atcttcagca    5416
tcttttactt tcaccagcgt ttctgggtga gcaaaaacag gaaggcaaaa tgccgcaaaa    5476
aagggaataa gggcgacacg gaaatgttga atactcatac tcttcctttt tcaatattat    5536
tgaagcattt atcagggtta ttgtctcatg agcggataca tatttgaatg tatttagaaa    5596
aataaacaaa taggggttcc gcgcacattt ccccgaaaag tgccacctga cgtctaagaa    5656
accattatta tcatgacatt aacctataaa aataggcgta tcacgaggcc ctttcgtctt    5716
caagaattga tcgatcaa                                                 5734

<210> SEQ ID NO 6
<211> LENGTH: 5197
<212> TYPE: DNA
<213> ORGANISM: Artificial Sequence
<220> FEATURE:
<221> NAME/KEY: CDS
<222> LOCATION: (300)...(1139)
<223> OTHER INFORMATION: Description of Artificial Sequence:/note =
      synthetic construct
```

-continued

```
<400> SEQUENCE: 6
ttctcatgtt tgacagctta tctcatcgac tgcacggtgc accaatgctt ctggcgtcag      60
gcagccatcg gaagctgtgg tatggctgtg caggtcgtaa atcactgcat aattcgtgtc     120
gctcaaggcg cactcccgtt ctggataatg ttttttgcgc cgacatcata acggttctgg     180
caaatattct gaaatgagct gttgacaatt aatcatcggc tcgtataatg tggaattgtg     240
agcggataac aattaatgtg tgaatgtgag cggatacaat ttcacacagg aaacagcgt     299 atg agc aca aaa aag aaa cca tta aca caa gag cag ctt gag gac gca      347
Met Ser Thr Lys Lys Lys Pro Leu Thr Gln Glu Gln Leu Glu Asp Ala
 1               5                  10                  15 cgt cgc ctt aaa gca att tat gaa aaa aag aaa aat gaa ctt ggc tta      395
Arg Arg Leu Lys Ala Ile Tyr Glu Lys Lys Lys Asn Glu Leu Gly Leu
            20                  25                  30 tcc cag gaa tct gtc gca gac aag atg ggg atg ggg cag tca ggc gtt      443
Ser Gln Glu Ser Val Ala Asp Lys Met Gly Met Gly Gln Ser Gly Val
        35                  40                  45 ggt gct tta ttt aat ggc atc aat gca tta aat gct tat aac gcg gca      491
Gly Ala Leu Phe Asn Gly Ile Asn Ala Leu Asn Ala Tyr Asn Ala Ala
 50                  55                  60 ttg cta gca aaa att ctc aaa gtt agc gtt gaa gaa ttc cat atg gct      539
Leu Leu Ala Lys Ile Leu Lys Val Ser Val Glu Glu Phe His Met Ala
 65                  70                  75                  80 gcc atc cgg aag aaa ctg gtg att gtt ggt gat gga gcc tgt gga aag      587
Ala Ile Arg Lys Lys Leu Val Ile Val Gly Asp Gly Ala Cys Gly Lys
                85                  90                  95 aca tgc ttg ctc ata gtc ttc agc aag gac cag ttc cca gag gtg tat      635
Thr Cys Leu Leu Ile Val Phe Ser Lys Asp Gln Phe Pro Glu Val Tyr
            100                 105                 110 gtg ccc aca gtg ttt gag aac tat gtg gca gat atc gag gtg gat gga      683
Val Pro Thr Val Phe Glu Asn Tyr Val Ala Asp Ile Glu Val Asp Gly
        115                 120                 125 aag cag gta gag ttg gct ttg tgg gac aca gct ggg cag gaa gat tat      731
Lys Gln Val Glu Leu Ala Leu Trp Asp Thr Ala Gly Gln Glu Asp Tyr
130                 135                 140 gat cgc ctg agg ccc ctc tcc tac cca gat acc gat gtt ata ctg atg      779
Asp Arg Leu Arg Pro Leu Ser Tyr Pro Asp Thr Asp Val Ile Leu Met
145                 150                 155                 160 tgt ttt tcc atc gac agc cct gat agt tta gaa aac atc cca gaa aag      827
Cys Phe Ser Ile Asp Ser Pro Asp Ser Leu Glu Asn Ile Pro Glu Lys
                165                 170                 175 tgg acc cca gaa gtc aag cat ttc tgt ccc aac gtg ccc atc atc ctg      875
Trp Thr Pro Glu Val Lys His Phe Cys Pro Asn Val Pro Ile Ile Leu
            180                 185                 190 gtt ggg aat aag aag gat ctt cgg aat gat gag cac aca agg cgg gag      923
Val Gly Asn Lys Lys Asp Leu Arg Asn Asp Glu His Thr Arg Arg Glu
        195                 200                 205 cta gcc aag atg aag cag gag ccg gtg aaa cct gaa gaa ggc aga gat      971
Leu Ala Lys Met Lys Gln Glu Pro Val Lys Pro Glu Glu Gly Arg Asp
    210                 215                 220 atg gca aac agg att ggc gct ttt ggg tac atg gag tgt tca gca aag     1019
Met Ala Asn Arg Ile Gly Ala Phe Gly Tyr Met Glu Cys Ser Ala Lys
225                 230                 235                 240 acc aaa gat gga gtg aga gag gtt ttt gaa atg gct acg aga gct gct     1067
Thr Lys Asp Gly Val Arg Glu Val Phe Glu Met Ala Thr Arg Ala Ala
                245                 250                 255 ctg caa gct aga cgt ggg aag aaa aaa tct ggt tgc ctt gtc ttg gcc     1115
Leu Gln Ala Arg Arg Gly Lys Lys Lys Ser Gly Cys Leu Val Leu Ala
```

-continued

```
                260                 265                 270
tcg agg cac cat cac cac cac cac tgaaagcttt aatgcggtag tttatcacag    1169
Ser Arg His His His His His His
        275                 280 ttaaattgct aacgcagtca ggcaccgtgt atgaaatcta acaatgcgct catcgtcatc   1229
ctcggcaccg tcaccctgga tgctgtaggc ataggcttgg ttatgccggt actgccgggc   1289
ctcttgcggg atcgacgcga ggctggatgg ccttccccat tatgattctt ctcgcttccg   1349
gcggcatcgg gatgcccgcg ttgcaggcca tgctgtccag gcaggtagat gacgaccatc   1409
agggacagct tcaaggatcg ctcgcggctc ttaccagcct aacttcgatc actggaccgc   1469
tgatcgtcac ggcgatttat gccgcctcgg cgagcacatg gaacgggttg gcatggattg   1529
taggcgccgc cctataccttt gtctgcctcc ccgcgttgcg tcgcggtgca tggagccggg   1589
ccacctcgac ctgaatggaa gccggcggca cctcgctaac ggattcacca ctccaagaat   1649
tggagccaat caattcttgc ggagaactgt gaatgcgcaa accaaccctt ggcagaacat   1709
atccatcgcg tccgccatct ccagcagccg cacgcgcgc atctcgggca gcgttgggtc    1769
ctggccacgg gtgcgcatga tcgtgctcct gtcgttgagg accggctag gctggcgggg    1829 ttgccttact ggttagcaga atgaatcacc gatacgcgag cgaacgtgaa gcgactgctg   1889
ctgcaaaacg tctgcgacct gagcaacaac atgaatggtc ttcggtttcc gtgtttcgta   1949
aagtctggaa acgcggaagt cagcgccctg caccattatg ttccggatct gcatcgcagg   2009
atgctgctgg ctaccctgtg gaacacctac atctgtatta acgaagcgct ggcattgacc   2069
ctgagtgatt tttctctggt cccgccgcat ccataccgcc agttgtttac cctcacaacg   2129
ttccagtaac cgggcatgtt catcatcagt aacccgtatc gtgagcatcc tctctcgttt   2189
catcggtatc attaccccca tgaacagaaa ttccccctta cacggaggca tcaagtgacc   2249
aaacaggaaa aaaccgccct taacatggcc cgctttatca gaagccagac attaacgctt   2309
ctggagaaac tcaacgagct ggacgcggat gaacaggcag acatctgtga atcgcttcac   2369
gaccacgctg atgagcttta ccgcagctgc ctcgcgcgtt tcggtgatga cggtgaaaac   2429
ctctgacaca tgcagctccc ggagacggtc acagcttgtc tgtaagcgga tgccgggagc   2489
agacaagccc gtcagggcgc gtcagcgggt gttggcgggt gtcggggcgc agccatgacc   2549
cagtcacgta gcgatagcgg agtgtatact ggcttaacta tgcggcatca gagcagattg   2609
tactgagagt gcaccatatg cggtgtgaaa taccgcacag atgcgtaagg agaaaatacc   2669
gcatcaggcg ctcttccgct tcctcgctca ctgactcgct gcgctcggtc gttcggctgc   2729
ggcgagcggt atcagctcac tcaaaggcgg taatacggtt atccacagaa tcaggggata   2789
acgcaggaaa gaacatgtga gcaaaaggcc agcaaaaggc caggaaccgt aaaaaggccg   2849
cgttgctggc gtttttccat aggctccgcc ccctgacga gcatcacaaa aatcgacgct    2909
caagtcagag gtggcgaaac ccgacaggac tataaagata ccaggcgttt ccccctggaa   2969
gctccctcgt gcgctctcct gttccgaccc tgccgcttac cggatacctg tccgcctttc   3029
tcccttcggg aagcgtggcg ctttctcata gctcacgctg taggtatctc agttcggtgt   3089
aggtcgttcg ctccaagctg ggctgtgtgc acgaaccccc cgttcagccc gaccgctgcg   3149
ccttatccgg taactatcgt cttgagtcca acccggtaag cacgactta tcgccactgg    3209 cagcagccac tggtaacagg attagcagag cgaggtatgt aggcggtgct acagagttct   3269
tgaagtggtg gcctaactac ggctacacta gaaggacagt atttggtatc tgcgctctgc   3329
tgaagccagt taccttcgga aaagagttg gtagctcttg atccggcaaa caaaccaccg    3389
```

| | |
|---|---:|
| ctggtagcgg tggttttttt gtttgcaagc agcagattac gcgcagaaaa aaaggatctc | 3449 |
| aagaagatcc tttgatcttt tctacggggt ctgacgctca gtggaacgaa aactcacgtt | 3509 |
| aagggatttt ggtcatgaga ttatcaaaaa ggatcttcac ctagatcctt ttaccccggt | 3569 |
| tgataatcag aaaagcccca aaaacaggaa gattgtataa gcaaatattt aaattgtaaa | 3629 |
| cgttaatatt ttgttaaaat tcgcgttaaa tttttgttaa atcagctcat tttttaacca | 3689 |
| ataggccgaa atcggcaaaa tcccttataa atcaaaagaa tagcccgaga tagggttgag | 3749 |
| tgttgttcca gtttggaaca agagtccact attaaagaac gtggactcca acgtcaaagg | 3809 |
| gcgaaaaacc gtctatcagg gcgatggccc actacgtgaa ccatcaccca aatcaagttt | 3869 |
| tttgggtcg aggtgccgta aagcactaaa tcggaaccct aaagggagcc cccgatttag | 3929 |
| agcttgacgg ggaaagccgg cgaacgtggc gagaaaggaa gggaagaaag cgaaaggagc | 3989 |
| gggcgctagg gcgctggcaa gtgtagcggt cacgctgcgc gtaaccacca cacccgccgc | 4049 |
| gcttaatgcg ccgctacagg gcgcgtaaat caatctaaag tatatatgag taaacttggt | 4109 |
| ctgacagtta ccaatgctta atcagtgagg cacctatctc agcgatctgt ctatttcgtt | 4169 |
| catccatagt tgcctgactc cccgtcgtgt agataactac gatacgggag ggcttaccat | 4229 |
| ctggccccag tgctgcaatg ataccgcgag acccacgctc accggctcca gatttatcag | 4289 |
| caataaacca gccagccgga agggccgagc gcagaagtgg tcctgcaact ttatccgcct | 4349 |
| ccatccagtc tattaattgt tgccgggaag ctagagtaag tagttcgcca gttaatagtt | 4409 |
| tgcgcaacgt tgttgccatt gctgcaggca tcgtggtgtc acgctcgtcg tttggtatgg | 4469 |
| cttcattcag ctccggttcc caacgatcaa ggcgagttac atgatccccc atgttgtgca | 4529 |
| aaaaagcggt tagctccttc ggtcctccga tcgttgtcag aagtaagttg gccgcagtgt | 4589 |
| tatcactcat ggttatggca gcactgcata attctcttac tgtcatgcca tccgtaagat | 4649 |
| gcttttctgt gactggtgag tactcaacca agtcattctg agaatagtgt atgcggcgac | 4709 |
| cgagttgctc ttgcccggcg tcaacacggg ataataccgc gccacatagc agaactttaa | 4769 |
| aagtgctcat cattggaaaa cgttcttcgg ggcgaaaact ctcaaggatc ttaccgctgt | 4829 |
| tgagatccag ttcgatgtaa cccactcgtg cacccaactg atcttcagca tcttttactt | 4889 |
| tcaccagcgt ttctgggtga gcaaaaacag gaaggcaaaa tgccgcaaaa agggaataa | 4949 |
| gggcgacacg gaaatgttga atactcatac tcttcctttt tcaatattat tgaagcattt | 5009 |
| atcagggtta ttgtctcatg agcggataca tatttgaatg tatttagaaa aataaacaaa | 5069 |
| taggggttcc gcgcacattt ccccgaaaag tgccacctga cgtctaagaa accattatta | 5129 |
| tcatgacatt aacctataaa aataggcgta tcacgaggcc ctttcgtctt caagaattga | 5189 |
| tcgatcaa | 5197 |

<210> SEQ ID NO 7
<211> LENGTH: 5688
<212> TYPE: DNA
<213> ORGANISM: Artificial Sequence
<220> FEATURE:
<221> NAME/KEY: CDS
<222> LOCATION: (300)...(1631)
<223> OTHER INFORMATION: Description of Artificial Sequence:/note = synthetic construct

<400> SEQUENCE: 7

| | |
|---|---:|
| ttctcatgtt tgacagctta tctcatcgac tgcacggtgc accaatgctt ctggcgtcag | 60 |
| gcagccatcg gaagctgtgg tatggctgtg caggtcgtaa atcactgcat aattcgtgtc | 120 |

-continued

```
gctcaaggcg cactcccgtt ctggataatg ttttttgcgc cgacatcata acggttctgg      180
caaatattct gaaatgagct gttgacaatt aatcatcggc tcgtataatg tggaattgtg      240
agcggataac aattaatgtg tgaatgtgag cggatacaat ttcacacagg aaacagcgt       299 atg agc aca aaa aag aaa cca tta aca caa gag cag ctt gag gac gca        347
Met Ser Thr Lys Lys Lys Pro Leu Thr Gln Glu Gln Leu Glu Asp Ala
 1               5                  10                  15 cgt cgc ctt aaa gca att tat gaa aaa aag aaa aat gaa ctt ggc tta        395
Arg Arg Leu Lys Ala Ile Tyr Glu Lys Lys Lys Asn Glu Leu Gly Leu
              20                  25                  30 tcc cag gaa tct gtc gca gac aag atg ggg atg ggg cag tca ggc gtt        443
Ser Gln Glu Ser Val Ala Asp Lys Met Gly Met Gly Gln Ser Gly Val
          35                  40                  45 ggt gct tta ttt aat ggc atc aat gca tta aat gct tat aac gcg gca        491
Gly Ala Leu Phe Asn Gly Ile Asn Ala Leu Asn Ala Tyr Asn Ala Ala
      50                  55                  60 ttg cta gca aaa att ctc aaa gtt agc gtt gaa gaa ttc gca gct cat        539
Leu Leu Ala Lys Ile Leu Lys Val Ser Val Glu Glu Phe Ala Ala His
 65                  70                  75                  80 atg aag gag acg cgg ggc gac gga ggg agc gcc ccc ttc tgc acc cgc        587
Met Lys Glu Thr Arg Gly Asp Gly Gly Ser Ala Pro Phe Cys Thr Arg
              85                  90                  95 ctc aac cac tcg tat cca ggc atg tgg gcg ccc gag gca cgg ggc aac        635
Leu Asn His Ser Tyr Pro Gly Met Trp Ala Pro Glu Ala Arg Gly Asn
         100                 105                 110 ctc aca cgc ccc cca ggg ccc ggc gag gac tgt ggc tcg gtg tcc gtg        683
Leu Thr Arg Pro Pro Gly Pro Gly Glu Asp Cys Gly Ser Val Ser Val
     115                 120                 125 gcc ttc ccg atc acc atg ctg atc acc ggc ttc gtg ggc aac gcg ctg        731
Ala Phe Pro Ile Thr Met Leu Ile Thr Gly Phe Val Gly Asn Ala Leu
 130                 135                 140 gcc atg ctg ctc gtg tcg cgt agc tac cgg cgt cgg gag agc aag cgc        779
Ala Met Leu Leu Val Ser Arg Ser Tyr Arg Arg Arg Glu Ser Lys Arg
145                 150                 155                 160 aag aag tcg ttc ctg ttg tgc atc ggc tgg ctg gcg ctc act gac ctg        827
Lys Lys Ser Phe Leu Leu Cys Ile Gly Trp Leu Ala Leu Thr Asp Leu
             165                 170                 175 gtc ggg cag ctg ctc aca agc ccc gtg gtc atc ttg gtg tac cta tcc        875
Val Gly Gln Leu Leu Thr Ser Pro Val Val Ile Leu Val Tyr Leu Ser
         180                 185                 190 aag cag cgc tgg gag cag ctc gac ccg tcg ggg cgc ctg tgc acc ttc        923
Lys Gln Arg Trp Glu Gln Leu Asp Pro Ser Gly Arg Leu Cys Thr Phe
     195                 200                 205 ttt ggt ctg acc atg act gtt ttc ggg ctg tcc tcg ctc ttc atc gcc        971
Phe Gly Leu Thr Met Thr Val Phe Gly Leu Ser Ser Leu Phe Ile Ala
 210                 215                 220 agc gcc atg gct gtc gag agg gcg ctg gcc atc cgt gcg cca cac tgg       1019
Ser Ala Met Ala Val Glu Arg Ala Leu Ala Ile Arg Ala Pro His Trp
225                 230                 235                 240 tac gcg agc cac atg aag acg cgt gcc act cgc gcc gtc ctg ctg ggc       1067
Tyr Ala Ser His Met Lys Thr Arg Ala Thr Arg Ala Val Leu Leu Gly
             245                 250                 255 gtg tgg ctg gca gtg ctc gcc ttc gcc ctg cta cct gtg ctg ggt gtg       1115
Val Trp Leu Ala Val Leu Ala Phe Ala Leu Leu Pro Val Leu Gly Val
         260                 265                 270 ggt cag tac acc atc cag tgg ccc ggg acg tgg tgc ttc atc agc acc       1163
Gly Gln Tyr Thr Ile Gln Trp Pro Gly Thr Trp Cys Phe Ile Ser Thr
     275                 280                 285
```

-continued

| | | |
|---|---|---|
| gga cga ggg gac aac ggg acg agc tct tca cac aac tgg ggc aac ctt<br>Gly Arg Gly Asp Asn Gly Thr Ser Ser Ser His Asn Trp Gly Asn Leu<br>290                       295                     300 | 1211 |
| ttc ttc gcc tcc acc ttt gcc ttc ctg ggc ctc ttg gcg ctg gcc atc<br>Phe Phe Ala Ser Thr Phe Ala Phe Leu Gly Leu Leu Ala Leu Ala Ile<br>305                   310                    315                   320 | 1259 |
| acc ttc acc tgc aac ctg gcc acc att aag gct ctg gtg tcc cgc tgc<br>Thr Phe Thr Cys Asn Leu Ala Thr Ile Lys Ala Leu Val Ser Arg Cys<br>                    325                     330                   335 | 1307 |
| cgg gca aag gcg gca gca tca cag tcc agt gcc cag tgg ggc cgg atc<br>Arg Ala Lys Ala Ala Ala Ser Gln Ser Ser Ala Gln Trp Gly Arg Ile<br>            340                   345                   350 | 1355 |
| acg acc gag acg gcc atc cag ctc atg ggg atc atg tgc gtg ctg tcg<br>Thr Thr Glu Thr Ala Ile Gln Leu Met Gly Ile Met Cys Val Leu Ser<br>355                       360                    365 | 1403 |
| gtc tgc tgg tcg ccc cta ctg ata atg atg ttg aaa atg atc ttc aat<br>Val Cys Trp Ser Pro Leu Leu Ile Met Met Leu Lys Met Ile Phe Asn<br>     370                   375                   380 | 1451 |
| cag aca tca gtt gag cac tgc aag aca gac aca gga aag cag aaa gaa<br>Gln Thr Ser Val Glu His Cys Lys Thr Asp Thr Gly Lys Gln Lys Glu<br>385                       390                    395                400 | 1499 |
| tgc aac ttc ttc tta ata gct gtt cgc ctg gct tca ctg aac cag ata<br>Cys Asn Phe Phe Leu Ile Ala Val Arg Leu Ala Ser Leu Asn Gln Ile<br>                  405                    410                   415 | 1547 |
| ttg gat ccc tgg gtt tat ctg ctg cta aga aag att ctt ctt cgg aag<br>Leu Asp Pro Trp Val Tyr Leu Leu Leu Arg Lys Ile Leu Leu Arg Lys<br>            420                   425                   430 | 1595 |
| ttt tgc cag gcc tcg agg cac cat cac cac cac cac tgaagcttta<br>Phe Cys Gln Ala Ser Arg His His His His His His<br>            435                       440 | 1641 |
| atgcggtagt ttatcacagt taaattgcta acgcagtcag gcaccgtgta tgaaatctaa | 1701 |
| caatgcgctc atcgtcatcc tcggcaccgt caccctggat gctgtaggca taggcttggt | 1761 |
| tatgccggta ctgccgggcc tcttgcggga tcgacgcgag gctggatggc cttccccatt | 1821 |
| atgattcttc tcgcttccgg cggcatcggg atgcccgcgt tgcaggccat gctgtccagg | 1881 |
| caggtagatg acgaccatca gggacagctt caaggatcgc tcgcggctct taccagccta | 1941 |
| acttcgatca ctggaccgct gatcgtcacg gcgatttatg ccgcctcggc gagcacatgg | 2001 |
| aacgggttgg catggattgt aggcgccgcc ctataccttg tctgcctccc cgcgttgcgt | 2061 |
| cgcggtgcat ggagccgggc cacctcgacc tgaatggaag ccggcggcac ctcgctaacg | 2121 |
| gattcaccac tccaagaatt ggagccaatc aattcttgcg gagaactgtg aatgcgcaaa | 2181 |
| ccaacccttg gcagaacata tccatcgcgt ccgccatctc cagcagccgc acgcggcgca | 2241 |
| tctcgggcag cgttgggtcc tggccacggg tgcgcatgat cgtgctcctg tcgttgagga | 2301 |
| cccggctagg ctgcgggt tgccttactg gttagcagaa tgaatcaccg atacgcgagc | 2361 |
| gaacgtgaag cgactgctgc tgcaaaacgt ctgcgacctg agcaacaaca tgaatggtct | 2421 |
| tcggtttccg tgtttcgtaa agtctggaaa cgcggaagtc agcgccctgc accattatgt | 2481 |
| tccggatctg catcgcagga tgctgctggc taccctgtgg aacacctaca tctgtattaa | 2541 |
| cgaagcgctg gcattgaccc tgagtgattt ttctctggtc ccgccgcatc catacccgcca | 2601 |
| gttgtttacc ctcacaacgt tccagtaacc gggcatgttc atcatcagta acccgtatcg | 2661 |
| tgagcatcct ctctcgtttc atcggtatca ttaccccat gaacagaaat tccccttac | 2721 |
| acggaggcat caagtgacca aacaggaaaa aaccgccctt aacatgggcc gctttatcag | 2781 |
| aagccagaca ttaacgcttc tggagaaact caacgagctg gacgcggatg aacaggcaga | 2841 |

```
catctgtgaa tcgcttcacg accacgctga tgagctttac cgcagctgcc tcgcgcgttt   2901
cggtgatgac ggtgaaaacc tctgacacat gcagctcccg gagacggtca cagcttgtct   2961
gtaagcggat gccgggagca gacaagcccg tcagggcgcg tcagcgggtg ttggcgggtg   3021
tcggggcgca gccatgaccc agtcacgtag cgatagcgga gtgtatactg gcttaactat   3081
gcggcatcag agcagattgt actgagagtg caccatatgc ggtgtgaaat accgcacaga   3141
tgcgtaagga gaaaataccg catcaggcgc tcttccgctt cctcgctcac tgactcgctg   3201
cgctcggtcg ttcggctgcg gcgagcggta tcagctcact caaaggcggt aatacggtta   3261
tccacagaat caggggataa cgcaggaaag aacatgtgag caaaaggcca gcaaaaggcc   3321
aggaaccgta aaaaggccgc gttgctggcg ttttccata ggctccgccc cctgacgag    3381
catcacaaaa atcgacgctc aagtcagagg tggcgaaacc cgacaggact ataaagatac   3441
caggcgtttc ccctggaag ctccctcgtg cgctctcctg ttccgaccct gccgcttacc    3501
ggatacctgt ccgcctttct cccttcggga agcgtggcgc tttctcatag ctcacgctgt   3561
aggtatctca gttcggtgta ggtcgttcgc tccaagctgg gctgtgtgca cgaacccccc   3621
gttcagcccg accgctgcgc cttatccggt aactatcgtc ttgagtccaa cccggtaaga   3681
cacgacttat cgccactggc agcagccact ggtaacagga ttagcagagc gaggtatgta   3741
ggcggtgcta cagagttctt gaagtggtgg cctaactacg gctacactag aaggacagta   3801
tttggtatct gcgctctgct gaagccagtt accttcggaa aaagagttgg tagctcttga   3861
tccggcaaac aaaccaccgc tggtagcggt ggtttttttg tttgcaagca gcagattacg   3921
cgcagaaaaa aaggatctca agaagatcct ttgatctttt ctacggggtc tgacgctcag   3981
tggaacgaaa actcacgtta agggattttg gtcatgagat tatcaaaaag gatcttcacc   4041
tagatccttt tacccggtt gataatcaga aagccccaa aacaggaag attgtataag     4101
caaatattta aattgtaaac gttaatattt tgttaaaatt cgcgttaaat ttttgttaaa   4161
tcagctcatt ttttaaccaa taggccgaaa tcggcaaaat cccttataaa tcaaaagaat   4221
agcccgagat agggttgagt gttgttccag tttggaacaa gagtccacta ttaaagaacg   4281
tggactccaa cgtcaaaggg cgaaaaaccg tctatcaggg cgatggccca ctacgtgaac   4341
catcacccaa atcaagtttt tggggtcga ggtgccgtaa agcactaaat cggaaccta     4401
aagggagccc ccgatttaga gcttgacggg gaaagccggc gaacgtggcg agaaaggaag   4461
ggaagaaagc gaaaggagcg gcgctaggg cgctggcaag tgtagcggtc acgctgcgcg    4521
taaccaccac acccgccgcg cttaatgcgc cgctacaggg cgcgtaaatc aatctaaagt   4581
atatatgagt aaacttggtc tgacagttac caatgcttaa tcagtgaggc acctatctca   4641
gcgatctgtc tatttcgttc atccatagtt gcctgactcc ccgtcgtgta gataactacg   4701
atacgggagg gcttaccatc tggccccagt gctgcaatga taccgcgaga cccacgctca   4761
ccggctccag atttatcagc aataaaccag ccagccggaa gggccgagcg cagaagtggt   4821
cctgcaactt tatccgcctc catccagtct attaattgtt gccgggaagc tagagtaagt   4881
agttcgccag ttaatagttt cgcaacgtt gttgccattg ctgcaggcat cgtggtgtca    4941
cgctcgtcgt ttggtatggc ttcattcagc tccggttccc aacgatcaag gcgagttaca   5001
tgatccccca tgttgtgcaa aaaagcggtt agctccttcg gtcctccgat cgttgtcaga   5061
agtaagttgg ccgcagtgtt atcactcatg gttatggcag cactgcataa ttctcttact   5121
gtcatgccat ccgtaagatg cttttctgtg actggtgagt actcaaccaa gtcattctga   5181
```

-continued

```
gaatagtgta tgcggcgacc gagttgctct tgcccggcgt caacacggga taataccgcg    5241
ccacatagca gaactttaaa agtgctcatc attggaaaac gttcttcggg gcgaaaactc    5301
tcaaggatct taccgctgtt gagatccagt tcgatgtaac ccactcgtgc acccaactga    5361
tcttcagcat cttttacttt caccagcgtt tctgggtgag caaaaacagg aaggcaaaat    5421
gccgcaaaaa agggaataag gcgacacgg aaatgttgaa tactcatact cttccttttt    5481
caatattatt gaagcattta tcagggttat tgtctcatga gcggatacat atttgaatgt    5541
atttagaaaa ataaacaaat aggggttccg cgcacatttc cccgaaaagt gccacctgac    5601
gtctaagaaa ccattattat catgacatta acctataaaa ataggcgtat cacgaggccc    5661
tttcgtcttc aagaattgat cgatcaa                                       5688
```

<210> SEQ ID NO 8
<211> LENGTH: 6587
<212> TYPE: DNA
<213> ORGANISM: Artificial Sequence
<220> FEATURE:
<221> NAME/KEY: CDS
<222> LOCATION: (300)...(2267)
<223> OTHER INFORMATION: Description of Artificial Sequence:/note = synthetic construct

<400> SEQUENCE: 8

```
ttctcatgtt tgacagctta tctcatcgac tgcacggtgc accaatgctt ctggcgtcag     60
gcagccatcg gaagctgtgg tatggctgtg caggtcgtaa atcactgcat aattcgtgtc    120
gctcaaggcg cactcccgtt ctggataatg ttttttgcgc cgacatcata acggttctgg    180
caaatattct gaaatgagct gttgacaatt aatcatcggc tcgtataatg tggaattgtg    240
agcggataac aattaatgtg tgaatgtgag cggatacaat ttcacacagg aaacagcgt    299 atg agc aca aaa aag aaa cca tta aca caa gag cag ctt gag gac gca    347
Met Ser Thr Lys Lys Lys Pro Leu Thr Gln Glu Gln Leu Glu Asp Ala
 1               5                  10                  15 cgt cgc ctt aaa gca att tat gaa aaa aag aaa aat gaa ctt ggc tta    395
Arg Arg Leu Lys Ala Ile Tyr Glu Lys Lys Lys Asn Glu Leu Gly Leu
             20                  25                  30 tcc cag gaa tct gtc gca gac aag atg ggg atg ggg cag tca ggc gtt    443
Ser Gln Glu Ser Val Ala Asp Lys Met Gly Met Gly Gln Ser Gly Val
         35                  40                  45 ggt gct tta ttt aat ggc atc aat gca tta aat gct tat aac gcg gca    491
Gly Ala Leu Phe Asn Gly Ile Asn Ala Leu Asn Ala Tyr Asn Ala Ala
     50                  55                  60 ttg cta gca aaa att ctc aaa gtt agc gtt gaa gaa ttc gca gct cat    539
Leu Leu Ala Lys Ile Leu Lys Val Ser Val Glu Glu Phe Ala Ala His
 65                  70                  75                  80 atg aag gag acg cgg ggc gac gga ggg agc gcc ccc ttc tgc acc cgc    587
Met Lys Glu Thr Arg Gly Asp Gly Gly Ser Ala Pro Phe Cys Thr Arg
                 85                  90                  95 ctc aac cac tcg tat cca ggc atg tgg gcg ccc gag gca cgg ggc aac    635
Leu Asn His Ser Tyr Pro Gly Met Trp Ala Pro Glu Ala Arg Gly Asn
            100                 105                 110 ctc aca cgc ccc cca ggg ccc ggc gag gac tgt ggc tcg gtg tcc gtg    683
Leu Thr Arg Pro Pro Gly Pro Gly Glu Asp Cys Gly Ser Val Ser Val
        115                 120                 125 gcc ttc ccg atc acc atg ctg atc acc ggc ttc gtg ggc aac gcg ctg    731
Ala Phe Pro Ile Thr Met Leu Ile Thr Gly Phe Val Gly Asn Ala Leu
    130                 135                 140 gcc atg ctg ctc gtg tcg cgt agc tac cgg cgt cgg gag agc aag cgc    779
Ala Met Leu Leu Val Ser Arg Ser Tyr Arg Arg Arg Glu Ser Lys Arg
```

```
                145                     150                     155                     160
aag aag tcg ttc ctg ttg tgc atc ggc tgg ctg gcg ctc act gac ctg           827
Lys Lys Ser Phe Leu Leu Cys Ile Gly Trp Leu Ala Leu Thr Asp Leu
                    165                     170                     175 gtc ggg cag ctg ctc aca agc ccc gtg gtc atc ttg gtg tac cta tcc           875
Val Gly Gln Leu Leu Thr Ser Pro Val Val Ile Leu Val Tyr Leu Ser
                    180                     185                     190 aag cag cgc tgg gag cag ctc gac ccg tcg ggg cgc ctg tgc acc ttc           923
Lys Gln Arg Trp Glu Gln Leu Asp Pro Ser Gly Arg Leu Cys Thr Phe
                    195                     200                     205 ttt ggt ctg acc atg act gtt ttc ggg ctg tcc tcg ctc ttc atc gcc           971
Phe Gly Leu Thr Met Thr Val Phe Gly Leu Ser Ser Leu Phe Ile Ala
                    210                     215                     220 agc gcc atg gct gtc gag agg gcg ctg gcc atc cgt gcg cca cac tgg          1019
Ser Ala Met Ala Val Glu Arg Ala Leu Ala Ile Arg Ala Pro His Trp
225                     230                     235                     240 tac gcg agc cac atg aag acg cgt gcc act cgc gcc gtc ctg ctg ggc          1067
Tyr Ala Ser His Met Lys Thr Arg Ala Thr Arg Ala Val Leu Leu Gly
                    245                     250                     255 gtg tgg ctg gca gtg ctc gcc ttc gcc ctg cta cct gtg ctg ggt gtg          1115
Val Trp Leu Ala Val Leu Ala Phe Ala Leu Leu Pro Val Leu Gly Val
                    260                     265                     270 ggt cag tac acc atc cag tgg ccc ggg acg tgg tgc ttc atc agc acc          1163
Gly Gln Tyr Thr Ile Gln Trp Pro Gly Thr Trp Cys Phe Ile Ser Thr
                    275                     280                     285 gga cga ggg gac aac ggg acg agc tct tca cac aac tgg ggc aac ctt          1211
Gly Arg Gly Asp Asn Gly Thr Ser Ser Ser His Asn Trp Gly Asn Leu
                    290                     295                     300 ttc ttc gcc tcc acc ttt gcc ttc ctg ggc ctc ttg gcg ctg gcc atc          1259
Phe Phe Ala Ser Thr Phe Ala Phe Leu Gly Leu Leu Ala Leu Ala Ile
305                     310                     315                     320 acc ttc acc tgc aac ctg gcc acc att aag gct ctg gtg tcc cgc tgc          1307
Thr Phe Thr Cys Asn Leu Ala Thr Ile Lys Ala Leu Val Ser Arg Cys
                    325                     330                     335 cgg gca aag gcg gca gca tca cag tcc agt gcc cag tgg ggc cgg atc          1355
Arg Ala Lys Ala Ala Ala Ser Gln Ser Ser Ala Gln Trp Gly Arg Ile
                    340                     345                     350 acg acc gag acg gcc atc cag ctc atg ggg atc atg tgc gtg ctg tcg          1403
Thr Thr Glu Thr Ala Ile Gln Leu Met Gly Ile Met Cys Val Leu Ser
                    355                     360                     365 gtc tgc tgg tcg ccc cta ctg ata atg atg ttg aaa atg atc ttc aat          1451
Val Cys Trp Ser Pro Leu Leu Ile Met Met Leu Lys Met Ile Phe Asn
                    370                     375                     380 cag aca tca gtt gag cac tgc aag aca gac aca gga aag cag aaa gaa          1499
Gln Thr Ser Val Glu His Cys Lys Thr Asp Thr Gly Lys Gln Lys Glu
385                     390                     395                     400 tgc aac ttc ttc tta ata gct gtt cgc ctg gct tca ctg aac cag ata          1547
Cys Asn Phe Phe Leu Ile Ala Val Arg Leu Ala Ser Leu Asn Gln Ile
                    405                     410                     415 ttg gat ccc tgg gtt tat ctg ctg cta aga aag att ctt ctt cgg aag          1595
Leu Asp Pro Trp Val Tyr Leu Leu Leu Arg Lys Ile Leu Leu Arg Lys
                    420                     425                     430 ttt tgc cag gta att cat gaa aat aat gag cag aag gat gaa att cag          1643
Phe Cys Gln Val Ile His Glu Asn Asn Glu Gln Lys Asp Glu Ile Gln
                    435                     440                     445 cgt gag aac agg aac gtc tca cac agt ggg caa cac gaa gag gcc aga          1691
Arg Glu Asn Arg Asn Val Ser His Ser Gly Gln His Glu Glu Ala Arg
450                     455                     460 gac agt gag aag agc aaa acc atc cct ggc ctg ttc tcc att ctg ctg          1739
Asp Ser Glu Lys Ser Lys Thr Ile Pro Gly Leu Phe Ser Ile Leu Leu
```

```
Asp Ser Glu Lys Ser Lys Thr Ile Pro Gly Leu Phe Ser Ile Leu Leu
465                 470                 475                 480 cag gct gac cct ggt gct cgt cct tat cag caa gcc tcg agc ctg gtg      1787
Gln Ala Asp Pro Gly Ala Arg Pro Tyr Gln Gln Ala Ser Ser Leu Val
                485                 490                 495 cca cgc gga tcc gtt cga gaa atc tac gag atg tat gaa gcg gtt agc      1835
Pro Arg Gly Ser Val Arg Glu Ile Tyr Glu Met Tyr Glu Ala Val Ser
            500                 505                 510 atg cag ccg tca ctt aga agt gag tat gag tac cct gtt ttt tct cat      1883
Met Gln Pro Ser Leu Arg Ser Glu Tyr Glu Tyr Pro Val Phe Ser His
        515                 520                 525 gtt cag gca ggg atg ttc tca cct aag ctt aga acc ttt acc aaa ggt      1931
Val Gln Ala Gly Met Phe Ser Pro Lys Leu Arg Thr Phe Thr Lys Gly
    530                 535                 540 gat gcg gag aga tgg gta agc aca acc aaa aaa gcc agt gat tct gca      1979
Asp Ala Glu Arg Trp Val Ser Thr Thr Lys Lys Ala Ser Asp Ser Ala
545                 550                 555                 560 ttc tgg ctt gag gtt gaa ggt aat tcc atg acc gca cca aca ggc tcc      2027
Phe Trp Leu Glu Val Glu Gly Asn Ser Met Thr Ala Pro Thr Gly Ser
                565                 570                 575 aag cca agc ttt cct gac gga atg tta att ctc gtt gac cct gag cag      2075
Lys Pro Ser Phe Pro Asp Gly Met Leu Ile Leu Val Asp Pro Glu Gln
            580                 585                 590 gct gtt gag cca ggt gat ttc tgc ata gcc aga ctt ggg ggt gat gag      2123
Ala Val Glu Pro Gly Asp Phe Cys Ile Ala Arg Leu Gly Gly Asp Glu
        595                 600                 605 ttt acc ttc aag aaa ctg atc agg gat agc ggt cag gtg ttt tta caa      2171
Phe Thr Phe Lys Lys Leu Ile Arg Asp Ser Gly Gln Val Phe Leu Gln
    610                 615                 620 cca cta aac cca cag tac cca atg atc cca tgc aat gag agt tgt tcc      2219
Pro Leu Asn Pro Gln Tyr Pro Met Ile Pro Cys Asn Glu Ser Cys Ser
625                 630                 635                 640 gtt gtg ggg aaa gtt atc gct agt cag tgg cct gaa gag acg ttt ggc      2267
Val Val Gly Lys Val Ile Ala Ser Gln Trp Pro Glu Glu Thr Phe Gly
                645                 650                 655 tgatcggcaa ggtgttctgg tcggcgcata gctgataaca attgagcaag aatcttcatc    2327
gaattagggg aattttcact cccctcagaa cataacatag taaatggatt gaattatgaa    2387
gaatggtttt tatgcgactt accgcagcaa aaataaaggg aaagataagc gctcaataaa    2447
cctgtctgtt ttccttaatt ctctgctggc tgataatcat cacctgcagg ttggctccaa    2507
ttatttgtat attcataaaa tcgataagct ttaatgcggt agtttatcac agttaaattg    2567
ctaacgcagt caggcaccgt gtatgaaatc taacaatgcg ctcatcgtca tcctcggcac    2627
cgtcaccctg gatgctgtag cataggctt ggttatgccg gtactgccgg gcctcttgcg    2687
ggatcgacgc gaggctggat ggccttcccc attatgattc ttctcgcttc cggcggcatc    2747
gggatgcccg cgttgcaggc catgctgtcc aggcaggtag atgacgacca tcagggacag    2807
cttcaaggat cgctcgcggc tcttaccagc ctaacttcga tcactggacc gctgatcgtc    2867
acggcgattt atgccgcctc ggcgagcaca tggaacgggt tggcatggat tgtaggcgcc    2927
gccctatacc ttgtctgcct ccccgcgttg cgtcgcggtg catggagccg gccacctcg    2987 acctgaatgg aagccggcgg cacctcgcta acgattcac cactccaaga attggagcca    3047
atcaattctt gcggagaact gtgaatgcgc aaaccaaccc ttggcagaac atatccatcg    3107
cgtccgccat ctccagcagc cgcacgcggc gcatctcggg cagcgttggg tcctggccac    3167
gggtgcgcat gatcgtgctc ctgtcgttga ggacccggct aggctggcgg ggttgcctta    3227
```

```
ctggttagca gaatgaatca ccgatacgcg agcgaacgtg aagcgactgc tgctgcaaaa    3287
cgtctgcgac ctgagcaaca acatgaatgg tcttcggttt ccgtgtttcg taaagtctgg    3347
aaacgcggaa gtcagcgccc tgcaccatta tgttccggat ctgcatcgca ggatgctgct    3407
ggctaccctg tggaacacct acatctgtat taacgaagcg ctggcattga ccctgagtga    3467
tttttctctg gtcccgccgc atccataccg ccagttgttt accctcacaa cgttccagta    3527
accgggcatg ttcatcatca gtaacccgta tcgtgagcat cctctctcgt ttcatcggta    3587
tcattacccc catgaacaga aattcccccct tacacgagg catcaagtga ccaaacagga    3647
aaaaaccgcc cttaacatgg cccgctttat cagaagccag acattaacgc ttctggagaa    3707
actcaacgag ctggacgcgg atgaacaggc agacatctgt gaatcgcttc acgaccacgc    3767
tgatgagctt taccgcagct gcctcgcgcg tttcggtgat gacggtgaaa acctctgaca    3827
catgcagctc ccgagacgg tcacagcttg tctgtaagcg gatgccggga gcagacaagc    3887
ccgtcaggggc gcgtcagcgg gtgttggcgg gtgtcggggc gcagccatga cccagtcacg    3947
tagcgatagc ggagtgtata ctggcttaac tatgcggcat cagagcagat tgtactgaga    4007
gtgcaccata tgcggtgtga ataccgcac agatgcgtaa ggagaaaata ccgcatcagg    4067
cgctcttccg cttcctcgct cactgactcg ctgcgctcgg tcgttcggct gcggcgagcg    4127
gtatcagctc actcaaaggc ggtaatacgg ttatccacag aatcagggga taacgcagga    4187
aagaacatgt gagcaaaagg ccagcaaaag gccaggaacc gtaaaaaggc cgcgttgctg    4247
gcgttttttcc ataggctccg ccccccctgac gagcatcaca aaaatcgacg ctcaagtcag    4307
aggtggcgaa acccgacagg actataaaga taccaggcgt ttccccctgg aagctccctc    4367
gtgcgctctc ctgttccgac cctgccgctt accggatacc tgtccgcctt ctcccttcg    4427
ggaagcgtgg cgctttctca tagctcacgc tgtaggtatc tcagttcggt gtaggtcgtt    4487
cgctccaagc tgggctgtgt gcacgaaccc cccgttcagc ccgaccgctg cgccttatcc    4547
ggtaactatc gtcttgagtc aacccggta agacacgact tatcgccact ggcagcagcc    4607
actggtaaca ggattagcag agcgaggtat gtaggcggtg ctacagagtt cttgaagtgg    4667
tggcctaact acggctacac tagaaggaca gtatttggta tctgcgctct gctgaagcca    4727
gttaccttcg gaaaaagagt tggtagctct tgatccggca acaaaccac cgctggtagc    4787
ggtggttttt ttgtttgcaa gcagcagatt acgcgcagaa aaaaaggatc tcaagaagat    4847
cctttgatct tttctacggg gtctgacgct cagtggaacg aaaactcacg ttaagggatt    4907
ttggtcatga gattatcaaa aaggatcttc acctagatcc ttttaccccg ttgataatc    4967
agaaaagccc caaaaacagg aagattgtat aagcaaatat ttaaattgta acgttaata    5027
ttttgttaaa attcgcgtta aattttttgtt aaatcagctc attttttaac caataggccg    5087
aaatcggcaa aatcccttat aaatcaaaag aatagcccga gatagggttg agtgttgttc    5147
cagtttggaa caagagtcca ctattaaaga acgtggactc caacgtcaaa gggcgaaaaa    5207
ccgtctatca gggcgatggc ccactacgtg aaccatcacc caaatcaagt tttttgggt    5267
cgaggtgccg taaagcacta atcggaacc ctaaagggag cccccgattt agagcttgac    5327
ggggaaagcc ggcgaacgtg gcgagaaagg aagggaagaa agcgaaagga gcgggcgcta    5387
gggcgctggc aagtgtagcg tcacgctgc gcgtaaccac cacacccgcc gcgcttaatg    5447
cgccgctaca gggcgcgtaa atcaatctaa agtatatatg agtaaacttg gtctgacagt    5507
taccaatgct taatcagtga ggcacctatc tcagcgatct gtctatttcg ttcatccata    5567
gttgcctgac tccccgtcgt gtagataact acgatacggg agggcttacc atctggcccc    5627
```

-continued

```
agtgctgcaa tgataccgcg agacccacgc tcaccggctc cagatttatc agcaataaac      5687
cagccagccg gaagggccga gcgcagaagt ggtcctgcaa ctttatccgc ctccatccag      5747
tctattaatt gttgccggga agctagagta agtagttcgc cagttaatag tttgcgcaac      5807
gttgttgcca ttgctgcagg catcgtggtg tcacgctcgt cgtttggtat ggcttcattc      5867
agctccggtt cccaacgatc aaggcgagtt acatgatccc ccatgttgtg caaaaaagcg      5927
gttagctcct tcggtcctcc gatcgttgtc agaagtaagt tggccgcagt gttatcactc      5987
atggttatgg cagcactgca taattctctt actgtcatgc catccgtaag atgcttttct      6047
gtgactggtg agtactcaac caagtcattc tgagaatagt gtatgcggcg accgagttgc      6107
tcttgcccgg cgtcaacacg ggataatacc gcgccacata gcagaacttt aaaagtgctc      6167
atcattggaa aacgttcttc ggggcgaaaa ctctcaagga tcttaccgct gttgagatcc      6227
agttcgatgt aacccactcg tgcacccaac tgatcttcag catctttac tttcaccagc       6287 gtttctgggt gagcaaaaac aggaaggcaa aatgccgcaa aaagggaat aagggcgaca       6347 cggaaatgtt gaatactcat actcttcctt tttcaatatt attgaagcat ttatcagggt      6407
tattgtctca tgagcggata catatttgaa tgtatttaga aaaataaaca ataggggtt       6467 ccgcgcacat ttccccgaaa agtgccacct gacgtctaag aaaccattat tatcatgaca      6527
ttaacctata aaataggcg tatcacgagg ccctttcgtc ttcaagaatt gatcgatcaa       6587
```

<210> SEQ ID NO 9
<211> LENGTH: 711
<212> TYPE: DNA
<213> ORGANISM: Artificial Sequence
<220> FEATURE:
<221> NAME/KEY: CDS
<222> LOCATION: (1)...(708)
<223> OTHER INFORMATION: Description of Artificial Sequence:/note =
      synthetic construct

<400> SEQUENCE: 9

```
agc aca aaa aag aaa cca tta aca caa gag cag ctt gag gac gca cgt          48
Ser Thr Lys Lys Lys Pro Leu Thr Gln Glu Gln Leu Glu Asp Ala Arg
  1               5                  10                  15 cgc ctt aaa gca att tat gaa aaa aag aaa aat gaa ctt ggc tta tcc          96
Arg Leu Lys Ala Ile Tyr Glu Lys Lys Lys Asn Glu Leu Gly Leu Ser
             20                  25                  30 cag gaa tct gtc gca gac aag atg ggg atg ggg cag tca ggc gtt ggt         144
Gln Glu Ser Val Ala Asp Lys Met Gly Met Gly Gln Ser Gly Val Gly
         35                  40                  45 gct tta ttt aat ggc atc aat gca tta aat gct tat aac gcg gca ttg         192
Ala Leu Phe Asn Gly Ile Asn Ala Leu Asn Ala Tyr Asn Ala Ala Leu
     50                  55                  60 cta gca aaa att ctc aaa gtt agc gtt gaa gaa ttc agc cct tca atc         240
Leu Ala Lys Ile Leu Lys Val Ser Val Glu Glu Phe Ser Pro Ser Ile
 65                  70                  75                  80 gct cga gaa atc tac gag atg tat gaa gcg gtt agc atg cag ccg tca         288
Ala Arg Glu Ile Tyr Glu Met Tyr Glu Ala Val Ser Met Gln Pro Ser
                 85                  90                  95 ctt aga agt gag tat gag tac cct gtt ttt tct cat gtt cag gca ggg         336
Leu Arg Ser Glu Tyr Glu Tyr Pro Val Phe Ser His Val Gln Ala Gly
            100                 105                 110 atg ttc tca cct aag ctt aga acc ttt acc aaa ggt gat gcg gag aga         384
Met Phe Ser Pro Lys Leu Arg Thr Phe Thr Lys Gly Asp Ala Glu Arg
        115                 120                 125 tgg gta agc aca acc aaa aaa gcc agt gat tct gca ttc tgg ctt gag         432
```

```
Trp Val Ser Thr Thr Lys Lys Ala Ser Asp Ser Ala Phe Trp Leu Glu
        130                 135                 140 gtt gaa ggt aat tcc atg acc gca cca aca ggc tcc aag cca agc ttt        480
Val Glu Gly Asn Ser Met Thr Ala Pro Thr Gly Ser Lys Pro Ser Phe
145                 150                 155                 160 cct gac gga atg tta att ctc gtt gac cct gag cag gct gtt gag cca        528
Pro Asp Gly Met Leu Ile Leu Val Asp Pro Glu Gln Ala Val Glu Pro
                165                 170                 175 ggt gat ttc tgc ata gcc aga ctt ggg ggt gat gag ttt acc ttc aag        576
Gly Asp Phe Cys Ile Ala Arg Leu Gly Gly Asp Glu Phe Thr Phe Lys
            180                 185                 190 aaa ctg atc agg gat agc ggt cag gtg ttt tta caa cca cta aac cca        624
Lys Leu Ile Arg Asp Ser Gly Gln Val Phe Leu Gln Pro Leu Asn Pro
        195                 200                 205 cag tac cca atg atc cca tgc aat gag agt tgt tcc gtt gtg ggg aaa        672
Gln Tyr Pro Met Ile Pro Cys Asn Glu Ser Cys Ser Val Val Gly Lys
    210                 215                 220 gtt atc gct agt cag tgg cct gaa gag acg ttt ggc tga                    711
Val Ile Ala Ser Gln Trp Pro Glu Glu Thr Phe Gly
225                 230                 235

<210> SEQ ID NO 10
<211> LENGTH: 276
<212> TYPE: DNA
<213> ORGANISM: Artificial Sequence
<220> FEATURE:
<221> NAME/KEY: CDS
<222> LOCATION: (1)...(276)
<223> OTHER INFORMATION: Description of Artificial Sequence:/note =
      synthetic construct

<400> SEQUENCE: 10 agc aca aaa aag aaa cca tta aca caa gag cag ctt gag gac gca cgt         48
Ser Thr Lys Lys Lys Pro Leu Thr Gln Glu Gln Leu Glu Asp Ala Arg
1               5                   10                  15 cgc ctt aaa gca att tat gaa aaa aag aaa aat gaa ctt ggc tta tcc         96
Arg Leu Lys Ala Ile Tyr Glu Lys Lys Lys Asn Glu Leu Gly Leu Ser
            20                  25                  30 cag gaa tct gtc gca gac aag atg ggg atg ggg cag tca ggc gtt ggt        144
Gln Glu Ser Val Ala Asp Lys Met Gly Met Gly Gln Ser Gly Val Gly
        35                  40                  45 gct tta ttt aat ggc atc aat gca tta aat gct tat aac gcg gca ttg        192
Ala Leu Phe Asn Gly Ile Asn Ala Leu Asn Ala Tyr Asn Ala Ala Leu
    50                  55                  60 cta gca aaa att ctc aaa gtt agc gtt gaa gaa ttc agc cct tca atc        240
Leu Ala Lys Ile Leu Lys Val Ser Val Glu Glu Phe Ser Pro Ser Ile
65                  70                  75                  80 gct cga gaa atc tac gag atg tat gaa gcg gtt agc                        276
Ala Arg Glu Ile Tyr Glu Met Tyr Glu Ala Val Ser
                85                  90

<210> SEQ ID NO 11
<211> LENGTH: 228
<212> TYPE: DNA
<213> ORGANISM: Artificial Sequence
<220> FEATURE:
<221> NAME/KEY: CDS
<222> LOCATION: (1)...(228)
<223> OTHER INFORMATION: Description of Artificial Sequence:/note =
      synthetic construct

<400> SEQUENCE: 11 agc aca aaa aag aaa cca tta aca caa gag cag ctt gag gac gca cgt         48
Ser Thr Lys Lys Lys Pro Leu Thr Gln Glu Gln Leu Glu Asp Ala Arg
```

```
                1               5                      10                     15
cgc ctt aaa gca att tat gaa aaa aag aaa aat gaa ctt ggc tta tcc           96
Arg Leu Lys Ala Ile Tyr Glu Lys Lys Lys Asn Glu Leu Gly Leu Ser
                        20                     25                     30 cag gaa tct gtc gca gac aag atg ggg atg ggg cag tca ggc gtt ggt         144
Gln Glu Ser Val Ala Asp Lys Met Gly Met Gly Gln Ser Gly Val Gly
                35                     40                     45 gct tta ttt aat ggc atc aat gca tta aat gct tat aac gcg gca ttg         192
Ala Leu Phe Asn Gly Ile Asn Ala Leu Asn Ala Tyr Asn Ala Ala Leu
        50                     55                     60 cta gca aaa att ctc aaa gtt agc gtt gaa gaa ttc                         228
Leu Ala Lys Ile Leu Lys Val Ser Val Glu Glu Phe
65                     70                     75

<210> SEQ ID NO 12
<211> LENGTH: 108
<212> TYPE: DNA
<213> ORGANISM: Artificial Sequence
<220> FEATURE:
<221> NAME/KEY: CDS
<222> LOCATION: (1)...(108)
<223> OTHER INFORMATION: Description of Artificial Sequence:/note =
      synthetic construct

<400> SEQUENCE: 12 agc aca aaa aag aaa cca tta aca caa gag cag ctt gag gac gca cgt          48
Ser Thr Lys Lys Lys Pro Leu Thr Gln Glu Gln Leu Glu Asp Ala Arg
1               5                      10                     15 cgc ctt aaa gca att tat gaa aaa aag aaa aat gaa ctt ggc tta tcc          96
Arg Leu Lys Ala Ile Tyr Glu Lys Lys Lys Asn Glu Leu Gly Leu Ser
                        20                     25                     30 cag gaa tct gtc                                                         108
Gln Glu Ser Val
                35

<210> SEQ ID NO 13
<211> LENGTH: 66
<212> TYPE: DNA
<213> ORGANISM: Artificial Sequence
<220> FEATURE:
<221> NAME/KEY: CDS
<222> LOCATION: (1)...(66)
<223> OTHER INFORMATION: Description of Artificial Sequence:/note =
      synthetic construct

<400> SEQUENCE: 13 agc aca aaa aag aaa cca tta aca caa gag cag ctt gag gac gca cgt          48
Ser Thr Lys Lys Lys Pro Leu Thr Gln Glu Gln Leu Glu Asp Ala Arg
1               5                      10                     15 cgc ctt aaa gca att tat                                                  66
Arg Leu Lys Ala Ile Tyr
                        20

<210> SEQ ID NO 14
<211> LENGTH: 45
<212> TYPE: DNA
<213> ORGANISM: Artificial Sequence
<220> FEATURE:
<221> NAME/KEY: CDS
<222> LOCATION: (1)...(45)
<223> OTHER INFORMATION: Description of Artificial Sequence:/note =
      synthetic construct

<400> SEQUENCE: 14 agc aca aaa aag aaa cca tta aca caa gag cag ctt gag gac gca              45
Ser Thr Lys Lys Lys Pro Leu Thr Gln Glu Gln Leu Glu Asp Ala
```

<210> SEQ ID NO 15
<211> LENGTH: 6
<212> TYPE: PRT
<213> ORGANISM: Artificial Sequence

<400> SEQUENCE: 15

Leu Val Pro Arg Gly Ser
 1               5

<210> SEQ ID NO 16
<211> LENGTH: 13
<212> TYPE: DNA
<213> ORGANISM: Artificial Sequence

<400> SEQUENCE: 16
aattcgcagc tca                                                        13

<210> SEQ ID NO 17
<211> LENGTH: 11
<212> TYPE: DNA
<213> ORGANISM: Artificial Sequence

<400> SEQUENCE: 17
tatgagctgc g                                                          11

<210> SEQ ID NO 18
<211> LENGTH: 18
<212> TYPE: DNA
<213> ORGANISM: Artificial Sequence

<400> SEQUENCE: 18
acatcagttg agcactgc                                                   18

<210> SEQ ID NO 19
<211> LENGTH: 27
<212> TYPE: DNA
<213> ORGANISM: Artificial Sequence

<400> SEQUENCE: 19
cctcgaggct tgctgataag gacgagc                                         27

<210> SEQ ID NO 20
<211> LENGTH: 28
<212> TYPE: DNA
<213> ORGANISM: Artificial Sequence

<400> SEQUENCE: 20
tcgaggcacc atcaccacca ccactgaa                                        28

<210> SEQ ID NO 21
<211> LENGTH: 28
<212> TYPE: DNA
<213> ORGANISM: Artificial Sequence

<400> SEQUENCE: 21
agctttcagt ggtggtggtg atggtgcc                                        28

<210> SEQ ID NO 22
<211> LENGTH: 18
<212> TYPE: DNA
<213> ORGANISM: Artificial Sequence -continued

```
<210> SEQ ID NO 22
```

<400> SEQUENCE: 22
tggctggcag tgctcgcc                                          18

<210> SEQ ID NO 23
<211> LENGTH: 30
<212> TYPE: DNA
<213> ORGANISM: Artificial Sequence

<400> SEQUENCE: 23
tcacctcgag gcctggcaaa acttccgaag                             30

<210> SEQ ID NO 24
<211> LENGTH: 26
<212> TYPE: DNA
<213> ORGANISM: Artificial Sequence

<400> SEQUENCE: 24
tcgaacggat ccgcgtggca ccaggc                                 26

<210> SEQ ID NO 25
<211> LENGTH: 18
<212> TYPE: DNA
<213> ORGANISM: Artificial Sequence

<400> SEQUENCE: 25
agcgctacct ctcgatcg                                          18

<210> SEQ ID NO 26
<211> LENGTH: 32
<212> TYPE: DNA
<213> ORGANISM: Artificial Sequence

<400> SEQUENCE: 26
gccgcactcg aggcaaggtc agcctgttta ct                          32

<210> SEQ ID NO 27
<211> LENGTH: 40
<212> TYPE: DNA
<213> ORGANISM: Artificial Sequence

<400> SEQUENCE: 27
tcgagccacc accaccacca ctctagactg gtgccacgcg                  40

<210> SEQ ID NO 28
<211> LENGTH: 43
<212> TYPE: DNA
<213> ORGANISM: Artificial Sequence

<400> SEQUENCE: 28
gatccgcgtg gcaccagtct agagtggtgg tggtggtggt ggc              43

<210> SEQ ID NO 29
<211> LENGTH: 31
<212> TYPE: DNA
<213> ORGANISM: Artificial Sequence

<400> SEQUENCE: 29
gcgccatatg gattataagt gtcaagtcca a                           31

<210> SEQ ID NO 30
<211> LENGTH: 32
<212> TYPE: DNA
<213> ORGANISM: Artificial Sequence

```
<400> SEQUENCE: 30
gccgctcgag gccaagccca cagatatttc ct                              32

<210> SEQ ID NO 31
<211> LENGTH: 39
<212> TYPE: DNA
<213> ORGANISM: Artificial Sequence

<400> SEQUENCE: 31
gcgcgaattc accatggaaa tgagacctgc tgtgacttc                       39

<210> SEQ ID NO 32
<211> LENGTH: 39
<212> TYPE: DNA
<213> ORGANISM: Artificial Sequence

<400> SEQUENCE: 32
ccgggctcga ggctagcagt gagtcatttg tactacaat                       39

<210> SEQ ID NO 33
<211> LENGTH: 35
<212> TYPE: DNA
<213> ORGANISM: Artificial Sequence

<400> SEQUENCE: 33
gggaattcca tatgttcaaa cacctccgaa gatgg                           35

<210> SEQ ID NO 34
<211> LENGTH: 35
<212> TYPE: DNA
<213> ORGANISM: Artificial Sequence

<400> SEQUENCE: 34
ccgctcgagg ccatctgggt gtcgtccgtt tcatc                           35

<210> SEQ ID NO 35
<211> LENGTH: 26
<212> TYPE: DNA
<213> ORGANISM: Artificial Sequence

<400> SEQUENCE: 35
gcgcgcatat ggctgccatc cggaag                                     26

<210> SEQ ID NO 36
<211> LENGTH: 30
<212> TYPE: DNA
<213> ORGANISM: Artificial Sequence

<400> SEQUENCE: 36
gccgctcgag gccaagacaa ggcaaccaga                                 30

<210> SEQ ID NO 37
<211> LENGTH: 26
<212> TYPE: DNA
<213> ORGANISM: Artificial Sequence

<400> SEQUENCE: 37
tcgagcctgg tgccacgcgg atccgt                                     26
```

METHODS AND COMPOSITIONS FOR HIGH YIELD PRODUCTION OF EUKARYOTIC PROTEINS

This application claims priority to U.S. provisional application Ser. No. 60/081,989, filed Apr. 16, 1998, and the Ser. No. 60/081,989 application is herein incorporated by this reference in its entirety.

This invention was made with government support under grant number DK46205 awarded by the National Institute of Diabetes and Digestive and Kidney Diseases and grant number GM15431 awarded by the National Institute of General Medical Sciences of the National Institutes of Health. The government has certain rights in the invention.

BACKGROUND OF THE INVENTION

1. Field of the Invention

The present invention relates to compositions and methods for the high yield production of eukaryotic proteins and in particular membrane proteins, by expression of recombinant vectors designed for such high yield production in bacterial cells.

2. Background Art

Certain classes of eukaryotic, prokaryotic and viral proteins, including membrane proteins, needed in large quantities for therapeutic uses as well as for biochemical and structural studies, have proven difficult to express in recombinant systems in sufficient yields. This is particularly difficult for eukaryotic proteins with multiple membrane spanning regions including, but not limited to, G-protein coupled receptors (QPCRs) and ion channels derived from eukaryotic cells (Goeddel, 1990).

Eukaryotic membrane proteins have been expressed in a number of eukaryotic systems including mammalian cells, baculovirus systems [up to 55 pmol/mg of protein (125 μg/L of culture); Loisel et al., 1997] and yeast cells (up to 14 pmol/mg membrane protein; Sander et al., 1994). However, none of these approaches has proven successful for the production of large quantities of purified eukaryotic proteins.

Furthermore, although a number of reports in the literature describe expression of eukaryotic membrane proteins such as GPCRs in prokaryotic cells (e.g., *E. coli*), none of these systems has proven capable of producing high levels of an intact eukaryotic protein (Table I). These bacterial cell systems have produced GPCRs in amounts of approximately several hundred receptor molecules per cell, with none of the systems producing greater than 300 receptors per cell, which corresponds to approximately 5 μg protein per liter of bacterial culture.

TABLE 1

Expression levels of β adrenergic receptor in *E. coli*

| Leader Sequence | Expression level |
|---|---|
| LamB | 33 to 225 receptors/cell (Chapot et al. 1990) |
| β-galactosidase | 25 receptors/cell (Marullo et al., 1988) |
| none | 200 receptors/levels (Breyer et al 1990) |

The present invention overcomes previous shortcomings associated with high yield production of eukaryotic proteins by providing compositions and methods for producing eukaryotic proteins and in particular, membrane proteins, in high yield (i.e., at least 100 μg protein/L of culture), for use in biochemical and structural studies and as therapeutic agents.

SUMMARY OF THE INVENTION

Figure 1:
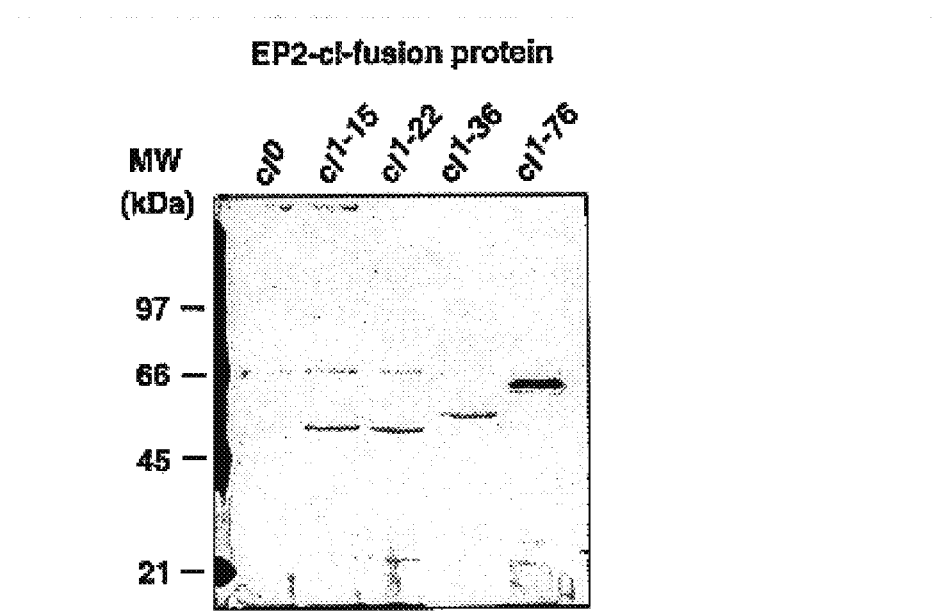
FIG. 1. Western blot analysis of $PGE_2EP_2$-cI-fusion proteins produced from nucleic acid constructs comprising: no leader sequence ($cI^0$); a leader sequence consisting of amino acids 1–15 of the lambda cI repressor protein ($cI^{1-15}$); a leader sequence consisting of amino acids 1–22 of the lambda cI repressor protein ($cI^{1-22}$); a leader sequence consisting of amino acids 1–36 of the lambda cI repressor protein ($cI^{1-36}$); and a leader sequence consisting of amino acids 1–76 of the lambda cI repressor protein ($cI^{1-76}$). The $PGE_2EP_2$-cI-fasion proteins were produced from a construct having a T7 promoter, nucleic acid encoding the leader sequences as described above and a nucleic acid encoding the $PGE_2EP_2$ protein. Proteins in nitrocellulose were blotted with an affinity-purified sheep anti-$PGE_2EP_2$ antibody and a secondary anti-sheep antibody conjugated to horse radish peroxidase and reacted with substrate according to standard methods to produce a luminescent reaction product.

The present invention provides an isolated nucleic acid comprising a first nucleotide sequence encoding an amino acid sequence comprising at least three positively charged amino acid residues, positioned upstream and in frame with a second nucleotide sequence encoding a protein.

In addition, the present invention provides an isolated nucleic acid comprising a first nucleotide sequence encoding a DNA binding protein, positioned upstream and in frame with a second nucleotide sequence encoding a protein.

An isolated nucleic acid is also provided which comprises a first nucleotide sequence encoding a bacteriophage lambda repressor protein, positioned upstream and in frame with a second nucleotide sequence encoding a protein.

Further provided in this invention is an isolated nucleic acid having the nucleotide sequence selected from the group consisting of SEQ ID NO:1, SEQ ID NO:2, SEQ ID NO:3, SEQ ID NO:4, SEQ ID NO:5, and SEQ ID NO:6.

The present invention further provides a method of producing a eukaryotic protein in a bacterial cell comprising: a) introducing the expression vector of this invention, wherein the second nucleotide sequence encodes a eukaryotic protein into the bacterial cell; and b) culturing the bacterial cell under conditions whereby the second nucleotide sequence of the expression vector is expressed to produce the eukaryotic protein.

A method of producing a eukaryotic protein in a bacterial cell in high yield is also provided, comprising: a) introducing the expression vector of this invention, wherein the second nucleotide sequence encodes a eukaryotic protein into the bacterial cell; and b) culturing the bacterial cell under conditions whereby the second nucleotide sequence of the expression vector is expressed to produce the eukaryotic protein in high yield.

Additionally, the present invention provides a method of producing a eukaryotic integral membrane protein in a bacterial cell comprising: a) introducing the expression vector of this invention, wherein the second nucleotide sequence encodes a eukaryotic integral membrane protein into the bacterial cell; and b) culturing the bacterial cell under conditions whereby the second nucleotide sequence of the expression vector is expressed to produce the eukaryotic integral membrane protein.

Furthermore, the present invention provides a method of producing a eukaryotic G-protein coupled receptor protein in a bacterial cell comprising: a) introducing the expression vector of this invention, wherein the second nucleotide sequence encodes a eukaryotic G-protein coupled receptor protein, into the bacterial cell; and b) culturing the bacterial cell under conditions whereby the second nucleotide sequence of the expression vector is expressed to produce the eukaryotic G-protein coupled receptor protein.

Additionally provided is a method of producing a eukaryotic ion channel protein in a bacterial cell comprising: a) introducing the expression vector of this invention, wherein the second nucleotide sequence encodes a eukaryotic ion channel protein into the bacterial cell; and b) culturing the bacterial cell under conditions whereby the second nucleotide sequence of the expression vector is expressed to produce the eukaryotic ion channel protein.

The present invention also provides a method of producing a rabbit prostaglandin (PG) $E_2$ $EP_3$ receptor protein in a bacterial cell comprising: a) introducing the expression vector of this invention, wherein the second nucleotide sequence encodes the rabbit prostaglandin $E_2$ $EP_3$ receptor protein, into the bacterial cell; and b) culturing the cell under conditions whereby the second nucleotide sequence of the expression vector is expressed to produce the rabbit prostaglandin $E_2$ $EP_3$ receptor protein.

The present invention further provides a method of producing a human prostaglandin $E_2$ $EP_2$ receptor protein in a bacterial cell comprising: a) introducing the expression vector of this invention, wherein the second nucleotide sequence encodes the human prostaglandin $E_2$ EP2 receptor protein, into the bacterial cell; and b) culturing the bacterial cell under conditions whereby the second nucleotide sequence of the expression vector is expressed to produce the human prostaglandin $E_2$ EP2 receptor protein.

Also provided is a method of producing a human chemokine receptor CCR-5 protein in a bacterial cell comprising: a) introducing the expression vector of this invention, wherein the second nucleotide sequence encodes the human chemokine receptor CCR-5 protein, into the bacterial cell; and b) culturing the bacterial cell under conditions whereby the second nucleotide sequence of the expression vector is expressed to produce the human chemokine receptor CCR-5 protein.

In addition, the present invention provides a method of producing a human $\beta_2$ adrenergic receptor protein in a bacterial cell comprising: a) introducing the expression vector of this invention, wherein the second nucleotide sequence encodes the human $\beta_2$ adrenergic receptor protein, into the bacterial cell; and b) culturing the bacterial cell under conditions whereby the second nucleotide sequence of the expression vector is expressed to produce the human $\beta_2$ adrenergic receptor protein.

The present invention further provides a method of producing a rat renal outer medullary $K^+$ channel protein in a bacterial cell comprising: a) introducing the expression vector of this invention, wherein the second nucleotide sequence encodes the rat renal outer medullary $K^+$ channel protein, into the bacterial cell; and b) culturing the bacterial cell under conditions whereby the second nucleotide sequence of the expression vector is expressed to produce the rat renal outer medullary $K^+$ channel protein.

Finally provided is a method of producing a human small G-protein rho protein in a bacterial cell comprising: a) introducing the expression vector of this invention, wherein the second nucleotide sequence encodes the small G-protein rho protein, into the bacterial cell; and b) culturing the bacterial cell under conditions whereby the second nucleotide sequence of the expression vector is expressed to produce the small G-protein rho protein.

Various other objectives and advantages of the present invention will become apparent from the following detailed description.

DETAILED DESCRIPTION OF THE INVENTION

As used herein, "a" or "an" can mean multiples. For example, "a cell" can mean at least one cell or more than one cell.

The present invention provides an isolated nucleic acid comprising a first nucleotide sequence encoding an amino acid sequence comprising at least three positively charged amino acid residues, positioned upstream and in frame with a second nucleotide sequence encoding a protein. As used herein, an "amino acid sequence comprising at least three positively charged residues" means an amino acid sequence having at least three and possibly more than three positively charged residues (e.g. arginine, lysine etc.) which can be consecutive, closely spaced, or randomly spaced. The amino acid sequence comprising at least three positively charged residues is the "leader sequence" of the fusion protein made by the methods of this invention. Neither the leader sequence nor the overall protein sequence (i.e., the leader sequence and the protein sequence together) need have a net positive charge, i.e., a pI value >7. The leader sequence can be as short as five amino acids (aa) long (e.g., 15 aa), although longer sequences (e.g., about 36 to 76 amino acids) are preferred. For example, the leader sequence of the fusion protein of this invention can comprise a nucleic acid encoding an amino acid sequence of a DNA binding protein, such as the bacteriophage lambda repressor protein.

Thus, the present invention further provides an isolated nucleic acid comprising a first nucleotide sequence encoding a DNA binding protein, positioned upstream and in frame with a second nucleotide sequence encoding a protein. As used herein, a "DNA binding protein" means a protein, which in its native setting, binds DNA and regulates its function. The DNA binding protein can be selected from the group consisting of eukaryotic DNA binding proteins, prokaryotic DNA binding proteins and bacteriophage-derived DNA binding proteins. For example, the DNA binding proteins of this invention can include, but are not limited to, bacteriophage DNA binding proteins such as lambda (λ) repressor, λ cro repressor, phage P22 arc repressor and phage P22 mnt repressor; bacterial DNA binding proteins such as the lac repressor and the trp repressor; eukaryotic binding proteins such as the yeast gal 4 protein; and mammalian transcription factors such as fos and jun as well as histones, transcriptional activators such as CREB and any other DNA binding protein now known or later identified.

It is also appreciated by one of skill in the art that DNA binding proteins can include fragments which retain at least three positively charged residues.

Also provided is an isolated nucleic acid comprising a first nucleotide sequence encoding a bacteriophage lambda repressor protein (having 236 amino acids, as shown in SEQ ID NO:9), positioned upstream and in frame with a second nucleotide sequence encoding a protein. In addition, the first nucleotide sequence of the nucleic acid of this invention can encode the N-terminal domain of the bacteriophage lambda repressor protein (having amino acids 1–92, as shown in SEQ ID NO:10), amino acids 1–76 (SEQ ID NO:11) of the bacteriophage lambda repressor protein, or at least 15 contiguous amino acids of the N-terminal domain of the bacteriophage lambda repressor protein.

The λ repressor protein is a product of the cI gene of bacteriophage λ. This gene encodes a protein of 236 amino acids organized into two domains, an N-terminal DNA binding domain consisting of amino acids 1–92 and a C-terminal domain consisting of amino acids ~114–236 (Sauer, 1978; Sauer et al., 1979).

In the nucleic acid of this invention as described above, the second nucleotide sequence can encode any protein which can be produced exogenously in a bacterial protein expression system. For example, the protein of this invention can be a viral protein, a prokaryotic protein or a eukaryotic protein. Viral proteins encoded by the second nucleotide sequence of the nucleic acid of this invention can include, but are not limited to, a homolog of the G-coupled receptor protein from cytomeaglovirus, herpesvirus 6, herpesvirus 7, Kaposi's sarcoma-associated herpesvirus (human herpesvirus 8), herpesvirus saimiri (e.g., the gene product ot ECRF3) human immuodeficiency virus (HIV) proteins gp120 and gp41, measles virus F protein, influenza hemagglutinin protein and herpesvirus B and H proteins. Prokaryotic proteins encoded by the second nucleotide sequence of the nucleic acid of this invention can include, but are not limited to, diacylglycerol kinase bacterial membrane protein and the lamB gene product. Eukaryotic proteins encoded by the second nucleotide sequence of the nucleic acid of the present invention can include, but are not limited to eukaryotic proteins selected from the group consisting of integral membrane proteins, G-protein coupled receptor (GPCR) proteins and ion channel proteins. Integral membrane proteins are proteins which have at least one hydrophobic amino acid sequence which passes through the membrane lipid bilayer as a transmembrane region or domain. GPCRs are a superfamily of integral membrane proteins which are widely distributed in eukaryotic cells and consist of seven transmembrane domains interconnected by a series of peptide loops. In their native environment, these proteins bind ligand from their exofacial surface and transmit signal to the intracellular side via heterotrimeric guanine-nucleotide binding proteins (G-proteins). Ion channel proteins are integral membrane proteins which, in their native environment, the plasma membrane of virtually all cell types, form a pore in the lipid bilayer which allows the selective passage of one or more ions, either into or out of the cell.

Furthermore, the second nucleotide sequence of the nucleic acid of this invention can encode a protein selected from the group consisting of rabbit prostaglandin $E_2EP_3$ receptor protein, human prostaglandin $E_2EP_2$ receptor protein, human chemokine receptor CCR-5 protein, human β2 adrenergic receptor protein, rat renal outer medullary $K^+$ channel protein and human small G-protein rho.

The present invention additionally provides an isolated nucleic acid having the nucleotide sequence selected from the group consisting of SEQ ID NO:1 (plasmid pLJM5.22His encoding the cI-77A his fusion protein), SEQ ID NO:2 (plasmid pCK2.5 HTL encoding cI-$EP_2$ histhrombin-lambda repressor C terminal domain aa 82–236), SEQ ID NO:3 (plasmid pSD1.63his encoding cI-CCR5 his), SEQ ID NO:4 (plasmid pSD1.18his encoding cI-βAR his), SEQ ID NO:5 (plasmidpSD1.134his encoding cI-ROMK his), and SEQ ID NO:6 (plasmid pSD2.46his encoding cI-rho his).

As used herein, "nucleic acid" refers to single- or double-stranded molecules which may be DNA, comprising two or more nucleotides comprised of the nucleotide bases A, T, C and G, or RNA, comprised of the bases A, U (substitute for T), C and G. The nucleic acid may represent a coding strand or its complement. Thus, the present invention also provides nucleic acids complementary to, or capable of, hybridizing with the nucleic acids of this invention. The nucleic acid of this invention may be a naturally occurring nucleic acid or the nucleic acid may be a synthetic nucleic acid sequence which contains alternative codons which encode the same amino acid as that which is found in a naturally occurring sequence (Lewin, 1994). Furthermore, the nucleic acids of this invention can include codons which encode amino acids which represent conservative substitutions of amino acids that do not alter the function of the protein, as are well known in the art.

As used herein, the term "isolated" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids (Michieli et al., 1996). The nucleic acids of this invention can be isolated from cells according to methods well known in the art. Alternatively, the nucleic acids of the present invention can be synthesized according to standard protocols well described in the literature.

The nucleic acid of this invention can be part of a recombinant nucleic acid comprising any combination of restriction sites and/or functional elements as are well known in the art which facilitate molecular cloning, expression, post-translational modifications and other recombinant DNA manipulations. For example, the nucleic acid of this invention encodes a leader sequence fused to a protein sequence to produce a fusion protein from which the leader sequence can be cleaved to yield only the protein sequence. Thus, nucleotide sequences which encode amino acid sequences which provide for the enzymatic or chemical cleavage of the leader peptide from the mature polypeptide, as well as regulatory sequences which allow temporal regulation of expression of the nucleic acid of this invention can also be included in the nucleic acid of this invention. Thus, the present invention further provides a recombinant nucleic acid comprising the nucleic acid of the present invention. In particular, the present invention provides a vector comprising the nucleic acid of this invention and a cell comprising the vector of this invention.

The vector of this invention can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols.

The vector of this invention is introduced into a bacterial cell under conditions whereby the resulting stable transformants maintain the vector, as are well known in the art and as described in the Examples provided herein.

The vector of this invention is introduced into a bacterial cell according to standard procedures for introducing nucleic acid into prokaryotes, as are well known in the art. There are numerous *E. coli* expression vectors known to one of ordinary skill in the art useful for the expression of proteins in prokaryotic systems. Other microbial hosts suitable for use include bacilli, such as *Bacillus subtilis* and other enterobacteria, such as Salmonella, Serratia and various Pseudomonas species. Expression vectors for prokaryotic systems typically contain expression control sequences compatible with the host cell (e.g., an origin of replication) and an antibiotic resistance marker to provide for the growth and selection of the expression vector in a bacterial host. In addition, any number of a variety of well-known promoters can be present, such as the T7 promoter system, the lactose promoter system, a typtophan (Trp) promoter system, a beta-lactamase promoter system, or a promoter system from phage lambda. The promoters will typically control expression, optionally with an operator sequence and have ribosome binding site sequences for example, for initiating and completing transcription and translation. The vector can also contain expression control sequences, enhancers that may regulate the transcriptional activity of the promoter, appropriate restriction sites to facilitate cloning of inserts adjacent to the promoter and other necessary information processing sites, such as RNA splice sites, polyadenylation sites and transcription termination sequences as well as any other sequence which may facilitate the expression of the inserted nucleic acid.

The nucleic acid in the vector of this invention can be expressed in cells after the nucleotide sequences have been operably linked to, i.e., positioned, to ensure the functioning of an expression control sequence. These expression vectors are typically replicable in the cells either as episomes or as an integral part of the cell's chromosomal DNA. Commonly, expression vectors can contain selection markers, e.g., tetracycline resistance, ampicillin resistance, kanamycin resistance or chlormaphenicol resistance, etc., to permit detection and/or selection of those bacterial cells transformed with the desired nucleic acid sequences (see, e.g., U.S. Pat. No. 4,704,362).

Thus, the present invention provides a method of producing a eukaryotic protein in a bacterial cell comprising: a) introducing the expression vector of this invention, wherein the second nucleotide sequence encodes a eukaryotic protein into the bacterial cell; and b) culturing the bacterial cell under conditions whereby the second nucleotide sequence of the expression vector is expressed to produce the eukaryotic protein.

A method of producing a eukaryotic protein in a bacterial cell in high yield is also provided, comprising: a) introducing the expression vector of this invention, wherein the second nucleotide sequence encodes a eukaryotic protein, into the bacterial cell; and b) culturing the bacterial cell under conditions whereby the second nucleotide sequence of the expression vector is expressed to produce the eukaryotic protein in high yield. As used herein, "high yield" means that the protein is produced in an amount which is at least, and preferably is greater than, 100 µg/liter of bacterial culture. More preferably, high yield means the protein is produced in an amount which is at least 0.5 mg/liter of culture and most preferably, the protein is produced in an amount which is at least 2.0 mg/liter of culture.

In addition, the present invention provides a method of producing a eukaryotic integral membrane protein in a bacterial cell comprising: a) producing the expression vector of this invention, wherein the second nucleotide sequence encodes a eukaryotic integral membrane protein; b) introducing the vector into the bacterial cell; and c) culturing the bacterial cell under conditions whereby the second nucleotide sequence of the expression vector is expressed to produce the eukaryotic integral membrane protein.

The present invention also provides a method of producing a eukaryotic G-protein coupled receptor protein in a bacterial cell comprising: a) introducing the expression vector of this invention, wherein the second nucleotide sequence encodes a eukaryotic G-protein coupled receptor protein, into the bacterial cell; and b) culturing the bacterial cell under conditions whereby the second nucleotide sequence of the expression vector is expressed to produce the eukaryotic G-protein coupled receptor protein.

Additionally, the present invention provides a method of producing a eukaryotic ion channel protein in a bacterial cell comprising: a) introducing the expression vector of this invention, wherein the second nucleotide sequence encodes a eukaryotic ion channel protein, into the bacterial cell; and b) culturing the bacterial cell under conditions whereby the second nucleotide sequence of the expression vector is expressed to produce the eukaryotic ion channel protein.

Furthermore, the present invention provides methods for the production of specific eukaryotic proteins. In particular, the present invention provides a method of producing a rabbit prostaglandin $E_2$ $EP_3$ receptor protein in a bacterial cell comprising: a) introducing the expression vector of this invention, wherein the second nucleotide sequence encodes the rabbit prostaglandin $E_2$ $EP_3$ receptor protein, into the bacterial cell; and b) culturing the cell under conditions whereby the second nucleotide sequence of the expression vector is expressed to produce the rabbit prostaglandin $E_2$ $EP_3$ receptor protein. The rabbit $PGE_2EP_3$ receptor protein is a member of the family of GPCRs, which in its native environment (e.g., the plasma membrane of cells in the kidney, stomach and adrenal glands, among others), binds prostaglandin $E_2$ and elicits intracellular signals (Breyer, et al., 1994) on the intracellular side via heterotrimeric guanine-nucleotide binding proteins (G-proteins).

Also provided is a method of producing a human prostaglandin $E_2$ $EP_2$ receptor protein in a bacterial cell comprising: a) introducing the expression vector of this invention, wherein the second nucleotide sequence encodes the human prostaglandin $E_2$ $EP_2$ receptor protein, into the bacterial cell; and b) culturing the bacterial cell under conditions whereby the second nucleotide sequence of the expression vector is expressed to produce the human prostaglandin $E_2$ $EP_2$ receptor protein. The human $PGE_2$ $EP_2$ receptor is a member of the family of GPCRs which, in its native environment (e.g., the plasma membrane of cells in the lung, uterus and blood cells, among others), binds prostaglandin $E_2$ and elicits intracellular signals on the intracellular side via heterotrimeric guanine-nucleotide binding proteins (G-proteins).

Further provided is a method of producing a human chemokine receptor CCR-5 protein in a bacterial cell comprising: a) introducing the expression vector of this invention, wherein the second nucleotide sequence encodes the human chemokine receptor CCR-5 protein, into the bacterial cell; and b) culturing the bacterial cell under conditions whereby the second nucleotide sequence of the expression vector is expressed to produce the human chemokine receptor CCR-5 protein. The human chemokine receptor CCR-5 (alternatively named CC-CKR5) is a member of the family of GPCRs which, in its native environment (the plasma membrane of T cells and macrophages, among others), binds chemokine peptide hormones on the exofacial surface of the cell and elicits intracellular signals on the intracellular side of the plasma membrane via heterotrimeric guanine-nucleotide binding proteins (G-proteins). In addition, CCR-5 is utilized by the human immunodeficiency virus (HIV) virus as a co-receptor which facilitates viral entry into the host cell during the pathogenesis of viral infection.

Production of the chemokine receptor protein, CCR-5, in high yield provides for a number of therapeutic uses. For example, the CCR-5 protein can be used as an inunumogen to develop autoantibodies to the CCR-5 protein. This active immunization would then inhibit HIV entry into target cells expressing the CCR-5 receptor. Alternatively, the CCR-5 protein can be used for passive immunization wherein an animal (e.g., a horse) can be immunized with the CCR-5 fusion protein of this invention and the resulting antiserum collected and purified. The horse Ig anti-CCR-5 fusion protein fraction can then be administered to humans to inhibit HIV entry into target cells expressing the CCR-5 receptor. A third use of the CCR-5 protein can be to administer the CCR-5 protein of this invention into a subject infected with HIV in an amount which can bind to HIV in the subject and inactivate it.

In addition, the present invention provides a method of producing a human $\beta_2$ adrenergic receptor protein in a bacterial cell comprising: a) introducing the expression vector of this invention, wherein the second nucleotide sequence encodes the human β2 adrenergic receptor protein, into the bacterial cell; and b) culturing the bacterial cell under conditions whereby the second nucleotide sequence of the expression vector is expressed to produce the human $\beta_2$ adrenergic receptor protein. The human $\beta_2$ adrenergic receptor is a member of the family of GPCRs which, in its native environment (the plasma membrane of cells in the heart, lungs, blood vessels, intestine and other organs and tissues), binds epinephrine and its natural and synthetic analogs on their exofacial surface and elicits intracellular signals on the intracellular side via heterotrimeric guanine-nucleotide binding proteins (G-proteins).

Furthermore, the present invention provides a method of producing a rat renal outer medullary $K^+$ channel (ROMK) protein in a bacterial cell comprising: a) introducing the expression vector of this invention, wherein the second nucleotide sequence encodes the rat renal outer medullary $K^+$ channel protein, into the bacterial cell; and b) culturing the bacterial cell under conditions whereby the second nucleotide sequence of the expression vector is expressed to produce the rat renal outer medullary $K^+$ channel protein. ROMK is a member of the family of ion channel proteins which, in its native environment (the plasma membrane of cells in the kidney, brain, heart and stomach), allows the selective secretion of potassium ions from the intracellular milieu.

The present invention also provides a method of producing a human small G-protein rho protein in a bacterial cell comprising: a) producing the expression vector of this invention, wherein the second nucleotide sequence encodes the small G-protein rho protein; b) introducing the vector into the bacterial cell; and c) culturing the bacterial cell under conditions whereby the second nucleotide sequence of the expression vector is expressed to produce the small G-protein rho protein. The protein rho is a member of the family of "small GTP binding proteins" which, in its native environment, is a membrane associated protein but is not an integral membrane protein i.e., it does not contain any transmembrane regions.

The methods of this invention can further comprise the step of isolating and purifying the protein according to methods well known in the art and as described herein (see, e.g., Sambrook et al.). Additionally, for all of the methods of the present invention, the eukaryotic protein which is produced can be produced in high yield, as defined herein.

The proteins produced by the methods of this invention can be cleaved from the leader sequence as described herein, re-folded and tested for functionality. For example, the proteins of this invention can be refolded according to methods well known in the art for refolding membrane proteins (see, e.g., Braiman et al., 1987). Briefly, the inclusion bodies containing the fusion protein of this invention can be isolated from the bacterial cells in which they were produced and solubilized in buffer containing 0.2% sodium dodecyl sulfate (SDS). The fusion proteins can then be mixed with buffer containing dimyristoyl phosphatidyl choline (DMPC) and CHAPS detergent, to allow for the renaturation of the detergent-solubilized protein.

The proteins of this invention can be tested for functionality by a variety of methods. For example, the presence of antigenic epitopes and ability of the proteins to bind ligands can be determined by Western blot assays, fluorescence cell sorting assays, inununoprecipitation, immunochemical assays and/or competitive binding assays, as well as any other assay which measures specific binding activity.

For ion channel proteins of this invention, the proteins can be reconstituted into artificial lipid bilayers (so-called black lipid bilayers) according to methods well known in the art. The ability of the ion channel to function can then be tested electrophysiologically, using direct current/voltage measurements according to well known methods (Zweifach et al., 1991). Alternatively, the ion channel can be incorporated into liposomes according to standard methods, and activity can be monitored by the ability of ion fluxes to change the fluorescence of indicator dyes contained within the liposomes, as known in the art (Le Caherec et al., 1996; Zeidel et al., 1992).

GPCRs can be tested for functionality by testing them for the ability to bind radiolabeled ligand in a specific and saturable manner, as is well known in the art (Limbird, 1996). Moreover, activation of GPCRs leads to a concomitant increase in enzymatic activity by GTP binding proteins (increased turnover of GTP to GDP). The GPCRs of this invention can also be reconstituted with purified heteromeric G-proteins in liposomes and the rate of GTP hydrolysis upon addition of the cognate agonist can be measured according to well known methods. An increase in rate indicates a properly folded and functioning protein.

The proteins of this invention can be used in a number of practical applications including, but not limited to:

1. Immunization with recombinant host protein antigen as a viral/pathogen antagonist.
2. Production of membrane proteins for diagnostic or screening assays.
3. Production of membrane proteins for biochemical studies.
4. Production of membrane protein for structural studies.
5. Antigen production for generation of antibodies for immuno-histochemical mapping, including mapping of orphan receptors and ion channels.

In particular, the proteins of this invention can be used as immunogens in vaccine protocols and as antigens for the production of monoclonal and polyclonal antibodies according to methods standard in the art (see, e.g., Harlow and Lane, 1988). Additionally, the proteins of this invention can be used in diagnostic and screening assays to detect the presence of a ligand which binds the protein of this invention, in a biological sample from a subject. Such assays can be carried out by detecting the binding of the protein with a ligand in the sample. Such detection methods can include identifying the formation of a protein/ligand complex with detectable antibodies which specifically bind the protein and/ or the ligand as well as by competitive binding assays as are well known in the art.

The present invention is more particularly described in the following examples which are intended as illustrative only since numerous modifications and variations therein will be apparent to those skilled in the art.

EXAMPLES

Example 1

Plasmid pLJM5-22H—Fusion of Rabbit $EP_3$ Receptor with the N-terminal Domain of λ Repressor Construction of cI-77A fusion *E. coli* expression vector—Plasmid pLJM5-22H (SEQ ID NO:1) consists of the first 231 bp of a semi-synthetic cI gene (Breyer and Sauer, 1989a), encoding amino acids 1–76 (SEQ ID NO:11), fused to the N-terminal of the $EP_3$ receptor 77A splice variant. It should be noted that the numbering convention for the λ-repressor protein designates serine encoded at codon 2 of the cI gene as position 1 because the N-terminal methionine is cleaved in the mature λ-repressor protein. It is not known whether the cleavage of the initiator methionine occurs in the fusion proteins, however the convention designating serine as amino acid 1 is utilized for the various fusion proteins described below.

The C-terminus of the 77A protein was modified to remove the stop codon, and an XhoI restriction site was introduced immediately 3' to the coding region allowing a C-terminal fusion. The vector, ptac promoter and synthetic cI gene sequences were derived from the plasmid pRB200 (Breyer and Sauer, 1989a). Internal EcoRI and XhoI sites in the synthetic cI gene were digested and the 77A cDNA was inserted as follows to produce the plasmid: an EcoRI/NdeI adapter pair [5'-AATTCGCAGCTCA-3' (SEQ ID NO:16) and 5'-TATGAGCTGCG 3' (SEQ ID NO:17)] was used to fuse the initiator methionine of 77A from plasmid pRC/CMV 77A wt (Audoly and Breyer, 1997) in frame with amino acid 76 of the cI sequence. The 3' end of the 77A cDNA was modified by PCR, removing the TGA stop codon and the 3' untranslated region. An XhoI restriction site was simultaneously introduced allowing fusion to a C-terminal 6x-his tag. The sequence of the sense primer, 5'-ACA TCA GTT GAG CAC TGC-3' (SEQ ID NO:18) lies within the 77A coding region. The antisense primer 5'-CCT CGA GGC TTG CTG ATA AGG ACG AGC-3' (SEQ ID NO:19) lies at the 3' end of the coding region. PCR was performed with Vent DNA polymerase for 30 cycles of 94° C. for 15 sec, 51° C. for 15 sec and 72° C. for 30 sec. The PCR fragment was digested with BsmI (a restriction site internal to 77A) and XhoI and ligated into the 77A cDNA backbone reconstituting the fall length 77A cDNA with an XhoI site at the 3' end of the coding region. This plasmid was digested at the XhoI site and a HindIII site 3' to the EP coding region. The his tag linker oligonucleotide sequences 5' TCG AGG CAC CAT CAC CAC CAC CAC TGA A 3' (SEQ ID NO:20) and 5' AGC TTT CAG TGG TGG TGG TGA TGG TGC C 3' (SEQ ID NO:21) oligonucleotides encoding a 6xhis tag were ligated to the backbone, allowing fusion to a C-terminal 6xhis tag used for affinity purification.

The NT No-Tail) $EP_3$ receptor expression construct, which lacks the C-terminal sequence encoded by the alternatively spliced variable sequence of the 77A splice variant, was generated by PCR using the 77A cDNA as a template. The receptor sequence ends at $Q^{355}$, 10 residues distal to the end of transmembrane VII, and is fused to the 6xhis tag at the C-terminus. A PCR fragment was generated using a sense internal primer at nt 532 of the coding region (5'-TGG CTG GCA GTG CTC GCC-3') (SEQ ID NO:22) and a downstream primer (5'-TCA CCT CGA GGC CTG GCA AAA CTT CCG AAG-3') (SEQ ID NO:23) which inserts an XhoI site immediately distal to nt 1065 ($Q^{355}$), allowing amplification of a 534 bp fragment. The PCR was performed with Vent DNA polymerase for 35 cycles of 98° C. for 15 sec, 57° C. for 15 sec and 72° C. for 60 sec. This PCR product was digested at internal SacI and XhoI restriction sites and the resulting fragment was subcloned into the SacI and XhoI sites in expression vector pLJM5-22H to yield the plasmid pLJM6-09 (SEQ ID NO:7) which expresses the cI-NT-his fusion protein.

Plasmid pLJM5-42T (SEQ ID NO:8) expresses a third variant of the 77A protein, cI-77A-TL. In addition to the N-terminal $cI^{1-76}$ fusion, the cI-77A-TL construct (for Thrombin-Lambda C-terminal fusion) is fused to amino acids 82–236 of the cI gene utilizing a thrombin cleavage site linker between the C-terminal sequence of 77A and the lambda C-terminal fusion. The thrombin cleavage sequence LVPRGS (SEQ ID NO:22), allows cleavage of the C-terminal fusion from the purified recombinant protein. This construct was made by inserting the oligonucleotide pair 5' TCG AGC CTG GTG CCA CGC GGA TCC GT 3' (SEQ ID NO:37) and 5' TCG AAC GGA TCC GCG TGG CAC CAG GC 3' (SEQ ID NO:24) into the XhoI site at the 3' end of the 77A fragment outlined above. This allows an in-frame fusion of the 77A receptor to the thrombin cleavage sequence followed by amino acids 82–236 of the cI gene. This thrombin cleavage sequence or similar sequences (e.g. enterokinase) can be inserted between the N-terminal $cI^{1-76}$ fusion as well, allowing the isolation of protein products which lack the fusion peptides.

Induction of cI-$EP_3$ fusion protein expression. *E. coli* strain DH5α cells transformed with various expression plasmids was grown in 2×LB medium containing 100 μg/ml of ampicillin (2×LBA100). Cells were grown in 2×LBA100 with shaking at 37° C. until the culture reached an $A_{600}$ of 0.8. Protein expression was induced by addition of 1 mM isopropyl β-thiogalactoside (IPTG), followed by a further incubation at 30° C. for 5 hours. Cells were harvested by centrifugation at 2,500×g, flash frozen in liquid nitrogen and stored at −80° C.

Protein Purification by Ni-NTA Column—Bacterial cell pellets were resuspended in Buffer 1 (50 mM Tris Cl, 150 mM Na Cl, 0.1% $NaN_3$, 10 mM CHAPS, 20% glycerol, 2 mM PMSF, 1.4 mM β-ME, pH 8.0) followed by sonication three times for 20 sec, on ice. The inclusion bodies were collected by centrifugation at 35,000×g for 20 min at 4° C. The supernatant was discarded and the inclusion bodies were washed two more times with Buffer 1 using the same centrifugation protocol. Washed inclusion bodies were dissolved in Buffer 2 (50 mm Tris Cl, 500 mM Na Cl, 1% NP-40, 0.5 % Na deoxycholate, 2 mM PMSF, 2 M urea, 20 mM imidazole, pH 8.0). Ni-NTA agarose beads were added and incubated at 4° C. overnight on a rotary shaker. Agarose beads were collected by centrifugation at 1000×g for 2 min, and batch washed with 50 volumes of Buffer 2. After three washes, the fusion protein was batch eluted with Buffer 3 (50 mM Tris Cl, 500 mM Na Cl, 1% NP-40, 0.5% Na deoxycholate, 2 mM PMSF, 2 M urea, 100 mM imidazole, pH 8.0). Eluate was dialyzed against Buffer 2 and purified a second time on Ni-NTA beads as described above.

Quantitation of Protein. Purified protein was quantitated using the BCA protein assay (Pierce). Estimates of the specific content of $EP_3$ fusion protein in the lysate were made utilizing a "dot-blot" immuno-assay employing the 24H monoclonal antibody directed against the N-terminal domain of the fusion partner. The dot blot assay was performed as follows: Bacterial cells expressing the cI-fusion protein were induced for the required time at the appropriate temperature with 1 mM IPTG. The lysate was fractionated to obtain the following fractions: cell lysate, cytosol, washed inclusion bodies, solubilized inclusion bodies and Ni-NTA purified protein. One µl of the various purification fractions containing the expressed cI-fasion protein were "spotted" onto nitrocellulose filters and allowed to air dry. Additionally, 1 µl volumes of a range of known amounts of purified fusion protein, the concentration of which was determined by BCA assay, were spotted as a standard curve. The dried blot was then processed for immuno-detection: the blot was washed with Tween 20 containing Tris buffered Saline (TBS-T) for 10 min followed by a 1 hr blocking step using TBS-T containing 5% (w/v) skim minlk. The blot was then rinsed briefly with TBS-T and incubated overnight at 4° C. with TBS-T containing 2% skim milk with an appropriate dilution of mouse 24H antibody. The blot was then washed and incubated with horseradish peroxidase-conjugated goat anti-mouse IgG. The blot was subsequently washed 3×10 min with TBS-T and a chemiluminescence reaction was performed according to the manufacturer's instructions (SuperSignal substrate, Pierce). Intensity of each dot was compared to the known standard by densitometry. Overall yield of the expression/purification was calculated by factoring in corrections for volume of each fraction.

Production of anti-fusion protein antibodies. The purified fusion protein of this invention can be used to raise specific antibodies (either monoclonal or polyclonal) against the expressed protein according to protocols well known in the art. In the case of the $EP_3$ receptor, the purified cI-77A-his protein was injected into goats. The first injection was made subcutaneously with 0.5 mg of recombinant protein in Complete Freunds' adjuvant. Subsequent boost immunizations were made subcutaneously with 0.25 mg of recombinant protein in Incomplete Freunds' adjuvant. Antiserum was "depleted" by incubation with E. coli lysate expressing the intact cI gene which had been covalently coupled to the CNBr activated Sepharose resin. This incubation removes or depletes antibodies directed against the cI fusion partner sequence as well as any antibodies raised to E. coli proteins from either natural infection or present as minor contaminants in the immunogen. The supernatant retains antibodies to the partner $EP_3$ protein. The resulting depleted antiserum may be further purified by adsorption to the purified cI-77A-his protein antigen coupled to CNBr Sepharose. Purified antibody is subsequently eluted from the resin and can be utilized, for example, in immunodetection assays to identify the $EP_3$ protein in native tissues or from recombinant sources.

Ligand Binding Studies—The fusion proteins of the present invention can be refolded as described herein and used in a variety of assays, such as ligand binding studies. For example, the refolded fusion proteins can be used to screen drugs in a variety of assays as are well known to one of skill in the art. For example, on the basis that HIV must interact with CCR-5 to gain entry into cells, substances can be screened for antiviral activity by detecting the ability of the substance to block the binding to the HIV gp120 coat protein to the CCR-5 receptor protein of this invention. Plastic microtiter plates can be coated with the CCR-5 protein and radiolabeled HIV gp120 coat protein (which can be complexed with recombinant CD-4, the co-receptor) can be added in the presence of the substance to be screened for antiviral activity. The amount of radioactive gp120 coat protein bound to the plate in the absence and presence of the substance can be determined according to standard methods. A decrease in or absence of bound gp120 as determined by quantitating the radioactive signal indicates a substance having the ability to inhibit binding of the HIV gp120 coat protein to the CCR-5 receptor protein, thereby identifying a substance potentially having antiviral activity. The substance can then be farther screened for specific antiviral activity according to protocols well known in the art.

The protein of this invention can also be used in saturation binding isotherm experiments. For example, the recombinant membrane protein of this invention is incubated in binding buffer (25 mM $KPO_4$, pH 6.2, 10 mM $MgCl_2$, and 1 mM EDTA) for 2 h at 30° C. with varying concentrations of [$^3$H] $PGE_2$. Nonspecific binding is determined in the presence of 50 µM unlabeled $PGE_2$. Reactions are stopped by rapid filtration on Whatmnan GF/F glass fiber filters as described previously (Breyer, et al., 1994). Filters are washed three times with binding buffer, dried, and counted in Dupont 989 fluor.

Expression of cI-77A-his fusion protein—The vector pLJM5-22H has the tac promoter and the cI translation initiator sequences. The cDNA encoding the 77A splice variant of the $EP_3$ receptor was modified as described above to obtain an $EP_3$ receptor fused to a portion of the cI gene (1–76 aa) at the N-terminus and a C-terminal fusion to a 6×his tag. The resultant fusion protein of 501 aa has a predicted molecular weight 55.4 kDa. When expressed in E. coli this construct demonstrated high levels of expression of a protein of apparent molecular weight of 50 kDa in whole cell lysates when resolved by SDS-PAGE. Expression levels of the cI-77A-his fusion protein were estimated to be in the range of 20 mg/L of E. coli culture as determined by dot-blot assay as described herein.

A second fusion protein cI-NT (No Tail)-his, in which the C-terminal tail amino acids 356 to 411 of the 77A protein were deleted, was also constructed. The cI-NT-his protein expressed by this construct lacks the epitope to which the anti-peptide antibody was generated and thus served as a control for the anti tail-peptide antibody in Western blot experiments. A third construct fused the C-terminus of lambda repressor, residues 82–236, to the C-terminus of the cI-77A fusion via a thrombin cleavage site linker. This protein designated cI-77A-TL (Thrombin-Lambda) tested the hypothesis that the C-terminal sequence of E. coli expressed proteins are important determinants of protein degradation. Because lambda repressor is highly expressed in E. coli, its C-terminus might be resistant to degradation by C-terminal directed proteases. Coomasie blue and Western blot analysis of the lysates resolved by SDS-PAGE demonstrated that the induced protein of the appropriate molecular weight was reactive with the 24H antibody for each of the $EP_3$ constructs tested. This 24H monoclonal Ab was generated against the N-terminal 102 amino acids of the cI gene and its recognition sequence is contained within the first 36 amino acids of the antigen (Breyer and Sauer, 1989b).

Western blot analysis was also performed with an antibody raised against the unique sequence in the 77A cDNA as described herein. A protein of 50 kDa was detected for the cI-77A-his lysate, and a protein of 68 kDa was detected for the cI-77A-TL but neither the cI containing lysate nor the cI-NT-his, in which the target epitope had been deleted, displayed any reactivity.

Purification of cI-77A-his fusion protein. When the plasmid encoding the cI-77A-his fusion protein was expressed in E. coli, the majority of the cI-77A-his fusion protein produced was found in the insoluble fraction comprising the "inclusion bodies." Precipitation of a protein into inclusion bodies can be advantageous because the precipitated protein is subjected to minimal proteolysis and can be recovered as a partially pure aggregate. Moreover, mammalian membrane proteins can be toxic when expressed in E. coli membrane and sequestration of the PGE$_2$EP$_3$ receptor in inclusion bodies can remove some of the selective disadvantage of PGE$_2$EP3 overexpression.

Inclusion bodies were collected by centrifugation, which separated them from the majority of soluble protein contaminants. The inclusion bodies were washed extensively in the presence of CHAPS, with only a small loss of cI-77A-his. The washed inclusion bodies were solubilized in 2M urea in the presence of NP-40 and deoxycholate. Solubilized cI-77A-his was then purified by affinity chromatography using Ni-NTA agarose resin in buffer containing 2M urea, NP-40 and deoxycholate. After a second round of affinity purification on the Ni-NTA resin, the cI-77A-his was purified to apparent homogeneity as determined by silver staining, with a yield of approximately 10% of the initial protein expressed or approximately 2 mg protein purified per liter of bacterial culture.

EXAMPLE 2

Plasmid pCK2-5HTL—Fusion of the Human EP$_2$ Receptor with the N-terminal Domain of λ Repressor Construction of cI-EP$_2$ HTL fusion E. coli expression vector. Plasmid pCK2-5HTL (SEQ ID NO:2) consists of the first 231 bp of a semi-synthetic cI gene (Breyer and Sauer, 1989a), encoding amino acids 1–76, fused to the N-terminus of the E-Prostanoid receptor, EP$_2$. The human EP$_2$ open reading frame was inserted into a plasmid derivative of pRB200 between the EcoRI and XhoI sites by fusing it to the 3' end of the sequence encoding the first 76 amino acids of lambda repressor using the EcoRI restriction enzyme site thereby creating pCK1-23. The stop codon of the human EP$_2$ receptor was removed from the hEP$_2$ sequence by PCR. Briefly, the upstream oligonucleotide primer, originating from position 398 of the hEP$_2$ ORF, 5'-AGC GCT ACC TCT CGA TCG-3' (SEQ ID NO:25), along with the downstream oligonucleotide primer, directed against the most 3' region of hEP$_2$ ORF, 5'-GCC GCA CTC GAG GCA AGG TCA GCC TGT TTA CT-3' (SEQ ID NO:26), were used in conjunction with VENT polymerase to amplify a new fragment lacking the stop codon from the hEP$_2$ ORF template (underlined sequence represents an XhoI site). Reaction conditions were carried out using 30 cycles of the following protocol: 1 min at 95° C., 15 sec at 98° C., 30 sec at 53° C. followed by 1 min at 72° C. The amplified product of 677 bp was digested at internal Bsu 36I and Xho I sites and the appropriate fragment subdloned into the plasmid pCK-1-23 to create the intermediate plasmid, pCK-1-38. Next, an oligonucleotide linker was synthesized to fuse the C-terminal portion of lambda repressor, in frame with the hEP$_2$ sequence. The sequence of this linker contains a thrombin cleavage site (aa sequence LVPRGS; SEQ ID NO:15), introduces a BamHI restriction site and begins with a 6×histidine tag. The two oligonucleotides, 5'-TCG AGC CAC CAC CAC CAC CAC CAC TCT AGA CTG GTG CCA CGC G-3' (SEQ ID NO:27) and 5'-GAT CCG CGT GGC ACC AGT CTA GAG TGG TGG TGG TGG TGG TGG C-3' (SEQ ID NO:28), were annealed together at 65° C. and subdloned into pCK-1-38 following its digestion with Xho I and Bam HI, thereby creating the plasmid, CK2-5-HTL. The underlined sequences represent the histidine tag, while those in bold refer to the thrombin cleavage site.

Induction of cI-EP$_2$-HTL fusion protein expression—E. coli strain DH5α cells transformed with the pCK2-5-HTL expression plasmids were grown in 2×LB medium containing 100 µg/ml of ampicillin (2×LBA100). Cells were grown in 2×LBA100 with shaking at 37° C. until the culture reached an A$_{600}$ of 0.8. Protein expression was induced by addition of 1 mM isopropyl β-thiogalactoside (IPTG), followed by a further incubation at 30° C. for 5 hours. Then the cells were harvested by centrifugation at 2,500×g, flash frozen in liquid nitrogen and stored at −80° C.

Protein Purification by Ni-NTA Column—Bacterial cell pellets were resuspended in Buffer 1(50 mM Tris Cl, 150 mM Na Cl, 0.1% NaN3, 10 mM CHAPS, 20% glycerol, 2 mM PMSF, 1.4 mM β-ME, pH 8.0) followed by sonication three times for 20 sec, on ice. The protein was purified from inclusion bodies as described above for the cI-EP$_3$-his protein.

Expression of cI-EP$_2$-HTL fusion protein—The vector pCK2-5-HTL has the tac promoter and the cI translation initiator sequences. The cDNA encoding the human EP$_2$ receptor was modified as described above for the EP$_3$ receptor to obtain an EP$_2$ receptor fused to a portion of the cI gene (1–76 aa) at the N-terminus and a C-terminal fusion to a 6×his tag, followed by the thrombin cleavage site fused to amino acids 82–236 of λ-repressor. The resultant fusion protein of 610 aa has a predicted molecular weight 67.5 kDa. When expressed in E. coli this construct demonstrated high levels of expression of a protein of apparent molecular weight of 60 kDa in whole cell lysates when resolved by SDS-PAGE. The expression levels of the cI-EP$_2$-HTL fusion protein were estimated to be in the range of 20 mg/L of E. coli culture. Western blot analysis of the lysates demonstrated that the induced protein of the appropriate molecular weight was reactive with the 24H antibody for EP$_2$ constructs tested.

Analysis of fusion of the EP$_2$ receptor to variable length cI leader sequences. To test the applicability of different bacterial promoters, while simultaneously assessing the limit to which the N-terminal sequence may be truncated, the human EP$_2$ receptor was fused to the bacteriophage T7 promoter with N-terminal fusion sequences of 0, 15, 36 and 76 aa of the N-terminus of cI. Induction of each of these fusion proteins was achieved by the addition of IPTG and the ability of each construct to express protein was assessed by Western blot. Initially, the N-terminal 76 aa of the cI gene were fused to the EP$_2$ receptor at an EcoRI restriction site encoding Glu-Phe at amino acids 75 and 76. The N-terminal sequence of 76 amino acids contains efficient translation initiation sequences and has 12 positively charged residues. To determine the minimum sequence requirement for efficient synthesis of recombinant protein from the cI fusion system, deletion analysis of the cI fusion sequence was performed. Deletions were performed by PCR mutagenesis employing an upstream primer which overlapped the initiator ATG and introduced an NdeI cloning site. The downstream primer overlapped the terminal sequence and introduced an EcoRI cloning site. These shortened N-terminal fusion sequences, consisting of amino acids 1–76 (SEQ ID NO:11; with 12 positively charged residues), amino acids 1–36 (SEQ ID NO:12; with 9 positively charged residues), amino acids 1–22 (SEQ ID NO:13; with 6 positively charged residues), amino acids 1–15 (SEQ ID NO:14; with 3 positively charged residues) and no leader (as control) were fused to the N-terminus of the EP$_2$ receptor and the resultant constructs were expressed in E. coli. Protein expression was monitored by Western blot analysis, utilizing an anti-EP$_2$ sheep polyclonal antibody, as well as the Ni-NTA-URP conjugate reactive with the 6×-his C-terminal fusion (FIG. 1). Because the 24H epitope lies within the first 36 aa of cI, this monoclonal anti-cI antibody was not useful for these experiments. In addition, these constructs were expressed in the pT7 "pET" vectors (Novagen, Madison, Wis.) to compare the efficacy of the T7 promoter versus the previously described ptac promoter. The T7 promoter has the advantage of being less "leaky" than tac, i.e., it has a lower basal level of transcription. The results of these comparative studies demonstrated that the ptac promoter was superior to the T7 promoter in yielding high steady state levels of protein. Overall, the greatest amount of expression was observed with the cI$^{1-76}$ construct, no expression was observed with the cI$^0$ (no leader sequence) construct and intermediate amounts of expression were observed with the $cI^{1-15}$, $cI^{1-22}$ and $cI^{1-36}$ constructs.

EXAMPLE 3
Overexpression of Non EP Receptor Proteins

The ability of the cI fusion system of this invention to produce a variety of proteins was assessed as follows: the pLJM5-22H plasmid encoding the fusion of the $PGEP_2EP_3$ receptor with the N-terminal domain of λ repressor was modified to remove the cDNA encoding the $PGEP_2EP_3$ receptor and DNA sequences encoding alternative target proteins were inserted as fusion proteins in-frame with and downstream from the tac promoter/cI fusion at amino acid 76 of the λ repressor protein. As a general plasmid construction strategy, the target protein was amplified by polymerase chain reaction using an upstream oligonucleotide which overlapped the N-terminal sequence of the target protein and introduced an NdeI site immediately upstream from the ATG start codon. The downstream oligonucleotide overlapped the final codons of the target protein (in general, six codons), removed the stop codon and introduced an XhoI site. This allowed introduction of the target sequence at the NdeI and XhoI restriction sites which flanked the $PGEP_2EP_3$ receptor in plasmid pLJM5-22H. The resulting constructs were fused at the N-terminus to the first 76 aa of λ repressor and at the C-terminus to the 6x-his tag.

Plasmid pSD1.63 his-fusion of the human CCR5 receptor with the N-terminal domain of λ repressor. Construct pSD1.63 his (SEQ ID NO:3) was assembled according to the general outline as described above. The plasmid allowed expression of the nucleotide sequence encoding the CCR5 protein, a chemokine receptor of the GPCR superfamily and the co-receptor for HIV entry into host cells.

The upstream oligonucleotide primer had the sequence:
5' GCGC CAT ATG GAT TAT AAG TGT CAA GTC CAA 3' (SEQ ID NO:29).

The downstream primer had the sequence:
5' GCCG CT CGA GGC CAA GCC CAC AGA TAT TTC CT 3' (SEQ ID NO:30).

The underlined sequence delineates the NdeI sequence in the upper primer and the XhoI sequence in the lower primer, respectively. The two primers were used to amplify the CCR5 receptor from human genomic DNA utilizing the following reaction conditions: 35 cycles of the following protocol: 1 min at 95° C., 15 sec at 95° C., 15 sec at 68° C., followed by a 10 min final extension at 72° C. The resultant amplified product of 1074 nt was digested with NdeI and XhoI and inserted into the expression vector.

The fusion protein was produced and purified as described for the $PGEP_2EP_3$ receptor, with modifications for optimal growth, induction times and temperatures. In brief, the culture conditions were as follows: Medium was inoculated with a 1:100 dilution of a fresh overnight culture and grown overnight for 24 hours at 30° C. in 2×LB medium containing 2% glucose and the appropriate antibiotics. Cells were collected by centrifugation and resuspended in 2×LB (no glucose) containing 1 mM IPTG and the appropriate antibiotics. Cells were then grown for varying times of induction at 30° C. and harvested by centrifugation. For the CCR-5 fusion protein, induction was overnight for 24 hours.

Plasmid pSD1.18 his-fusion of the human $β_2AR$ receptor with the N-terminal domain of λ repressor. Construct pSD1.18 his (SEQ ID NO:4) was assembled using a modification of the general outline described above. The natural stop codon of the semi-synthetic $β_2AR$ was removed by PCR, however the 5' end of the cDNA was subcloned into the EcoRi site at codon 75/76 of λ repressor, which is immediately upstream of the flanking NdeI site utilized in the previous constructs.

The sense oligonucleotide contains sequence internal to the $β_2AR$ and adds an Nco I and EcoRI site at the 5' end:

5' GCGCGAATTCACCATG GAA ATG AGA CCT GCT GTG ACT TC 3' (SEQ ID NO:31).

The mutagenic antisense oligonucleotide primer which removes the stop codon and introduces the XhoI site for fusion to the 6×his tag had the sequence:
5' CCGGG CT CGA GGC TAG CAG_TGA GTC ATT TGT ACT ACA AT 3' (SEQ ID NO:32).

The underlined sequence delineates the EcoRI and NcoI restriction sequences in the upper sense primer and the XhoI sequence in the lower antisense primer. These oligonucleotides were used to amplify a small internal $β_2AR$ sequence with convenient EcoRI and XhoI restriction sites at the terminal. This fragment was subcloned into the tac/cI fusion expression vector as an intermediate step. The resulting plasmid was digested with at NcoI and an (internal to $β_2AR$) EcoRV site contained within the original PCR fragment. The corresponding NcoI—EcoRV fragment of the $β_2AR$ cDNA was subdloned into this site, reconstituting the full length modified $β_2AR$ sequence. This resulted in the $cI^{1-76}$—$β_2AR$-6×his fusion protein cloned into the cI-fusion expression vector. The fusion protein was produced and purified as described herein for the $EP_3$ receptor with an overnight 24 hour induction.

Plasmid pSD1.134 his-fusion of the ROMK receptor with the N-terminal domain of λ repressor. Construct pSD1.134 his (SEQ ID NO:5) was assembled according to the general outline as described herein. The upstream oligonucleotide primer had the sequence:
5' GGGAATTC CAT ATG TTC AAA CAC CTC CGA AGA TGG 3' (SEQ ID NO:33). The downstream primer had the sequence: 5' CCGCTCGAGGC CAT CTG GGT GTC GTC CGT TTCA TC 3' (SEQ ID NO:34). The underlined sequence delineates EcoRI and NdeI sequences in the upper primer and the XhoI sequence in the lower primer, respectively. The two primers were used to amplify the ROMK channel from the cloned rat cDNA utilizing PCR. The resultant amplified product was digested with NdeI and XhoI and the 1.1 kb fragment was inserted into the expression vector. The resultant $cI^{1-76}$ fusion protein was under the control of the tac promoter. The fusion protein was produced and purified as described herein for the $PGEP_2EP_3$ receptor, with a three to five hour induction. The resulting yield of ROMK protein by this method was approximately 1 mg of purified protein/liter of bacterial culture when induced at $A_{600}$= 1 to 2.

Plasmid pSD2.46his-fusion of the human rho protein with the N-terminal domain of λ repressor. Construct pSD2.46his (SEQ ID NO:6) was assembled according to the general outline described herein. The resulting construct allowed expression of the nucleotide sequence encoding a fusion protein of $cI^{1-76}$ and the human rho protein, which is a cytoplasmic protein which is membrane-associated and a member of the family of small G-proteins. The upstream oligonucleotide primer had the sequence:
5' GCG CGC ATA TGG CTG CCA TCC GGA AG 3' (SEQ ID NO:35). The downstream primer had the sequence: 5' GCC GCT CGA GGC CAA GAC AAG GCA ACC AGA 3' (SEQ ID NO:36). The underlined sequence delineates an NdeI sequence in the upper primer and an XhoI sequence in the lower primer, respectively. The two primers were used to amplify rho from cloned human cDNA utilizing PCR. The resultant amplified product was digested with NdeI and XhoI and the 0.6 kb fragment was inserted into the expression vector. The resultant $cI^{1-76}$ fusion protein was under the control of the tac promoter. The fusion protein was produced and purified as described herein for the $PGEP_2EP_3$ receptor, with a three to 24 hour induction.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

Audoly, L. and R. M. Breyer. Substitution of charged amino acid residues in transmembrane regions 6 and 7 affect ligand binding and signal transduction of the prostaglandin $EP_3$ receptor. *Mol. Pharmacol.* 51:61–68 (1997).

Braiman et al. *J. Biol. Chem.* 262:9271–9276 (1987).

Breyer, R. M., R. B. Emerson, J. L. Tarng, M. D. Breyer, L. S. Davis, R. M. Abromson and S. M. Ferrenbach. Alternative splicing generates multiple isoforms of a rabbit prostaglandin $E_2$ receptor. *J. Biol. Chem.* 269(8):6163–6169 (1994).

Breyer, R. M. and R. T. Sauer. Mutational Analysis of the Fine Specificity of Binding of Monoclonal Antibody 51F to λ Repressor. *J. Biol. Chem.* 264(August 5):13355–13360 (1989a).

Breyer, R. M. and R. T. Sauer. Production and Characterization of Monoclonal Antibodies to the N-terminal Domain of λ Repressor. *J. Biol. Chem.* 264(August 5):13348–13354 (1989b).

Breyer, R. M., A. D. Strosberg and J.-G. Guillet. Mutational Analysis of Ligand Binding of β2 Adrenergic Receptor Expressed in *Escherichia coli*. *EMBO J.* 9(9):2679–2684 (1990).

Chapot, M. P., Y. Eshdat, S. Marullo, J.-G. Guillet, A. Charbit, A. D. Strosberg and C. Delavier-Klutchko. Localization and characterization of three different β adrenergic receptors expressed in *Escherichia coli*. *Eur. J. Biochem.* 187:137–144 (1990).

Goeddel, D. Z. *Methods in Enzymology* 185:3–7 (1990).

Harlow and Lane. *Antibodies: A Laboratory Manual*. Cold Spring Harbor Laboratory, Cold Spring Harbor, N.Y. (1988).

Le Caherec, F., et al. *J. Cell Science* 109:1285–1295 (1996).

Lewin. *Genes V*. Oxford University Press. Chapter 7, pp. 171–174 (1994).

Limbird, L. E. *Cell surface receptors: A short course on theory and methods*. Second edition. Kluwer Academic Publishers, Norwell, Mass. (1996).

Loisel, T. P., H. Ansanay, S. St-Onge, B. Gay, P. Boulanger, A. D. Strosberg, S. Marullo and M. Bouvier. Recovery of homogeneous and functional β2 adrenergic receptors from extracellular baculovirus particles. *Nature Biotechnology* 15:1300–1304 (1997).

Marullo, S., C. Delavier-Klutchko, Y. Eshdat, A. D. Strosberg and L. J. Emorine. Human β2 adrenergic receptors expressed in *E. coli* membranes retain their pharmacological properties. *Proc. Natl. Acad. Sci. U.S.A.* 85(October 1988):7551–7555 (1988).

Michieli, et al. *Oncogene* 12:775–784 (1996).

Sambrook et al. *Molecular Cloning: A Laboratory Manual*. 2d Ed. Cold Spring Harbor Laboratory, Cold Spring Harbor, N.Y. 1988.

Sander, P., S. Giunewald, Reilander and H. Michel. Expression of the human D2s dopamine receptor in yeasts *Saccharomyces cerevisae* and *Schizosaccharomyces pombe*: a comparative study. *FEBS Letters* 344:41–46 (1994).

Sauer, R. T. *Biochemistry* 17:1092–1100 (1978).

Sauer et al. *Nature* 279:396–400 (1979).

Zeidel, M. L., et al. *Biochemistry* 31:7436–7441 (1992).

Zweichal, A., et al. *Am. J. Physiol.* 261:F187–F196 (1991).

What is claimed is:

1. An isolated nucleic acid comprising a first nucleotide sequence encoding a bacteriophage lambda repressor protein, positioned upstream and in frame with a second nucleotide sequence encoding a eukaryotic G-protein coupled receptor protein, whereby expression of the nucleic acid results in a high yield of the protein.

2. The nucleic acid of claim 1, wherein the first nucleotide sequence encodes the N-terminal domain of the bacteriophage lambda repressor protein.

3. The nucleic acid of claim 1, wherein the first nucleotide sequence encodes amino acids 1–76 of the bacteriophage lambda repressor protein.

4. The nucleic acid of claim 1, wherein the first nucleotide sequence encodes at least 15 contiguous amino acids of the N-terminus of the bacteriophage lambda repressor protein.

5. The nucleic acid of 1, the second nucleotide sequence encodes a protein selected from the group consisting of rabbit prostaglandin $E_2EP_3$ receptor protein, human prostaglandin $E_2EP_2$ receptor protein, human chemokine receptor CCR-5 protein and human $\beta_2$ adrenergic receptor protein.

6. The nucleic acid of claim 2, wherein the second nucleotide sequence encodes a protein selected from the group consisting of rabbit prostaglandin $E_2EP_3$ receptor protein, human prostaglandin $E_2EP_2$ receptor protein, human chemokine receptor CCR-5 protein and human $\beta_2$ adrenergic receptor protein.

7. The nucleic acid of claim 3, wherein the second nucleotide sequence encodes a protein selected from the group consisting of rabbit prostaglandin $E_2EP_3$ receptor protein, human prostaglandin $E_2EP_2$ receptor protein, human chemokine receptor CCR-5 protein and human $\beta_2$ adrenergic receptor protein.

8. The nucleic acid of claim 4, wherein the second nucleotide sequence encodes a protein selected from the group consisting of rabbit prostaglandin $E_2EP_3$ receptor protein, human prostaglandin $E_2EP_2$ receptor protein, human chemokine receptor CCR-5 protein and human $\beta_2$ adrenergic receptor protein.

9. An isolated nucleic acid having the nucleotide sequence selected from the group consisting of SEQ ID NO:1 (rabbit prostaglandin $E_2EP_3$ receptor protein), SEQ ID NO:2 (human prostaglandin $E_2EP_2$ receptor protein), SEQ ID NO:3 (human chemokine receptor CCR-5 protein), SEQ ID NO:4 (human $\beta_2$ adrenergic receptor protein) and SEQ ID NO:5 (rat renal outer medullary $K^+$ channel protein).

10. A method of producing a eukaryotic G-protein coupled receptor protein in a bacterial cell comprising:
  a) introducing the nucleic acid of claim 1, wherein the second nucleotide sequence encodes a eukaryotic G-protein coupled receptor protein, into the bacterial cell; and
  b) culturing the bacterial cell under conditions whereby the second nucleotide sequence of the nucleic acid is expressed to produce the eukaryotic G-protein coupled receptor protein.

11. A method of producing a rabbit prostaglandin $E_2$ $EP_3$ receptor protein in a bacterial cell comprising:

a) introducing the nucleic acid of claim 1, wherein the second nucleotide sequence encodes the rabbit prostaglandin $E_2$ $EP_3$ receptor protein, into the bacterial cell; and
  b) culturing the cell under conditions whereby the second nucleotide sequence of the expression vector is expressed to produce the rabbit prostaglandin E2 $EP_3$ receptor protein.

12. A method of producing a human prostaglandin $E_2$ $EP_2$ receptor protein in a bacterial cell comprising:
  a) introducing the nucleic acid of claim 1, wherein the second nucleotide sequence encodes the human prostaglandin $E_2$ $EP_2$ receptor protein, into the bacterial cell; and
  b) culturing the bacterial cell under conditions whereby the second nucleotide sequence of the nucleic acid is expressed to produce the human prostaglandin $E_2$ $EP_2$ receptor protein.

13. A method of producing a human chemokine receptor CCR-5 protein in a bacterial cell comprising:
  a) introducing the nucleic acid of claim 1, wherein the second nucleotide sequence encodes the human chemokine receptor CCR-5 protein, into the bacterial cell; and
  b) culturing the bacterial cell under conditions whereby the second nucteotide sequence of the nucleic acid is expressed to produce the human chemokine receptor CCR-5 protein.

14. A method of producing a human $\beta_2$ adrenergic receptor protein in a bacterial cell comprising:
  a) introducing the nucleic acid of claim 1, wherein the second nucleotide sequence encodes the human $\beta_2$ adrenergic receptor protein, into the bacterial cell; and
  b) culturing the bacterial cell under conditions whereby the second nucleotide sequence of the nucleic acid is expressed to produce the human $\beta_2$ adrenergic receptor protein.

15. A fusion protein encoded by the nucleic acid of claim 1.

16. A fusion protein encoded by the nucleic acid of claim 2.

17. A fusion protein encoded by the nucleic acid of claim 3.

18. A fusion protein encoded by the nucleic acid of claim 4.

19. A fusion protein encoded by the nucleic acid of claim 5.

20. A fusion protein encoded by the nucleic acid of claim 6.

21. A fusion protein encoded by the nucleic acid of claim 7.

22. A fusion protein encoded by the nucleic acid of claim 8.

23. A fusion protein encoded by the nucleic acid of claim 9.

* * * * *